United States Patent [19]

Rabin

[11] Patent Number: 5,955,345
[45] Date of Patent: Sep. 21, 1999

[54] NUCLEIC ACIDS ENCODING PANCREATIC ISLET CELL ANTIGENS OBTAINED BY MOLECULAR CLONING

[75] Inventor: Daniel U. Rabin, Branford, Conn.

[73] Assignee: Bayer Corporation Formerly Molecular Diagnostics Inc., Tarrytown, N.Y.

[21] Appl. No.: 08/468,576

[22] Filed: Jun. 6, 1995

Related U.S. Application Data

[62] Division of application No. 08/239,276, May 5, 1994, which is a continuation of application No. 07/872,646, Jun. 8, 1992, abandoned, which is a continuation of application No. 07/715,181, Jun. 14, 1991, abandoned, which is a continuation-in-part of application No. 07/441,703, Dec. 4, 1989, abandoned, which is a continuation-in-part of application No. 07/312,543, Feb. 17, 1989, abandoned.

[51] Int. Cl.$^6$ .......................... C12N 1/20; C12N 15/00; C07H 17/00; C07K 14/00
[52] U.S. Cl. .............................. 435/252.3; 435/320.1; 435/325; 536/23.5; 530/350
[58] Field of Search ...................... 435/7.1, 7.21, 435/69.1, 69.3, 240.1, 252.3, 320.1, 325; 530/350; 536/22.1, 23.4, 23.5

[56] References Cited

U.S. PATENT DOCUMENTS

| | | | |
|---|---|---|---|
| 4,950,646 | 8/1990 | Wallner | 574/12 |
| 4,983,729 | 1/1991 | Sikora | 435/172.3 |
| 5,041,536 | 8/1991 | Brideau et al. | 530/350 |
| 5,171,568 | 12/1992 | Burke et al. | 424/186.1 |
| 5,200,318 | 4/1993 | Rabin et al. | 435/7.21 |
| 5,219,990 | 6/1993 | Androphy et al. | 530/350 |
| 5,229,274 | 7/1993 | Crawford et al. | 435/691 |
| 5,279,938 | 1/1994 | Rosa | 435/6 |
| 5,288,607 | 2/1994 | Emorine et al. | 435/6 |
| 5,366,883 | 11/1994 | Asada et al. | 435/202 |
| 5,420,019 | 5/1995 | Theofan et al. | 435/69.1 |
| 5,476,926 | 12/1995 | Spiegelman et al. | 436/24.1 |
| 5,489,432 | 2/1996 | Payne et al. | 424/405 |
| 5,489,513 | 2/1996 | Springer et al. | 435/6 |
| 5,492,809 | 2/1996 | Miller et al. | 435/6 |
| 5,505,943 | 4/1996 | Fortney et al. | 424/94.63 |
| 5,508,165 | 4/1996 | Halverson et al. | 435/6 |
| 5,512,460 | 4/1996 | Nauro et al. | 435/69.1 |
| 5,527,682 | 6/1996 | Owens et al. | 435/6 |
| 5,527,775 | 6/1996 | Shorr et al. | 514/12 |
| 5,532,127 | 7/1996 | Galllaltin et al. | 435/6 |
| 5,534,223 | 7/1996 | Boquet et al. | 422/61 |
| 5,538,892 | 7/1996 | Donahoe et al. | 435/240.2 |

OTHER PUBLICATIONS

*Joslin's Diabetes Mellitus*, 13th Edition, C. Kahn et al., editors, Lea & Febiger, Philadelphia, 1994, pp. 18–19.
*Diabetes*, Abstract Book, 56th Annual Meeting, Jun. 1996, Abstract Nos. 290, 291, 293–296, 879, 882, 893, 1128, 1129 and 1137.
C. Verge et al., *Diabetes*, 45: 926 (1996).
I. Durinovic–Bellò et al., *Diabetes*, 45: 795 (1996).
U. Roll et al., *Diabetes*, 45: 967 (1996).
R. Gianani et al., *Diabetes*, 44: 1340 (1995).
M. Myers et al., *Diabetes*, 44: 1290 (1995).
D. Rabin et al., *J. Immunology*, 152: 3183 (1994).
D. Rabin et al., *Diabetes*, 41: 183 (1992).
M. Lan et al., *DNA and Cell Biol.*, 13:505 (1994).
D. Rabin et al., *J. Immunol. Methods*, 156: 101 (1992).
Abstracts of Medline Search conducted on Jul. 22, 1996.
K. Krisch et al., *Lab. Invest.*, 58: 411 (1988).
M. Solimena et al., *EMBO Journal*, 15: 2102 (1996).
D. Karounos et al., *Diabetes*, 39: 1085 (1990).
D. Karounos et al., *Autoimmunity*, 6: 79 (1990).
C. Goodnow, *Proc.Natl.Acad.Sci. USA*, 93:2264 (1996).
A. Tarkowski et al., *Arthritis and Rheumatism*, 32:1087 (1989).
N. Seki, *J. Immunology*, 140: 1477 (1988).
D. Trentham, *Science*, 261: 1727 (1993).
J. Courtenay et al., *Nature*, 283: p. 666 only (1980).
S. Khare, *J. Immunmology*, 155: p. 3653 only (1995).
B. Driscoll et al., *J. Immunology*, 112: p. 392 only (1974).
M. Samson et al., *J. Immunology*, 155: p. 2737 only (1995).
P. Matsiota et al., *Ann.Inst.Pasteur Immunol.*, 139: 99 (1988), abstract only.
A. Wajgt et al., *Acta Neurol. Scand.*, 68: 337 (1983), abstract only.
D. Daniel et al., *Eur. J. Immunol.*, 25: 1056 (1995), abstract only.
D. Kaufman et al., *Nature*, 366: 69 (1993), abstract only.
R. Tisch et al., *Nature:* 366: 72 (1993), abstract only.
N. Schloot et al., *Immunology Today*, 16: 289 (1995).
*Official Gazette* for Jul. 30, 1996, p. 3679, abstract of U.S. Patent No. 5,541,095, issued to Hirschberg et al.
Srikanta et al (1986) Mol. Biol. Med. 3:113–127.
Karounos et al. (1988) Diabetes 37(5):30A.
Moncayo et al. (1988) Diabetologia 31(7):523A.
Tautz et al 1987 Nature 327:383–389.
Pringault et al 1986 EMBO J. 5(12):3119–3124.
Schnier et al 1982 PNAS 79:1008–1011.
Gibbs et al 1987 Nucleic Acids Res. 15(15):6293.
Tourvieille et al 1986 Science 243:610–614.
Kirckhausen et al 1987 Science 236:320–324.
Cool et al 1989 PNAS 86:5257–5261.

*Primary Examiner*—Karen Cochrane Carlson
*Attorney, Agent, or Firm*—Sprung Kramer Schaefer & Briscoe

[57] ABSTRACT

Pancreatic islet cell antigens (ICA) that bind with antibodies found in the sera of patients afflicted with insulin-dependent (Type I) diabetes mellitus (IDDM). ICA proteins are expressed by recombinant cloning vehicles comprising DNA inserts isolated from islet cells. Full sequence native ICA proteins, or protein or peptide fragments thereof, can be used in the diagnosis of IDDM and in detecting or blocking human immunoglobulin, T-cells, or B-cells involved in IDDM.

77 Claims, 14 Drawing Sheets

DIABETIC

NORMAL

DIABETIC

NORMAL

DIABETIC

NORMAL

DIABETIC

NORMAL

DIABETIC

NORMAL

DIABETIC

NORMAL

ICA CLONES 2/89

| SERUM | | 12 | 13 | 208 | 302 | 313 |
|---|---|---|---|---|---|---|
| 1 | 1 | 3 | 1 | | | 1 |
| 2 | 2 | | | | | |
| 3 | 3 | | | | ? | |
| 4 | 4 | | | | | |
| 5 | 5 | 2 | | 2 | | |
| 6 | 6 | 4 | 2 | 2 | | 3 |
| 7 | 7 | 3 | | 3 | 2 | |
| 8 | 9 | | | 4 | | |
| 9 | 10 | | | | | |
| 10 | 11 | | | | | |
| 11 | 12 | 3 | 2 | | | |
| 12 | 13 | | | | | |
| 13 | 14 | | | 4 | ? | |
| 14 | 15 | | | 3 | | |
| 15 | 17 | 3 | 2 | | | 2 |
| 16 | 18 | 3 | 2 | 1 | | 1 |
| 17 | 19 | ? | | | | |
| 18 | 20 | ? | | | 2 | |
| 19 | 21 | | 1 | 1 | 4 | |
| 20 | 23 | | | | 1 | |
| 21 | c1 | | | | | |
| 22 | c2 | | | | | |
| 23 | c3 | | | | | |
| 24 | c4 | | | | | |
| 25 | c5 | | | | | |
| 26 | c6 | | | | | |
| 27 | c7 | | | | | |
| 28 | c8 | | | 2 | | |
| 29 | c9 | | | | | |
| 30 | c10 | | | | | |

FIG. 7

DIABETIC

NORMAL

FIG. 9a
FIG. 9b
DIABETIC
NORMAL
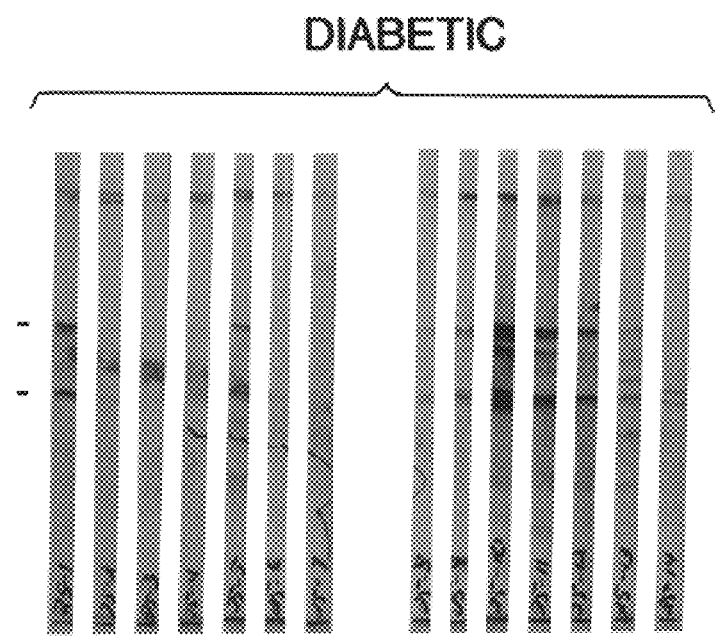
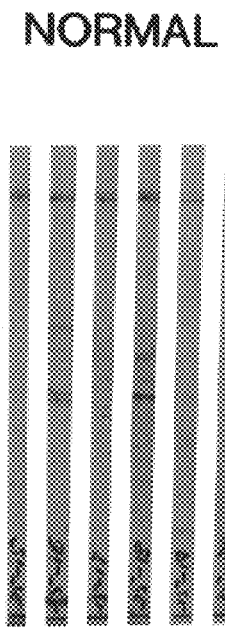

PROFILES

| SERUM | | 505 | 525 |
|---|---|---|---|
| 1 | 7601 | | 4 |
| 2 | 7645 | | |
| 3 | 7668 | | |
| 4 | 7677 | | |
| 5 | 13782 | | 4 |
| 6 | 13860 | 1 | 4 |
| 7 | 13916 | | |
| 8 | P5 | | 2 |
| 9 | P6 | 1 | |
| 10 | P7 | | 4 |
| 11 | P8 | | 3 |
| 12 | P21 | | 3 |
| 13 | P26 | 3 | |
| 14 | P28 | 2 | |
| 15 | MRC41 | | |
| 16 | MRC42 | | 1 |
| 17 | MRC43 | 1 | |
| 18 | MRC44 | | |
| 19 | MRC45 | | |
| 20 | MRC46 | | |

FIG. 10

```
                         SEQUENCE LISTING (1) GENERAL INFORMATION:

(iii) NUMBER OF SEQUENCES:  19

(2) INFORMATION FOR SEQ ID NO: 1:

(i) SEQUENCE CHARACTERISTICS:
        (A) LENGTH:    1397 nucleotides
        (B) TYPE:  nucleic acid
        (C) STRANDEDNESS: single
        (D) TOPOLOGY:  linear (xi) SEQUENCE DESCRIPTION:   SEQ ID NO: 1:

GG CCC ATG AAC GCC TTC ATG GTG TGG GCC AAG              32
              Pro Met Asn Ala Phe Met Val Trp Ala Lys
                            5                      10

GAT GAG CGG AGG AAG ATC CTG CAA GCC TTC                 62
           Asp Glu Arg Arg Lys Ile Leu Gln Ala Phe
                        15                      20

CCA GAC ATG CAC AAC TCC AGC ATC AGC AAG                 92
           Pro Asp Met His Asn Ser Ser Ile Ser Lys
                        25                      30

ATC CTT GGA TCT CGC TGG AAG TCC ATG ACC                 122
           Ile Leu Gly Ser Arg Trp Lys Ser Met Thr
                        35                      40

AAC CAG GAG AAN CAG CCC TAC TAT GAG GAA                 152
           Asn Gln Glu Xaa Gln Pro Tyr Tyr Glu Glu
                        45                      50

CAG GCT CTG CTG ATC GTC ATC ACC TGG AGA                 182
           Gln Ala Leu Leu Ile Val Ile Thr Trp Arg
                        55                      60

AGT ATC CTG ACT ACA AGT ACA AGC CGC GGC                 212
           Ser Ile Leu Thr Thr Ser Thr Ser Arg Gly
                        65                      70

CAA GCG CAC CTG CAT CGT GGA GGG CAA GCG                 242
           Gln Ala His Leu His Arg Gly Gly Gln Ala
                        75                      80
```

```
GCT GCG CGT GGG AGA GTA CAA GGC CCT GAT            272
Ala Ala Arg Gly Arg Val Gln Gly Pro Asp
            85                  90

GAG GAC CCG GCG TCA GGA TGC CCG CCA GAG            302
Glu Asp Pro Ala Ser Gly Cys Pro Pro Glu
            95                  100

CTA CGT GAT CCC CCC GCA GGC TGG CCA GGT            332
Leu Arg Asp Pro Pro Ala Gly Trp Pro Gly
            105                 110

GCA GAT GAG CTC CTC AGA TGT CCT GTA CCC            362
Ala Asp Glu Leu Leu Arg Cys Pro Val Pro
            115                 120

TCG GGC AGC AGG CAT GCC GCT GCA CAG CCA            392
Ser Gly Ser Arg His Ala Ala Ala Gln Pro
            125                 130

CTG GTG GAG CAC TAT GTC CCT CGT AGC CTG            422
Leu Val Glu His Tyr Val Pro Arg Ser Leu
            135                 140

GAC CCC AAC ATG CCT GTG ATC GTC AAC ACC            452
Asp Pro Asn Met Pro Val Ile Val Asn Thr
            145                 150

TGC AGC CTC AGA GAG GAG GGT GAG GGC ACA            482
Cys Ser Leu Arg Glu Glu Gly Glu Gly Thr
            155                 160

GAT GAC AGG CAC TCG GTG GCT GAT GGC GAG            512
Asp Asp Arg His Ser Val Ala Asp Gly Glu
            165                 170

ATG TAC CGG TAC AGC GAG GAC GAG GAC TCG            542
Met Tyr Arg Tyr Ser Glu Asp Glu Asp Ser
            175                 180

GAG GGT GAA GAG AAG AGC GAT GGG GAG TTG            572
Glu Gly Glu Glu Lys Ser Asp Gly Glu Leu
            185                 190

GTG GTG CTC ACA GAC TGATCCCGGC TGGGTGGCCT          607
Val Val Leu Thr Asp
            195

GGCCCCTTCT CCTCTGGGGA AGACCTTGTC CCAACTCGAT        647

GGGCACAGCC AGCCAACCTA AGACTATGTT GGTACTTGGA        687

CTTGTTCGTG CCCCAGAGAT GGGCAAAGCT GTGCACTTGC        727

AGATACATTC ATGAGGGGAG AGGCTCTCTC CCTTCCTGAG        767

GAGCTGTTGG CCTGGGTGGG CAGGAACTGC AGTATGGCCA        807

TGGGCTGAGC AGGCTGAGCA CCTCAGCCTT TAGGGCTTAT        847

GGCCAGGGGA CACTGTATGA CTCTCCTCTC CTGCAGGTGT        887

CTATCCACCT GGGGTATGGC ATCTACCGAC CTGTCTCCCT        927

GGGGTCACAT GCTTTGTTTC CAGGCTTGTC CTGGCTGGAC        967

CAGCCACTGT GGGACCAACA CCCCTCCCAC ACTCCCCCAG       1007

ACTGCTCGTC TATCACCAGG ATCGCTTTGT ACTTTGTGCA       1047

AAAGGGTCTG GCTGTCCCTT GCTGTTTTCA TCTCTGCCAA       1087

GCCTATTGTG CCTCTGGCTG CTGTATGTGT GCGCGTGCAC       1127

GTGTGTGTGT TTCATCTGTT CATTCACTGC ACAGAGTATT       1167

TATTGTGTGC CCACTACGTG CCAGGCACTG TTGCTGAGTT       1207

CCTGTGGGTG TGTCTCTCGA TGCCACTCCT GCTTCTCTGG       1247
```

|     |     |
| --- | --- |
| GGGCCTCTTT CTGTGCTTCT CTTTGTCCCC AAATTGCTAC | 1287 |
| CTCTTTGTCA GTCTGGGTGT CTCAGGTTCT GTGTGTCCTT | 1327 |
| GTGTGCATTT CTGTCTCTCT CTGTCCTCGT CTCTCTGCAA | 1367 |
| GGCCCTCTAT TTCTCTCTTT CTTGGTGTCT | 1397 |

(2) INFORMATION FOR SEQ ID NO: 2:

(i) SEQUENCE CHARACTERISTICS:
      (A) LENGTH: 5051 nucleotides
      (B) TYPE: nucleic acid
      (C) STRANDEDNESS: single
      (D) TOPOLOGY: linear (xi) SEQUENCE DESCRIPTION: SEQ ID NO: 2:

```
GGCAGAGCTT GAAGA ATG TCT TCC AAG CAA                       30
                Met Ser Ser Lys Gln
                              5

GCC ACC TCT CCA TTT GCC TGT GCA GCT GAT                    60
Ala Thr Ser Pro Phe Ala Cys Ala Ala Asp
              10                  15

GGA GAG GAT GCA ATG ACC CAG GAT TTA ACC                    90
Gly gln Asp Ala Met Thr Gln Asp Leu Thr
              20                  25

TCA AGG GAA AAG GAA GAG GGC AGT GAT CAA                   120
Ser Arg Glu Lys Glu Glu Gly Ser Asp Gln
              30                  35

CAT GTG GCC TCC CAT CTG CCT CTG CAC CCC                   150
His Val Ala Ser His Leu Pro Leu His Pro
              40                  45

ATA ATG CAC AAC AAA CCT CAC TCT GAG GAG                   180
Ile Met His Asn Lys Pro His Ser Glu Glu
              50                  55

CTA CCA ACA CTT GTC AGT ACC ATT CAA CAA                   210
Leu Pro Thr Leu Val Ser Thr Ile Gln Gln
              60                  65

GAT GCT GAC TGG GAC AGC GTT CTG TCA TCT                   240
Asp Ala Asp Trp Asp Ser Val Leu Ser Ser
              70                  75

CAG CAA AGA ATG GAA TCA GAG AAT AAT AAG                   270
Gln Gln Arg Met Glu Ser Glu Asn Asn Lys
              80                  85

TTA TGT TCC CTA TAT TCC TTC CGA AAT ACC                   300
Leu Cys Ser Leu Tyr Ser Phe Arg Asn Thr
              90                  95

TCT ACC TCA CCA CAT AAG CCT GAC GAA GGG                   330
Ser Thr Ser Pro His Lys Pro Asp Glu Gly
             100                 105

AGT CGG GAC CGT GAG ATA ATG ACC AGT GTT                   360
Ser Arg Asp Arg Glu Ile Met Thr Ser Val
             110                 115

ACT TTT GGA ACC CCA GAG CGC CGC AAA GGG                   390
Thr Phe Gly Thr Pro Glu Arg Arg Lys Gly
             120                 125

AGT CTT GCC GAT GTG GTG GAC ACA CTG AAA                   420
Ser Leu Ala Asp Val Val Asp Thr Leu Lys
             130                 135

CAG AAG AAG CTT GAG GAA ATG ACT CGG ACT                   450
Gln Lys Lys Leu Glu Glu Met Thr Arg Thr
             140                 145
```

```
GAA CAA GAG GAT TCC TCC TGC AGT GAA AAA                    480
Glu Gln Glu Asp Ser Ser Cys Met Glu Lys
            150                 155

CTA CTT TCA AAA GAT TGG AAG GAA AAA ATG                    510
Leu Leu Ser Lys Asp Trp Lys Glu Lys Met
            160                 165

GAA AGA CTA AAT ACC AGT GAA CTT CTT GGA                    540
Glu Arg Leu Asn Thr Ser Glu Leu Leu Gly
            170                 175

GAA ATT AAA GGT ACA CCT GAG AGC CTG GCA                    570
Glu Ile Lys Gly Thr Pro Glu Ser Leu Ala
            180                 185

GAA AAA GAA CGG CAG CTC TCC ACC ATG ATT                    600
Glu Lys Glu Arg Gln Leu Ser Thr Met Ile
            190                 195

ACC CAG CTG ATC AGT TTA CGG GAG CAG CTA                    630
Thr Gln Leu Ile Ser Leu Arg Glu Gln Leu
            200                 205

CTG GCA GCG CAT GAT GAA AGA AAA AAA CTG                    660
Leu Ala Ala His Asp Glu Arg Lys Lys Leu
            210                 215

GCA GCG TCA CAA ATT GAG AAA CAA CGG CAG                    690
Ala Ala Ser Gln Ile Glu Lys Gln Arg Gln
            220                 225

CAA ATG GAC CTT GCT CGC CAA CAG CAA GAA                    720
Gln Met Asp Leu Ala Arg Gln Gln Gln Glu
            230                 235

CAG ATT GCG AGA CAA CAG CAG CAA CTT CTG                    750
Gln Ile Ala Arg Gln Gln Gln Gln Leu Leu
            240                 245

CAA CAG CAG CAC AAA ATT AAT CTC CTG CAG                    780
Gln Gln Gln His Lys Ile Asn Leu Leu Gln
            250                 255

CAA CAG ATC CAG GTT CAG GGT CAC ATG CCT                    810
Gln Gln Ile Gln Val Gln Gly His Met Pro
            260                 265

CCG CTC ATG ATC CCA ATT TTT CCA CAT GAC                    840
Pro Leu Met Ile Pro Ile Phe Pro His Asp
            270                 275

CAG CGG ACT CTG GCA GCA GCT GCT GCT GCC                    870
Gln Arg Thr Leu Ala Ala Ala Ala Ala Ala
            280                 285

CAA CAG GGA TTC CTC TTC CCC CCT GGA ATA                    900
Gln Gln Gly Phe Leu Phe Pro Pro Gly Ile
            290                 295

ACA TAC AAA CCA GGT GAT AAC TAC CCC GTA                    930
Thr Tyr Lys Pro Gly Asp Asn Tyr Pro Val
            300                 305

CAG TTC ATT CCA TCA ACA ATG GCA GCT GCT                    960
Gln Phe Ile Pro Ser Thr Met Ala Ala Ala
            310                 315

GCT GCT TCT GGA CTC AGC CCT TTA CAG CTC                    990
Ala Ala Ser Gly Leu Ser Pro Leu Gln Leu
            320                 325

CAG AAG GGT CAT GTC TCC CAC CCA CAA ATT                   1020
Gln Lys Gly His Val Ser His Pro Gln Ile
            330                 335

AAC CAA AGG CTA AAG GGC CTA AGT GAC CGT                   1050
Asn Gln Arg Leu Lys Gly Leu Ser Asp Arg
            340                 345
```

| | |
|---|---|
| TTT GGC AGG AAT TTG GAC ACC TTT GAA CAT<br>Phe Gly Arg Asn Leu Asp Thr Phe Glu His<br>350 355 | 1080 |
| GGT GGT GGC CAC TCT TAC AAC CAC AAA CAG<br>Gly Gly Gly His Ser Tyr Asn His Lys Gln<br>360 365 | 1110 |
| ATT GAG CAG CTC TAT GCC GCT CAG CTG GCC<br>Ile Glu Gln Leu Tyr Ala Ala Gln Leu Ala<br>370 375 | 1140 |
| AGC ATG CAG GTG TCA CCT GGA GCA AAG ATG<br>Ser Met Gln Val Ser Pro Gly Ala Lys Met<br>380 385 | 1170 |
| CCA TCA ACT CCA CAG CCA CCA AAC ACA GCA<br>Pro Ser Thr Pro Gln Pro Pro Asn Thr Ala<br>390 395 | 1200 |
| GGG ACG GTC TCA CCT ACT GGG ATA AAA AAT<br>Gly Thr Val Ser Pro Thr Gly Ile Lys Asn<br>400 405 | 1230 |
| GAA AAG AGA GGG ACC AGC CCT GTA ACT CAA<br>Glu Lys Arg Gly Thr Ser Pro Val Thr Gln<br>410 415 | 1260 |
| GTT AAG GAT GAA GCA GCA GCA CAG CCT CTG<br>Val Lys Asp Glu Ala Ala Ala Gln Pro Leu<br>420 425 | 1290 |
| AAT CTC TCA TCC CGA CCC AAG ACA GCA GAG<br>Asn Leu Ser Ser Arg Pro Lys Thr Ala Glu<br>430 435 | 1320 |
| CCT GTA AAG TCC CCA ACG TCT CCC ACC CAG<br>Pro Val Lys Ser Pro Thr Ser Pro Thr Gln<br>440 445 | 1350 |
| AAC CTC TTC CCA GCC AGC AAA ACC AGC CCT<br>Asn Leu Phe Pro Ala Ser Lys Thr Ser Pro<br>450 455 | 1380 |
| GTC AAT CTG CCA AAC AAA AGC AGC ATC CCT<br>Val Asn Leu Pro Asn Lys Ser Ser Ile Pro<br>460 465 | 1410 |
| AGC CCC ATT GGA GGA AGC CTG GGA AGA GGA<br>Ser Pro Ile Gly Gly Ser Leu Gly Arg Gly<br>470 475 | 1440 |
| TCC TCT TTA GAT ATC CTA TCT AGT CTC AAC<br>Ser Ser Leu Asp Ile Leu Ser Ser Leu Asn<br>480 485 | 1470 |
| TCC CCT GCC CTT TTT GGG GAT CAG GAT ACA<br>Ser Pro Ala Leu Phe Gly Asp Gln Asp Thr<br>490 495 | 1500 |
| GTG ATG AAA GCC ATT CAG GAG GCG CGG AAG<br>Val Met Lys Ala Ile Gln Glu Ala Arg Lys<br>500 505 | 1530 |
| ATG CGA GAG CAG ATC CAG CGG GAG CAA CAG<br>Met Arg Glu Gln Ile Gln Arg Glu Gln Gln<br>510 515 | 1560 |
| CAG CAA CAG CCA CAT GGT GTT GAC GGG AAA<br>Gln Gln Gln Pro His Gly Val Asp Gly Lys<br>520 525 | 1590 |
| CTG TCC TCC ATA AAT AAT ATG GGG CTG AAT<br>Lys Ser Ser Ile Asn Asn Met Gly Leu Asn<br>530 535 | 1620 |
| AGC TGC AGG AAT GAA AAG GAA AGA ACG CGC<br>Ser Cys Arg Asn Glu Lys Glu Arg Thr Arg<br>540 545 | 1650 |

| | |
|---|---|
| TTT GAG AAT TTG GNN CCC CAG TTA ACG GGA<br>Phe Glu Asn Leu Xaa Pro Gln Leu Thr Gly<br>550 555 | 1680 |
| AAG TCA AAT GAA GAT GGA AAA CTG GGC CCA<br>Lys Ser Asn Glu Asp Gly Lys Leu Gly Pro<br>560 565 | 1710 |
| GGT GTC ATC GAC CTT ACT CGG CCA GAA GAT<br>Gly Val Ile Asp Leu Thr Arg Pro Glu Asp<br>570 575 | 1740 |
| GCA GAG GGA GGT GCC ACT GTG GCT GAA GCA<br>Ala Glu Gly Gly Ala Thr Val Ala Glu Ala<br>580 585 | 1770 |
| CGA GTC TAC AGG GAC GCC CGC GGC CTG CCA<br>Arg Val Tyr Arg Asp Ala Arg Gly Leu Pro<br>590 595 | 1800 |
| GCA GCG AGC CAC ACA TTA AGC GAC CAA<br>Ala Ala Ser His Thr Leu Ser Asp Gln<br>600 | 1827 |
| TGAATGCATT CATGGTTTGG GCAAAGGATG AGAGGAGAAA | 1867 |
| AATCCTTCAG GCCTTCCCCG ACATGCATAA CTCCAACATT | 1907 |
| AGCAAAATCT TAGGATCTCG CTGGAAATCA ATGTCCAACC | 1947 |
| AGGAGAAGCA ACCTTATTAT GAAGAGCAGG CCCGGCTAAG | 1987 |
| CAAGATCCAC TTAGAGAAGT ACCCAAACTA TAAATACAAA | 2027 |
| CCCCGACCGA AACNCACCTG CATTGTTGAT GGCAAAAAGC | 2067 |
| TTCGGATTGG GGAGTATAAG CAACTGATGA GGTCTCGGAG | 2107 |
| ACAGGAGATG AGGCAGTTCT TTACTGTGGG CAACAGCCT | 2147 |
| CAGATTCCAA TCACCACAGG AACAGGTGTT GTGTATCCTG | 2187 |
| GTGCTATCAC TATGGCAACT ACCACACCAT CGCCTCAGAT | 2227 |
| GACATCTGAC TGCTCTAGCA CCTCGGCCAG CGCGGAGCCC | 2267 |
| AGCCTCCCGG TCATCCAGAG CACTTATGGT ATGAAGACAG | 2307 |
| ATGGCGGAAG CTAGCTGGAA ATGAAATGAT CAATGGAGAG | 2347 |
| GATGAAATGG AAATGTATGA TGACTATGAA GATGACCCCA | 2387 |
| AATCAGACTA TAGCAGTGAA AATGAAGCCC CGGAGGCTGT | 2427 |
| CAGAGCCAAC TGAGGAGTTT TTGTTTGCTG AATTAAAGTA | 2467 |
| CTCTGACATT TCACCCCCCT CCCCAACAAA GAGTTATCCA | 2507 |
| AGAGCCCGCA TGCATTTGTG GCTCCACAAT TACATCAGCA | 2547 |
| GAATGGTCTT AATTGTTTCG TAAAGTGTGA GACAGATTAA | 2587 |
| GTTTTCCCTG ATTTTTCATG AACTTGAGTT TTTTGTTGTT | 2627 |
| ATTGTTATTG TTGTTGTTGT TGTTTTTTTT TTTGTTGTT | 2667 |
| ATTGTTATTG TTGTTGTTGT TGTTTTTTTA ATTTAGGTGA | 2707 |
| AGACATATTA AATATGAGAC ACCAGGACTT GAAACTTATC | 2747 |
| TCAACCCGTA GATGTCTTAC AAGTCTTATA TTTTTGTCTT | 2787 |
| ACTTTTTTTT TCTTTTGGAT GTTGATAAAG GTTAAGTTA | 2827 |
| CTGTTTTAGA TGGGGTTAAA CATTCTCACT CAGGTATGCT | 2867 |
| GTGCCGGCCT ACAGGTTGTG AATGTGTTTT TTATTCTGAA | 2907 |
| TTATTTTAGA AAACAACTGA GGATTTCATA TTGTGAAACA | 2947 |

| | |
|---|---|
| GGACAAGTCC ACGGCGTGTG CAGCTGCATG TAGAGCATAT | 2987 |
| TCAAAAGGCC TCGGAATTCC AATTTTCCAT TTGTAGAGTT | 3027 |
| AAACTTTGAA TGTGCCAAAC TTTTTCGTAA CTTTTGAATC | 3067 |
| TTAATATTTT GAAAGTCTTA AGGAGACAC TGCAAAGTCT | 3107 |
| TAGACAATCT TTGGCATCTT AAAATAAAAT AGCAAACCAA | 3147 |
| CATTTTTTTT TCCAGAAAAT GGTAAGGTAC TCAGGAATCT | 3187 |
| GGAGACAAGA TATTGTAAGG AATGAACAAG GTTGCCACAG | 3227 |
| TGCATGGACC CAATTGTGTT TGCCTGTTGA CGTGCCATCA | 3267 |
| GTGCGTGATG TGGTATGACA TACACACACC AGAGCAACCG | 3307 |
| CCACACCAGA TATCGACAGA GTGGTCTTCT CTGCCTGAGA | 3347 |
| CCACCTCTCA CTACATCCAT TATCCCTTTG CCTTTAACCC | 3387 |
| TGACATTCAG TCTTAACACA TTTTATCTTA AATAATTTAT | 3427 |
| TCATTCCAGA ATGTCAAGGG TCCACTTGCT ATTTATTTTT | 3467 |
| TTTCAATTGT TGGTGCATTA ATTTAATAAT TCTTGTTTTT | 3507 |
| CACCTTCCTT CCCCGAAGAA CTTTTCCGTC CTTTTCACCT | 3547 |
| CCTTCTCCTG TGTACATAGT GATTTTATGT CCCCAGAACG | 3587 |
| CCTGGAAGCA TTTCTGAAAC CAAGATATTA TTAAAAACCT | 3627 |
| ATTATTGTTT TTAATCATGA GTATGTATCT GGCTGCAGGG | 3667 |
| CTGTGTATTG GGATATAGGT ATATAGTCTT ACACTTAAAC | 3707 |
| AGGTATGCCC CTGAGGTTCA CTGTGACCTC AAGTCTTTTG | 3747 |
| CCAGAATTTT CCCCTAATTC AGTTCACAAG TGGTAGGGTC | 3787 |
| TGCATCAGTG GCATTTCCCC CTGAATTCCA TTCAGCAGCA | 3827 |
| AGGTTCAACA GTGGTGACTG CCAGGCAGGA GAGTCCTGCG | 3867 |
| GCCAAACCTG AAGCCCAAGG CTCGTGGGCC ATGCAGGAAT | 3907 |
| CTCAGTGAAG CTGTCATGGG CTGGCACCTT TACACTGAGT | 3947 |
| TGCCTTGTCC CAGCTGGCAC ATCTAGGGAG TTCATTGCAA | 3987 |
| AATCCCCAGG ATGCAAAAAG CCACATGACA GCCTCAGAGC | 4027 |
| AAAGATGGTG GCAAATAGTC ATGATACATC TAGAGAATGA | 4067 |
| AAGAAAACTG TAAGGGAGGA GAAGGAGGGG AATACATTCC | 4107 |
| CTATATGGGA TGTTCCTACT GTTAACCTGT GGGAACAGAT | 4147 |
| AGCTCCGGGG GCAGCAGATG AGTTCCTCTG GCTGACTCTA | 4187 |
| TCTGTAGCCA CATGGGGACC TGCCTACGTG TGAACAAAAT | 4227 |
| GAACTGCACT TATCACACAA GGATTTCTTT GAAGACATGC | 4267 |
| TACTGGGGTG GGAAGCAGTG AGGTTTTATT CCCCATCTCC | 4307 |
| TAACTACAGG GAGCTCTGCC ATGTCATTTT GGCCTTCCTG | 4347 |
| AAACTAGGAC AGGTTGTCTA TCGGGGGGCT TCCCCCAGAG | 4387 |
| AGGTTTAGTG GGAGAATGTC AGTGAATGGG ATAGTTCACC | 4427 |
| TCATGGGACA ACCCAGAATC TGATCACCAG GACATAGGAA | 4467 |
| TGGCCCCATC AGATTTCCTG AGCCATTTTG TCACTTGGAA | 4507 |
| GAAAATAGTG TACCTTTGTA TTTATTTAAG AGTGCTCAAG | 4547 |

```
          GCCTAATAGC AATAAACAGG TCTAGCCAAG AAATTACAAG                    4587

CTATTCTGTT AGCTGGGAGT GCTCTCTATA AGCTGATTAA                    4627

GGTACTGATA GGAACTCTTT GTTATTCATG TTGGTTGGGG                    4667

ATTAGAAATT TGTTTTTGTA CATTTATTTC AAATGAGGAG                    4707

GAGGTCATTT TTTCTCTCAA AAAATGAGTA TTTATTATTG                    4747

TCTTACTGAT TTCTTTGATT ATATACCTCT CCTCCTCAGT                    4787

TCACTCTTGT TTTTTTTCTT TCTCTTTGGC TTTTGCTTTT                    4827

GCTCTCTCTC ACTTCTTTCT TATTTTGTTG CATTGGTAGA                    4867

GTGTTGTATG GCTAGCATTG TATTGTATGT AATTAATTTT                    4907

GCACAAAAGC AAACATTTAG CATAGTAGGT TAATTTTGTT                    4947

TGTTTTTATG ACCATGCCAA AATAATATTC TGGGCTGGTG                    4987

GAGAACAAAG GACTATTCTT TAGGACTGAA ACTTGATTTT                    5027

GCTCATAGTA AGTAAAAAAA AAAA                                     5051
```

(2) INFORMATION FOR SEQ ID NO: 3:

(i) SEQUENCE CHARACTERISTICS:
        (A) LENGTH: 575 nucleotides
        (B) TYPE: nucleic acid
        (C) STRANDEDNESS: single
        (D) TOPOLOGY: linear (xi) SEQUENCE DESCRIPTION: SEQ ID NO: 3:

```
          AA ATT GAG AAG CTC AAA CTT GAG ATT GAG AAA                    32
             Ile Glu Lys Leu Lys Leu Glu Ile Glu Lys
                          5                  10

CTG AAA GCT GAA TCT GGG AAT CCA TCT ATT                        62
          Leu Lys Ala Glu Ser Gly Asn Pro Ser Ile
                       15                  20

CGG CAG AAG ATA CGC TTA AAA GAT AAA GCA                        92
          Arg Gln Lys Ile Arg Leu Lys Asp Lys Ala
                       25                  30

GCA GAT GCC AAA AAA ATT CAG GAT CTG GAG                       122
          Ala Asp Ala Lys Lys Ile Gln Asp Leu Glu
                       35                  40

CGA CAA GTT AAG GAA ATG GAA GGG ATT CTG                       152
          Arg Gln Val Lys Glu Met Glu Gly Ile Leu
                       45                  50

AAG AGA AGA TAT CCC AAT TCT TTA CCT GCT                       182
          Lys Arg Arg Tyr Pro Asn Ser Leu Pro Ala
                       55                  60

TTA ATA TTG GCT GCA TCA GCA GCT GGT GAT                       212
          Leu Ile Leu Ala Ala Ser Ala Ala Gly Asp
                       65                  70

ACA GTG GAT AAA AAT ACA GTG GAA TTT ATG                       242
          Thr Val Asp Lys Asn Thr Val Glu Phe Met
                       75                  80

GAG AAA AGG ATA AAA AAG CTA GAA GCT GAT                       272
          Glu Lys Arg Ile Lys Lys Leu Glu Ala Asp
                       85                  90

CTG GAG GGC AAA GAT GAA GAT GCA AAG AAA                       302
          Leu Glu Gly Lys Asp Glu Asp Ala Lys Lys
                       95                 100

AGC CTT CGT ACC ATG GAA CAA CAG TTT CAG                       332
          Ser Leu Arg Thr Met Glu Gln Gln Phe Gln
                      105                 110
```

```
AAA ATG AAG ATT CAG TAT GAA CAA AGA CTA                         362
Lys Met Lys Ile Gln Tyr Glu Gln Arg Leu
            115                 120

GAG CAG CAG GAG CAG CTA CTT GCC TGC AAA                         392
Glu Gln Gln Glu Gln Leu Leu Ala Cys Lys
            125                 130

TTG AAT CAA CAT GAC TCT CCC AGA ATT AAA                         422
Leu Asn Gln His Asp Ser Pro Arg Ile Lys
            135                 140

GCC CTA GAG AAG GAA CTT GAT GAC ATC AAG                         452
Ala Leu Glu Lys Glu Leu Asp Asp Ile Lys
            145                 150

GAA GCC CAT CAG ATC ACT GTA AGA AAC CTT                         482
Glu Ala His Gln Ile Thr Val Arg Asn Leu
            155                 160

GAA GCC GAA ATA GAC GTT CTT AAA CAT CAG                         512
Glu Ala Glu Ile Asp Val Leu Lys His Gln
            165                 170

AAT GCT GAA TTA GAC GTC AAG AAA AAT GAT                         542
Asn Ala Glu Leu Asp Val Lys Lys Asn Asp
            175                 180

AAA GAT GAT GAA GAT TTT CAG TCT ATA GAA                         572
Lys Asp Asp Glu Asp Phe Gln Ser Ile Glu
            185                 190

TTC                                                             575
Phe (2) INFORMATION FOR SEQ ID NO: 4:

(i) SEQUENCE CHARACTERISTICS:
        (A) LENGTH: 794 nucleotides
        (B) TYPE: nucleic acid
        (C) STRANDEDNESS: single
        (D) TOPOLOGY: linear (xi) SEQUENCE DESCRIPTION: SEQ ID NO: 4:

GC GAT ACA CCG GGC GTT AAA GTG GGT GAT GAA                 32
           Asp Thr Pro Cys Val Lys Val Gly Asp Glu
                       5                  10

GTG GAG GTA ATG GTT GTT GAA AAA GAA GAC                    62
        Val Glu Val Met Val Val Glu Lys Glu Asp
                    15                  20

CGT AAC GGC AAT TTA AAC CTA AGC CGT AAA                    92
        Arg Asn Gly Asn Leu Asn Leu Ser Arg Lys
                    25                  30

AGT GCC CGC ATT TTC CGT GCT TGG GAA AGA                   122
        Ser Ala Arg Ile Phe Arg Ala Trp Glu Arg
                    35                  40

ATT ATG GAA GTG CAT AAA ACA GGT GAA GTG                   152
        Ile Met Glu Val His Lys Thr Gly Glu Val
                    45                  50

GTT ACA GGT TTG GTT ACC AGC AAA ACA AAA                   182
        Val Thr Gly Leu Val Thr Ser Lys Thr Lys
                    55                  60

GGT GGC TTG ATT GTA GAT GTT TTC GGT ATG                   212
        Gly Gly Leu Ile Val Asp Val Phe Gly Met
                    65                  70

GAA ACT TTC TTA CCG GGT TCT CAA ATT GAT                   242
        Glu Thr Phe Leu Pro Gly Ser Gln Ile Asp
                    75                  80
```

```
GTT AAA CCC GTT ACA GAT TAC GAC CAG TTT                                272
Val Lys Pro Val Thr Asp Tyr Asp Gln Phe
             85                      90

GTT GGT AAA ACA ATG GAG TTT AAA GTT GTT                                302
Val Gly Lys Thr Met Glu Phe Lys Val Val
             95                     100

AAG ATT AAC GAA ACA ATT AAG AAT GCT GTT                                332
Lys Ile Asn Glu Thr Ile Lys Asn Ala Val
            105                     110

GTA TCT CAC AAA GCA TTA ATT GAA AGC GAT                                362
Val Ser His Lys Ala Leu Ile Glu Ser Asp
            115                     120

ATT GAA GCA CAA CGT GCT GAA ATA ATG AGC                                392
Ile Glu Ala Gln Arg Ala Glu Ile Met Ser
            125                     130

AAA TTA GAA AAA GGT CAG GTG TTA GAA GGT                                422
Lys Leu Glu Lys Gly Gln Val Leu Glu Gly
            135                     140

ACT GTT AAG AAC ATT ACA GAC TTC GGT GCA                                452
Thr Val Lys Asn Ile Thr Asp Phe Gly Ala
            145                     150

TTT ATG GAC CTT GGT GGC TTA GAC GGC TTA                                482
Phe Met Asp Leu Gly Gly Leu Asp Gly Leu
            155                     160

TTA TAC ATT ACA GAT ATT TCA TGG GGC AGA                                512
Leu Tyr Ile Thr Asp Ile Ser Trp Gly Arg
            165                     170

ATT TCT CAC CCA AGC GAA GTA TTG AAA ATG                                542
Ile Ser His Pro Ser Glu Val Leu Lys Met
            175                     180

GAT CAG AAA TTA AAT GTG GTT GTA TTA GAC                                572
Asp Gln Lys Leu Asn Val Val Val Leu Asp
            185                     190

TTT GAT GAT GAT AAA AAA CGT ATC AGC CTT                                602
Phe Asp Asp Asp Lys Lys Arg Ile Ser Leu
            195                     200

GGT TTA AAA CAA TTA ACA CCG CAT CCT TGG                                632
Gly Leu Lys Gln Leu Thr Pro His Pro Trp
            205                     210

GAA GTA TTA CCT GAA GGT TTG GCT GAA GGT                                662
Glu Val Leu Pro Glu Gly Leu Ala Glu Gly
            215                     220

GCT ATT GTA AAA GGT AAA GTG GTA AAT ATT                                692
Ala Ile Val Lys Gly Lys Val Val Asn Ile
            225                     230

GAA GAT TAC GGT GCA TTC TTA GAA ATT CAA                                722
Glu Asp Tyr Gly Ala Phe Leu Glu Ile Gln
            235                     240

CCG GGG GTT GAA GGT TTG GTT CAC GTA AGT                                752
Pro Gly Val Glu Gly Leu Val His Val Ser
            245                     250

GAA ATT ACC TGG GAA AAT ACA CCA ATC AAC                                782
Glu Ile Thr Trp Glu Asn Thr Pro Ile Asn
            255                     260

GCT AAA GAA TTC                                                        794
Ala Lys Glu Phe
```

(2) INFOR FOR SEQ ID NO: 5:

(i) CE CHARACTERISTICS:
        ENGTH: 1570 nucleotides

-continued

YPE: nucleic acid
TRANDEDNESS: single
OPOLOGY: linear (xi) CE DESCRIPTION: SEQ ID NO: 5:

| G GAT GGC TCC CCC AAC ACC CCC TTC CGT AAG | 31 |
| Asp Gly Ser Pro Asn Thr Pro Phe Arg Lys | |
| 5 10 | |

| GAC CTC ATC AGC CTG GAC TCA TCC CCA GCC | 61 |
| Asp Leu Ile Ser Leu Asp Ser Ser Pro Ala | |
| 15 20 | |

| AAG GAG CGG CTG GAG GAC GGC TGT GTG CAC | 91 |
| Lys Glu Arg Leu Glu Asp Gly Cys Val His | |
| 25 30 | |

| CCA CTG GAG GAA GCC ATG CTG AGC TGC GAC | 121 |
| Pro Leu Glu Glu Ala Met Leu Ser Cys Asp | |
| 35 40 | |

| ATG GAT GGC TCC CGC CAC TTC CCC GAG TCC | 151 |
| Met Asp Gly Ser Arg His Phe Pro Glu Ser | |
| 45 50 | |

| CGA AAC AGC AGC CAC ATC AAG AGG CCC ATG | 181 |
| Arg Asn Ser Ser His Ile Lys Arg Pro Met | |
| 55 60 | |

| AAC GCC TTC ATG GTG TGG GCC AAG GAT GAG | 211 |
| Asn Ala Phe Met Val Trp Ala Lys Asp Glu | |
| 65 70 | |

| CGG AGG AAG ATC CTG CAA GCC TTC CCA GAC | 241 |
| Arg Arg Lys Ile Leu Gln Ala Phe Pro Asp | |
| 75 80 | |

| ATG CAC AAC TCC AGC ATC AGC AAG ATC CTT | 271 |
| Met His Asn Ser Ser Ile Ser Lys Ile Leu | |
| 85 90 | |

| GGA TCT CGC TGG AAG TCC ATG ACC AAC CAG | 301 |
| Gly Ser Arg Trp Lys Ser Met Thr Asn Gln | |
| 95 100 | |

| GAG AAG CAG CCC TAC TAT GAG GAA CAG GCT | 331 |
| Glu Lys Gln Pro Tyr Tyr Glu Glu Gln Ala | |
| 105 110 | |

| CTG CTG ATC GTC ATC ACC TGG AGA AGT ATC | 361 |
| Leu Leu Ile Val Ile Thr Trp Arg Ser Ile | |
| 115 120 | |

| CTG ACT ACA AGT ACA AGC CGC GGC CAA GCG | 391 |
| Leu Thr Thr Ser Thr Ser Arg Gly Gln Ala | |
| 125 130 | |

| CAC CTG CAT CGT GGA GGG CAA GCG GCT GCG | 421 |
| His Leu His Arg Gly Gly Gln Ala Ala Ala | |
| 135 140 | |

| CGT GGG AGA GTA CAA GGC CCT GAT GAG GAC | 451 |
| Arg Gly Arg Val Gln Gly Pro Asp Glu Asp | |
| 145 150 | |

| CCG GCG TCA GGA TGC CCG CCA GAG CTA CGT | 481 |
| Pro Ala Ser Gly Cys Pro Pro Glu Leu Arg | |
| 155 160 | |

| GAT CCC CCC GCA GGC TGG CCA GGT GCA GAT | 511 |
| Asp Pro Pro Ala Gly Trp Pro Gly Ala Asp | |
| 165 170 | |

| GAG CTC CTC AGA TGT CCT GTA CCC TCG GGC | 541 |
| Glu Leu Leu Arg Cys Pro Val Pro Ser Gly | |
| 175 180 | |

```
AGC AGG CAT GCC GCT GCA CAG CCA CTG GTG                        571
Ser Arg His Ala Ala Ala Gln Pro Leu Val
                185                 190

GAG CAC TAT GTC CCT CGT AGC CTG GAC CCC                        601
Glu His Tyr Val Pro Arg Ser Leu Asp Pro
                195                 200

AAC ATG CCT GTG ATC GTC AAC ACC TGC AGC                        631
Asn Met Pro Val Ile Val Asn Thr Cys Ser
                205                 210

CTC AGA GAG GAG GGT GAG GGC ACA GAT GAC                        661
Leu Arg Glu Glu Gly Glu Gly Thr Asp Asp
                215                 220

AGG CAC TCG GTG GCT GAT GGC GAG ATG TAC                        691
Arg His Ser Val Ala Asp Gly Glu Met Tyr
                225                 230

CGG TAC AGC GAG GAC GAG GAC TCG GAG GGT                        721
Arg Tyr Ser Glu Asp Glu Asp Ser Glu Gly
                235                 240

GAA GAG AAG AGC GAT GGG GAG TTG GTG GTG                        751
Glu Glu Lys Ser Asp Gly Glu Leu Val Val
                245                 250

CTC ACA GAC TGATCCCGGC TGGGTGGCCT                              780
Leu Thr Asp

GGCCCCTTCT CCTCTGGGGA AGACCTTGTC CCAACTCGAT                    820

GGGCAAAGCT AGCCAACCTA AGACTATGTT GGTACTTGGA                    860

CTTGTTCGTG CCCCAGAGAT GGGCAAAGCT GTGCACTTGC                    900

AGATACATTC ATGAGGGGAG AGGCTCTCTC CCTTCCTGAG                    940

GAGCTGTTGG CCTGGGTGGG CAGGAACTGC AGTATGGCCA                    980

TGGGCTGAGC AGGCTGAGCA CCCTCAGCCTT TAGGGCTTAT                  1020

GGCCAGGGGA CACTGTATGA CTCTCCTCTC CTGCAGGTGT                   1060

CTATCCACCT GGGGTATGGC ATCTACCGAC CTGTCTCCCT                   1100

GGGGTCACAT GCTTTGTTTC CATTCTTGTC CTGGCTGGAC                   1140

CAGCCACTGT GGGACCAACA CCCCTCCCAC ACTCCCCCAG                   1180

ACTGCTCGTC TATCACCAGG ATCGCTTTGT ACTTTGTGCA                   1220

AAAGGGTCTG GCTGTCCCTT GCTGTTTTCA TCTCTGCCAA                   1260

GCCTATTGTG CCTCTGGCTG CTGTATGTGT GCGCGTGCAC                   1300

GTGTGTGTGT TTCATCTGTT CATTCACTGC ACAAGATATT                   1340

TATTGAGTGC CCACTACGTG CCAGGCACTG TTGCTGAGTT                   1380

CCTGTGGGTG TGTCTCTCGA TGCCACTCCT GCTTCTCTGG                   1420

GGGCCTCTTT CTGTGCTTCT CTTTGTCCCC AAATTGCTAC                   1460

CTCTTTGTCA GTCTGGGTGT CTCAGGTTCT GTGTGTCCTT                   1500

GTGTGCATTT CTGTCTCTCT CTGTCCTCGT CTCTCTGCAA                   1540

GGCCCTCTAT TTCTCTCTTT CTTGGTGTCT                              1570
```

(2) INFORMATION FOR SEQ ID NO: 6:

(i) SEQUENCE CHARACTERISTICS:
        (A) LENGTH: 3243 nucleotides
        (B) TYPE: nucleic acid
        (C) STRANDEDNESS: single
        (D) TOPOLOGY: linear (xi) SEQUENCE DESCRIPTION: SEQ ID NO: 6:

```
CCAGAACCCA AGAGACCAGG AGTGTCGGAG GCTGCCTCTG        40

GAAGCCAGGA GAAGCTGGAC TTCAACCGAA ATTTGAAAGA        80

AGTGGTGCCA GCCATAGAGA AGCTGTTGTC CAGTGACTGG       120

AAGGAGAGGT TTCTAGGAAG GAACTCTATG GAAGCCAAAG       160

ATGTCAAAGG GACCCAAGAG AGCCTAGCAG AGAAGGAGCT       200

CCAGCTTCTG GTCATGATTC ACCAGCTGTC CACCCTGCGG       240

GACCAGCTCC TGACAGCCCA CTCGGAGCAG AAGAACATGG       280

CTGCCATGCT GTTTGAGAAG CAGCAGCAGC AGATGGAGCT       320

TGCCCGGCAG CAGCAGGAGC AGATTGCAAA GCAGCAGCAG       360

CAGCTGATTC AGCAGCAGCA TAAGATCAAC CTCCTTCAGC       400

AGCAGATCCA GCAGGTTAAC ATGCCTTATG TCATGATCCC       440

AGCCTTCCCC CCAAGCCACC AACCTCTGCC TGTCACCCCT       480

GACTCCCAGC TGGCCTTACC CATTCAGCCC ATTCCCTGCA       520

AACCAGTGGA GTATCCGCTG CAGCTGCTGC ACAGCCCCCC       560

TGCCCCAGTG GTGAAGAGGC CTGGGGCATG GCACCCACCA       600

CCCCCTGCAG GAGCCCTCCC AGCCCCTGAA CCTCACAGCC       640

AAGCCCAAGG CCCCCGAGCT GCCCAACACC TCCAGCTCCC       680
```

| | | |
|---|---|---|
| CAAGCCTGAA G ATG AGC AGC TGT GTG CCC CGC CCC | | 715 |
|  Met Ser Ser Cys Val Pro Arg Pro | | |
|  5 | | |
| CCC AGC CAT GGA GGC CCC ACG CGG GAC CTG | | 745 |
| Pro Ser His Gly Gly Pro Thr Arg Asp Leu | | |
| 10  15 | | |
| CAG TCC AGC CCC CCG AGC CTG CCT CTG GGC | | 775 |
| Gln Ser Ser Pro Pro Ser Leu Pro Leu Gly | | |
| 20  25 | | |
| TTC CTT GGT GAA GGG GAC GCT GTC ACC AAA | | 805 |
| Phe Leu Gly Glu Gly Asp Ala Val Thr Lys | | |
| 30  35 | | |
| GCC ATC CAG GAT GCT CGG CAG CTG CTG CAC | | 835 |
| Ala Ile Gln Asp Ala Arg Gln Leu Leu His | | |
| 40  45 | | |
| AGC CAC AGT GGG GCC TTG GAT GGC TCC CCC | | 865 |
| Ser His Ser Gly Ala Leu Asp Gly Ser Pro | | |
| 50  55 | | |
| AAC ACC CCC TTC CGT AAG GAC CTC ATC AGC | | 895 |
| Asn Thr Pro Phe Arg Lys Asp Leu Ile Ser | | |
| 60  65 | | |
| CTG GAC TCA TCC CCA GCC AAG GAG CGG CTG | | 925 |
| Leu Asp Ser Ser Pro Ala Lys Glu Arg Leu | | |
| 70  75 | | |
| GAG GAC GGC TGT GTG CAC CCA CTG GAG GAA | | 955 |
| Glu Asp Gly Cys Val His Pro Leu Glu Glu | | |
| 80  85 | | |
| GCC ATG CTG AGC TGC GAC ATG GAT GGC TCC | | 985 |
| Ala Met Leu Ser Cys Asp Met Asp Gly Ser | | |
| 90  95 | | |
| CGC CAC TTC CCC GAG TCC CGA AAC AGC AGC | | 1015 |
| Arg His Phe Pro Glu Ser Arg Asn Ser Ser | | |
| 100  105 | | |

```
CAC ATC AAG AGG CCC ATG AAC GCC TTC ATG                            1045
His Ile Lys Arg Pro Met Asn Ala Phe Met
    110                 115

GTG TGG GCC AAG GAT GAG CGG AGG AAG ATC                            1075
Val Trp Ala Lys Asp Glu Arg Arg Lys Ile
    120                 125

CTG CAA GCC TTC CCA GAC ATG CAC AAC TCC                            1105
Leu Gln Ala Phe Pro Asp Met His Asn Ser
    130                 135

AGC ATC AGC AAG ATC CTT GGA TCT CGC TGG                            1135
Ser Ile Ser Lys Ile Leu Gly Ser Arg Trp
    140                 145

AAG TCC ATG ACC AAC CAG GAG AAG CAG CCC                            1165
Lys Ser Met Thr Asn Gln Glu Lys Gln Pro
    150                 155

TAC TAT GAG GAA CAG GCG CGG CTG AGC CGG                            1195
Tyr Tyr Glu Glu Gln Ala Arg Leu Ser Lys
    160                 165

CAG CAC CTG GAG AAG TAT CCT GAC TAC AAG                            1225
Gln His Leu Glu Lys Tyr Pro Asp Tyr Lys
    170                 175

TAC AAG CCG CGG CCC AAG CGC ACC TGC ATC                            1255
Tyr Lys Pro Arg Pro Lys Arg Thr Cys Ile
    180                 185

GTG GAG GGC AAG CGG CTG CGC GTG GGA GAG                            1285
Val Glu Gly Lys Arg Leu Arg Val Gly Glu
    190                 195

TAC AAG GCC CTG ATG AGG ACC CGG CGT CAG                            1315
Tyr Lys Ala Leu Met Arg Thr Arg Arg Gln
    200                 205

GAT GCC CGC CAG AGC TAC GTG ATC CCC CCG                            1345
Asp Ala Arg Gln Ser Tyr Val Ile Pro Pro
    210                 215

CAG GCT GGC CAG GTG CAG ATG AGC TCC TCA                            1375
Gln Ala Gly Gln Val Gln Met Ser Ser Ser
    220                 225

GAT GTC CTG TAC CCT CGG GCA GCA GGC ATG                            1405
Asp Val Leu Tyr Pro Arg Ala Ala Gly Met
    230                 235

CCG CTG GCA CAG CCA CTG GTG GAG CAC TAT                            1435
Pro Leu Ala Gln Pro Leu Val Glu His Tyr
    240                 245

GTC CCT CGT AGC CTG GAC CCC AAC ATG CCT                            1465
Val Pro Arg Ser Leu Asp Pro Asn Met Pro
    250                 255

GTG ATC GTC AAC ACC TGC AGC CTC AGA GAG                            1495
Val Ile Val Asn Thr Cys Ser Leu Arg Glu
    260                 265

GAG GGT GAG GGC ACA GAT GAC AGG CAC TCG                            1525
Glu Gly Glu Gly Thr Asp Asp Arg His Ser
    270                 275

GTG GCT GAT GGC GAG ATG TAC CGG TAC AGC                            1555
Val Ala Asp Gly Glu Met Tyr Arg Tyr Ser
    280                 285

GAG GAC GAG GAC TCG GAG GGT GAA GAG AAG                            1585
Glu Asp Glu Asp Ser Glu Gly Glu Glu Lys
    290                 295

AGC GAT GGG GAG TTG GTG GTG CTC ACA GAC                            1615
Ser Asp Gly Glu Leu Val Val Leu Thr Asp
    300                 305
```

```
TGATCCCGGC TGGGTGGGCC TGGCCCCTTC TCCTCTGGGG          1655

AAGACCTTGT CCCAACTCGA TGGGCACAGC CAGCCAACCT          1695

AAGACTATGT TGGTACTTGG ACTTGTTCGT GCCCCAGAGA          1735

TGGGCAAAGC TGTGCACTTG CAGATACATT CATGAGGGGA          1775

GAGGCGCCCT CCCTTCCTGA GGAGCTGTTG GCCTGGGTGG          1815

GCAGGAACTG CAGTATGGCC ATGGGCTGAG CAGGCTGAGC          1855

ACCTCAGCCT TTAGGGCTTA TGGCCAGGGG ACACTGTATG          1895

ACTCTCCTCT CCTGCAGGTG TCTATCCACC TGGGGTATGG          1935

CATCTACCGA CCTGTCTCCC TGGGGTCACA TGCTTTGTTT          1975

CCATTCTTGT CCTGGCTGGA CCAGCCACTG TGGGACCAAC          2015

ACCCCTCCCA CACTCCCCCA GACTGCTCGT CTATCACCAG          2055

GATCGCTTTG TACTTTGTGC AAAAGGGTCT GGCTGTCCCT          2095

TGCTGTTTTC ATCTCTGCCA AGCCTATTGT GCCTCTGGCT          2135

GCTGTATGTG TGCGCGTGCA CGTGTGTGTG TTTCATCTGT          2175

TCATTCACTG CACAAGATAT TTATTGAGTG CCCACTACGT          2215

GCCAGGCACT GTTGCTGAGT TCCTGTGGGT GTGTCTCTCG          2255

ATGCCACTCC TGCTTCTCTG GGGGCCTCTT TCTGTGCTTC          2295

TCTTTGTCCC CAAATTGCTA CCTCTTTGTC AGTCTGGGTG          2335

TCTCAGGTTC TGTGTGTCCT TGTGTGCATT TCTGTCTCTC          2375

TCTGTCCTCG TCTCTCTGCA AGGCCCTCTA TTTCTCTCTT          2415

TCTTGGTGTC TGTCCTTTGC CCCCTGTGCC CTCTGGATTC          2455

TCTGGGTCTA TGTAGGCCCC TGGTCTGCCC TGGGCTCATC          2495

AGCCTTCCTG ACCTCCTCCT GCCCTCCCCT TCACTCCCTC          2535

CCTGGCTCTG CCAGTCGGTT CCCACGGAGC CATTTTTAGC          2575

TCTGATCAGC ATGGGAATGT GCCTCGGCCT CCAAGGGGCT          2615

TTGTCCTGGT GCCCCCGCCC CTGGTCCCAA CCTGATCCCA          2655

CGAGGGAGTT GGGACAGGAG GATTGATGGT GCTCCCCTTC          2695

CTGCCAGCGT CAGAGGCCCT GGAGAGGGGC TGTCCATGGC          2735

AGCTGGTCTT TATTCCTCCC TCATGAGCAC AGGGTCGGGG          2775

GGGTCCCCAT TCTTGGAAGA GGTTGAGAAG ACTCCTGGGC          2815

TTCAGCCTCT CCCACCCAGC CCTGCCCCCT CACCTGCCTG          2855

CCCTCCCCTC CCCCCACTCT ATACTAGGGA CTGGATCTCA          2895

GCTCTGATCA GTTTCACAAA GTTTGTTCCC TAAGGAAATC          2935

AAATCCCATT GTCACCTAAC TCTGAAGATC TAAATAGCCC          2975

TTGGATCAGT ACGGGAACCC CAAATCCCAC AGGGCCAGAT          3015

GTGGAGTCTG TGTCTGCCCC CGTCTTCTCT CCATCCTCAA          3055

AGCCCCCACT TCTCTCCAGG CTGTTTCTTT TTTTATGACT          3095

GTAAACATAG ATAGTGCTTT ATTTTGTTAA TAATAAGATA          3135

ATGATGAGTA ACTTAACCAG CACATTTCTC CTGTTTACAC          3175
```

```
          TCGGGGGATT TTTTTGTTTT CTGATGACAT AATAAAGACA           3215

GATCATTTCA GAAAAAAAAA AAAAAAAA                        3243

(2) INFORMATION FOR SEQ ID NO: 7:

(i) SEQUENCE CHARACTERISTICS:
         (A) LENGTH: 2599 nucleotides
         (B) TYPE:  nucleic acid
         (C) STRANDEDNESS: single
         (D) TOPOLOGY:  linear (xi) SEQUENCE DESCRIPTION: SEQ ID NO: 7:

GCTGCCTTCA GTCCCTAGTG TCTGGGTCCC CGCCCTCCAG            40

CCGCCTTTGA GTCGTGCCTG GGTCCTCGCC CTTGCCTCAG            80

AACCGCGAAG AAAGGAAGCT CGCGTGTTTG CTAGAAAACC           120

TAGTTGGGAG TGCGAGGCAG AGAACGTTCA GCACCTTTGT           160

TCCTCCCGAA CCCTCGGGAC AGAGGCAGGG TTCTGAGGGC           200

AGGGATTCCC CCTCGTCTTG GCCCCACCGC CCGGGCTGGG           240

CACTAAACTC GGGCCGCGGC GGGGCGAGCG AGGCGGGCTC           280

CGGAGGGAGC TGACGCCTG ATG ATG GCG CAG TCC              314
                              Met Met Ala Gln Ser
                                             5

AAC ATG TTT ACC GTG GCT GAT GTG TTG AGT               344
          Asn Met Phe Thr Val Ala Asp Val Leu Ser
                   10                        15

CAA GAT GAA CTG CGC AAA AAG CTA TAC CAG               374
          Gln Asp Glu Leu Arg Lys Lys Leu Tyr Gln
                       20                        25

ACG TTT AAG GAT CGG GGT ATA CTG GAT ACA               404
          Thr Phe Lys Asp Arg Gly Ile Leu Asp Thr
                   30                        35

CTC AAG ACA CAA CTT CGA AAC CAG CTA ATT               434
          Leu Lys Thr Gln Leu Arg Asn Gln Leu Ile
                       40                        45

CAT GAG TTG ATG CAC CCT GTA TTG AGT GGA               464
          His Glu Leu Met His Pro Val Leu Ser Gly
                   50                        55

GAA CTG CAG CCT CGG TCC ATT TCA GTA GAA               494
          Glu Leu Gln Pro Arg Ser Ile Ser Val Glu
                       60                        65

GGG AGC TCC CTC TTA ATA GGC GCC TCT AAC               524
          Gly Ser Ser Leu Leu Ile Gly Ala Ser Asn
                   70                        75

TCT TTA GTG GCA GAT CAC TTA CAA AGA TGT               554
          Ser Leu Val Ala Asp His Leu Gln Arg Cys
                       80                        85

GGC TAT GAA TAT TCA CTT TCT GTT TTC TTT               584
          Gly Tyr Glu Tyr Ser Leu Ser Val Phe Phe
                   90                        95

CCA GAA AGT GGT TTG GCA AAA GAA AAG GTA               614
          Pro Glu Ser Gly Leu Ala Lys Glu Lys Val
                      100                       105

TTT ACT ATG CAG GAT CTA TTA CAA CTC ATT               644
          Phe Thr Met Gln Asp Leu Leu Gln Leu Ile
                  110                       115

AAA ATC AAC CCT ACT TCC AGT CTC TAC AAA               674
          Lys Ile Asn Pro Thr Ser Ser Leu Tyr Lys
                      120                       125
```

```
TCA CTG GTT TCA GGA TCT GAT AAA GAA AAT                         704
Ser Leu Val Ser Gly Ser Asp Lys Glu Asn
            130                 135

CAA AAA GGT TTT CTT ATG CAT TTT TTA AAA                         734
Gln Lys Gly Phe Leu Met His Phe Leu Lys
            140                 145

GAA TTG GCA GAA TAT CAT CAA GCT AAA GAG                         764
Glu Leu Ala Glu Tyr His Gln Ala Lys Glu
            150                 155

AGT TGT AAT ATG GAA ACT CAG ACA AGT TCG                         794
Ser Cys Asn Met Glu Thr Gln Thr Ser Ser
            160                 165

ACA TTT AAC AGA GAT TCT CTG GCT GAG AAG                         824
Thr Phe Asn Arg Asp Ser Leu Ala Glu Lys
            170                 175

CTT CAG CTT ATT GAT GAT CAG TTT GCA GAT                         854
Leu Gln Leu Ile Asp Asp Gln Phe Ala Asp
            180                 185

GCT TAC CCT CAG CGT ATC AAG TTC GAA TCT                         884
Ala Tyr Pro Gln Arg Ile Lys Phe Glu Ser
            190                 195

TTA GAA ATA AAG CTA AAT GTG TAT AAG AGA                         914
Leu Glu Ile Lys Leu Asn Val Tyr Lys Arg
            200                 205

GAA ATA GAA GAG CAA CTT CGG GCA GAA ATG                         944
Glu Ile Glu Glu Gln Leu Arg Ala Glu Met
            210                 215

TGT CAA AAG TTG AAG TTT TTT AAA GAT ACC                         974
Cys Gln Lys Leu Lys Phe Phe Lys Asp Thr
            220                 225

GAG ATA GCA AAA ATT AAA ATG GAA GCA AAA                        1004
Glu Ile Ala Lys Ile Lys Met Glu Ala Lys
            230                 235

AAA AAG TAT GAA AAG GAG TTA ACC ATG TTC                        1034
Lys Lys Tyr Glu Lys Glu Leu Thr Met Phe
            240                 245

CAG AAT GAT TTT GAA AAA GCT TGT CAA GCA                        1064
Gln Asn Asp Phe Glu Lys Ala Cys Gln Ala
            250                 255

AAA TCT GAA GCT CTC GTT CTT CGG GAA AAG                        1094
Lys Ser Glu Ala Leu Val Leu Arg Glu Lys
            260                 265

AGT ACC CTT GAA AGA ATT CAC AAG CAC CAA                        1124
Ser Thr Leu Glu Arg Ile His Lys His Gln
            270                 275

GAG ATT GAA ACA AAA GAA ATT TAT GCT CAA                        1154
Glu Ile Glu Thr Lys Glu Ile Tyr Ala Gln
            280                 285

AGG CAA CTT TTA CTA AAA GAT ATG GAT TTG                        1184
Arg Gln Leu Leu Leu Lys Asp Met Asp Leu
            290                 295

CTA AGA GGA AGA GAA GCA GAG CTG AAG CAA                        1214
Leu Arg Gly Arg Glu Ala Glu Leu Lys Gln
            300                 305

AGA GTT GAA GCT TTT GAA TTG AAC CAG AAG                        1244
Arg Val Glu Ala Phe Glu Leu Asn Gln Lys
            310                 315

CTC CAG GAA GAA AAA CAT AAA AGC ATA ACT                        1274
Leu Gln Glu Glu Lys His Lys Ser Ile Thr
            320                 325
```

```
GAG GCA CTT AGG AGA CAG GAG CAG AAT ATA                         1304
Glu Ala Leu Arg Arg Gln Glu Gln Asn Ile
            330                 335

AAG AGT TTT GAG GAG ACC TAT GAC CGA AAG                         1334
Lys Ser Phe Glu Glu Thr Tyr Asp Arg Lys
            340                 345

CTC AAG AAT GAA CTT CTA AAG TAT CAA CTT                         1364
Leu Lys Asn Glu Leu Leu Lys Tyr Gln Leu
            350                 355

GAA CTG AAG GAT GAC TAC ATC ATT AGA ACT                         1394
Glu Leu Lys Asp Asp Tyr Ile Ile Arg Thr
            360                 365

AAT CGA CTG ATT GAA GAT GAA AGG AAG AAT                         1424
Asn Arg Leu Ile Glu Asp Glu Arg Lys Asn
            370                 375

AAA GAA AAA GCT GTT CAT TTG CAA GAG GAG                         1454
Lys Glu Lys Ala Val His Leu Gln Glu Glu
            380                 385

CTC ATA GCT ATT AAT TCA AAA AAG GAG GAA                         1484
Leu Ile Ala Ile Asn Ser Lys Lys Glu Glu
            390                 395

CTC AAT CAA TCT GTA AAT CGT GTG AAA GAA                         1514
Leu Asn Gln Ser Val Asn Arg Val Lys Glu
            400                 405

CTT GAG CTT GAA TTA GAG TCT GTC AAA GCC                         1544
Leu Glu Leu Glu Leu Glu Ser Val Lys Ala
            410                 415

CAG TCT TTG GCA ATA ACA AAA CAA AAC CAT                         1574
Gln Ser Leu Ala Ile Thr Lys Gln Asn His
            420                 425

ATG CTG AAT GAA AAG GTT AAA GAG ATG AGT                         1604
Met Leu Asn Glu Lys Val Lys Glu Met Ser
            430                 435

GAT TAT TCA CTA CTA AAA GAA GAG AAA CTG                         1634
Asp Tyr Ser Leu Leu Lys Glu Glu Lys Leu
            440                 445

GAG CTT CTG GCA CAA AAT AAA TTA CTT AAA                         1664
Glu Leu Leu Ala Gln Asn Lys Leu Leu Lys
            450                 455

CAA CAA CTG GAA GAG AGT AGA AAT GAA AAC                         1694
Gln Gln Leu Glu Glu Ser Arg Asn Glu Asn
            460                 465

CTG CGT CTC CTA AAC CGC CTA GCT CAG CCG                         1724
Leu Arg Leu Leu Asn Arg Leu Ala Gln Pro
            470                 475

GCT CCT GAA CTT GCA GTC TTT CAG AAA GAA                         1754
Ala Pro Glu Leu Ala Val Phe Gln Lys Glu
            480                 485

CTA CGG AAA GCC GAA AAG GCT ATA GTG GTT                         1784
Leu Arg Lys Ala Glu Lys Ala Ile Val Val
            490                 495

GAG CAT GAG GAG TTC GAA AGC TGC AGG CAA                         1814
Glu His Glu Glu Phe Glu Ser Cys Arg Gln
            500                 505

GCT CTG CAC AAA CAA CTG CAA GAC GAA ATT                         1844
Ala Leu His Lys Gln Leu Gln Asp Glu Ile
            510                 515

GAG CAT TCT GCA CAG CTG AAG GCC CAG ATT                         1874
Glu His Ser Ala Gln Leu Lys Ala Gln Ile
            520                 525
```

```
CTA GGT TAC AAA GCT TCT GTA AAG AGT TTA                              1904
Leu Gly Tyr Lys Ala Ser Val Lys Ser Leu
                530                 535

ACT ACT CAG GTT GCC GAT TTA AAA TTG CAA                              1934
Thr Thr Gln Val Ala Asp Leu Lys Leu Gln
                540                 545

CTG AAG CAA ACT CAG ACA GCC CTA GAG AAT                              1964
Leu Lys Gln Thr Gln Thr Ala Leu Glu Asn
                550                 555

GAA GTG TAC TGC AAT CCA AAG CAG TCT GTG                              1994
Glu Val Tyr Cys Asn Pro Lys Gln Ser Val
                560                 565

ATC GAT CGT TCT GTC AAT GGA TTA ATA AAT                              2024
Ile Asp Arg Ser Val Asn Gly Leu Ile Asn
                570                 575

GGC AAT GTG GTG CCT TGC AAT GGT GAG ATA                              2054
Gly Asn Val Val Pro Cys Asn Gly Glu Ile
                580                 585

AGT GGG GAT TTC TTG AAC AAT CCT TTT AAA                              2084
Ser Gly Asp Phe Leu Asn Asn Pro Phe Lys
                590                 595

CAG GAA AAC GTT CTA GCA CGT ATG GTT GCA                              2114
Gln Glu Asn Val Leu Ala Arg Met Val Ala
                600                 605

TCA AGG ATC ACA AAT TAT CCA ACT GCA TGG                              2144
Ser Arg Ile Thr Asn Tyr Pro Thr Ala Trp
                610                 615

GTG GAG GGT AGT TCC CCT GAT TCT GAC CTT                              2174
Val Glu Gly Ser Ser Pro Asp Ser Asp Leu
                620                 625

AAT ACT AAG GCA AGG GTC AAA GAG CTT CAG                              2204
Asn Thr Lys Ala Arg Val Lys Glu Leu Gln
                630                 635

CAA GAG GCC GAA CGC TTG GAA AAG GCT TTC                              2234
Gln Glu Ala Glu Arg Leu Glu Lys Ala Phe
                640                 645

AGA AGT TAC CAT CGG AGA GTC ATT AAA AAC                              2264
Arg Ser Tyr His Arg Arg Val Ile Lys Asn
                650                 655

TCT GCC AAA AGC CCA CTA GCA GCA AAG AGC                              2294
Ser Ala Lys Ser Pro Leu Ala Ala Lys Ser
                660                 665

CCA CCT CTC TGC ACT TGC TGG AAG CCT TCA                              2324
Pro Pro Leu Cys Thr Cys Trp Lys Pro Ser
                670                 675

AAA ACA TTA CTT CCA GTT CCC CGG AAA GAC                              2354
Lys Thr Leu Leu Pro Val Pro Arg Lys Asp
                680                 685

ATA TTT TTG GAG AGG ACA GAG TTG TCT CTG                              2384
Ile Phe Leu Glu Arg Thr Glu Leu Ser Leu
                690                 695

AGC AGC CTC AAG TGG GCA CAC TTG AAG AAA                              2414
Ser Ser Leu Lys Trp Ala His Leu Lys Lys
                700                 705

GGA ATG ACG TCG TGG AAG CAC TGACAGGCAG                               2445
Gly Met Thr Ser Trp Lys His
                710

TGCAGCCTCG AGGCTCCGCG GGGGCACTTC CTCCAGACGC                          2485

CTCTCTTCCA CACCCCTTCC AAAAGCAAAA AGAAGCCTCG                          2525
```

```
            AAAGTGAAAT GTATCTGGAA GGTCTGGGCA GATCACACAT              2565

TGCTTCCCCC AGTCCTTGTC CTGACAGAAT GCCC                    2599
```

(2) INFORMATION FOR SEQ ID NO: 8:

(i) SEQUENCE CHARACTERISTICS:
        (A) LENGTH: 346 nucleotides
        (B) TYPE: nucleic acid
        (C) STRANDEDNESS: single
        (D) TOPOLOGY: linear (xi) SEQUENCE DESCRIPTION: SEQ ID NO: 8:

```
            TCGACCTTCG CCTTCAATGG GCTGGCCAGT GGGGGAGAAC               40

CGGGGAGGTC GGGGAAGAAT CGCTTCCACT CGGAGTGGGG               80

GGGCGGCTCA CTCCAGGCGA TACAGGCACA GGCAAAGGAG              120

GGAAGCAAAC AAGGACATAC ATCCTGTGCT CATACAGCCA              160

TGCACCATGT ATGGGGTTTG TCACATCACT CGTACGCCCC              200

CACAAGCCTG GAGATAGAAC ATACCTGACT CTAAACCCAA              240

GACCTCTAAC CACCTTATGG CGCTTTCCTG GGAGACCCAA              280

TGAGGGAATG ACATTTAAAG CCCTCCCTAG ACCAGAGTTC              320

TCAGGGTACT TTTCTATTAA AAAAAA                             346
```

(2) INFORMATION FOR SEQ ID NO: 9:

(i) SEQUENCE CHARACTERISTICS:
        (A) LENGTH: 1413 nucleotides
        (B) TYPE: nucleic acid
        (C) STRANDEDNESS: single
        (D) TOPOLOGY: linear (xi) SEQUENCE DESCRIPTION: SEQ ID NO: 9:

```
            TC AAC CGG GCA GAG GGT CCA CCG GAG CCT TCA                32
               Asn Arg Ala Glu Gly Pro Pro Glu Pro Ser
                                  5                  10

CGG GTG AGC AGT GTG TCC TCC CAG TTC AGC                   62
            Arg Val Ser Ser Val Ser Ser Gln Phe Ser
                         15                  20

GAC GCA GCC CAG GCC AGC CCC AGC TCC CAC                   92
            Asp Ala Ala Gln Ala Ser Pro Ser Ser His
                         25                  30

AGC AGC ACC CCG TCC TGG TGC GAG GAG CCG                  122
            Ser Ser Thr Pro Ser Trp Cys Glu Glu Pro
                         35                  40

GCC CAA GCC AAC ATG GAC ATC TCC ACG GGA                  152
            Ala Gln Ala Asn Met Asp Ile Ser Thr Gly
                         45                  50

CAC ATG ATT CTG GCA TAC ATG GAG GAT CAC                  182
            His Met Ile Leu Ala Tyr Met Glu Asp His
                         55                  60

CTG CGG AAC CGG GAC CGC CTT GCC AAG GAG                  212
            Leu Arg Asn Arg Asp Arg Leu Ala Lys Glu
                         65                  70

TGG CAG GCC CTC TGT GCC TAC CAA GCA GAG                  242
            Trp Gln Ala Leu Cys Ala Tyr Gln Ala Glu
                         75                  80

CCA AAC ACC TGT GCC ACC GCG CAG GGG GAG                  272
            Pro Asn Thr Cys Ala Thr Ala Gln Gly Glu
                         85                  90
```

```
GGC AAC ATC AAA AAG AAC CGG CAT CCT GAC                          302
Gly Asn Ile Lys Lys Asn Arg His Pro Asp
             95                 100

TTC CTG CCC TAT GAC CAT GCC CGC ATA AAA                          332
Phe Leu Pro Tyr Asp His Ala Arg Ile Lys
            105                 110

CTG AAG GTG GAG AGC AGC CCT TCT CGG AGC                          362
Leu Lys Val Glu Ser Ser Pro Ser Arg Ser
            115                 120

GAT TAC ATC AAC GCC AGC CCC ATT ATT GAG                          392
Asp Tyr Ile Asn Ala Ser Pro Ile Ile Glu
            125                 130

CAT GAC CCT CGG ATG CCA GCC TAC ATA GCC                          422
His Asp Pro Arg Met Pro Ala Tyr Ile Ala
            135                 140

ACG CAG GGC CCG CTG TCC CAT ACC ATC GCA                          452
Thr Gln Gly Pro Leu Ser His Thr Ile Ala
            145                 150

GAC TTC TGG CAG ATG GTG TGG GAG AGC GGC                          482
Asp Phe Trp Gln Met Val Trp Glu Ser Gly
            155                 160

TGC ACC GTC ATC GTC ATG CTG ACC CCG CTG                          512
Cys Thr Val Ile Val Met Leu Thr Pro Leu
            165                 170

GTG GAG GAT GGT GTC AAG CAG TGT GAC CGC                          542
Val Glu Asp Gly Val Lys Gln Cys Asp Arg
            175                 180

TAC TGG CCA GAT GAG GGT GCC TCC CTC TAC                          572
Tyr Trp Pro Asp Glu Gly Ala Ser Leu Tyr
            185                 190

CAC GTA TAT GAG GTG AAC CTG GTG TCG GAG                          602
His Val Tyr Glu Val Asn Leu Val Ser Glu
            195                 200

CAC ATC TGG TGC GAG GAC TTT CTG GTG CGG                          632
His Ile Trp Cys Glu Asp Phe Leu Val Arg
            205                 210

AGC TTC TAC CTG AAG AAC GTG CAG ACC CAG                          662
Ser Phe Tyr Leu Lys Asn Val Gln Thr Gln
            215                 220

GAG ACG CGC ACG CTC ACG CAG TTC CAC TTC                          692
Glu Thr Arg Thr Leu Thr Gln Phe His Phe
            225                 230

CTC AGC TGG CCG GCA GAG GGC ACA CCG GCC                          722
Leu Ser Trp Pro Ala Glu Gly Thr Pro Ala
            235                 240

TCC ACG CGG CCC CTG CTG GAC TTC CGC AGG                          752
Ser Thr Arg Pro Leu Leu Asp Phe Arg Arg
            245                 250

AAG GTG AAC AAG TGC TAC CGG GGC CGC TCC                          782
Lys Val Asn Lys Cys Tyr Arg Gly Arg Ser
            255                 260

TGC CCC ATC ATC GTG CAC TGC AGT GAT GGT                          812
Cys Pro Ile Ile Val His Cys Ser Asp Gly
            265                 270

GCG GGG AGG ACC GGC ACC TAC ATC CTC ATC                          842
Ala Gly Arg Thr Gly Thr Tyr Ile Leu Ile
            275                 280

GAC ATG GTC CTG AAC CGC ATG GCA AAA GGA                          872
Asp Met Val Leu Asn Arg Met Ala Lys Gly
            285                 290
```

```
        GTG AAG GAG ATT GACATCGCT GCCACCCTGGA                  904
        Val Lys Glu Ile

GCATGTCCGT GACCAGCGGC CTGGCCTTGT CCGCTCTAAG             944

GACCAGTTTG AATTTGCCCT GACAGCCGTG GCGGAGGAAG             984

TGAATGCCAT CCTCAAGGCC CTGCCCCAGT GAGACCCTGG            1024

GGCCCCTTGG CGGGCAGCCC AGCCTCTGTC CCTCTTTGCC            1064

TGTGTGAGCA TCTCTGTGTA CCCACTCCTC ACTGCCCCAC            1104

CAGCCACCTC TTGGGCATGC TCAGCCCTTC CTAGAAGAGT            1144

CAGGAAGGGA AAGCCAGAAG GGGCACGCCT GCCCAGCCTC            1184

GCATGCCAGA GCCTGGGGCA TCCCAGAGCC CAGAGCATCC            1224

CATGGGGGTG CTGCAGCCAG GAGGAGAGGA AAGGACATGG            1264

GTAGCAATTC TACCCAGAGC CTTCTCCTGC CTACATTCCC            1304

TGGCCTGGCT CTCCTGTAGC TCTCCTGGGG TTCTGGGAGT            1344

TCCCTGAACA TCTGTGTGTG TCCCCCTATG CTCCAGTATG            1384

GAAGAATGGG GTGGAGGGTC GCCACACCC                       1413

(2) INFORMATION FOR SEQ ID NO: 10:

(i) SEQUENCE CHARACTERISTICS:
        (A) LENGTH: 3311 nucleotides
        (B) TYPE:   nucleic acid
        (C) STRANDEDNESS: single
        (D) TOPOLOGY: linear (xi) SEQUENCE DESCRIPTION:  SEQ ID NO: 10:

CTCCAACGCT TACAAGGTGT GCTCCGACAA CTCATGTCCC              40

AAGGATTGTC CTGGCACGAT GACCTCACCC AGTATGTGAT              80

CTCTCAGGAG ATGGAGCGCA TCCCCAGGCT TCGCCCCCCA             120

GAGCCCCGTC CAAGGGACAG GTCTGGCTTG CACCCAAGA              160

GACCTGGTCC TGCTGGAGAG CTGCTTTTAC AGGACATCCC             200

CACTGGCTCC GCCCCTGCTG CCCAGCATCG GCTTCCACAA             240

CCACCAGTGG GCAAAGGTGG AGCTGGGGCC AGCTCCTCTC             280

TGTCCCCTCT GCAGGCTGAG CTGCTCCCGC CTCTCTTGGA             320

GCACCTGCTG CTGCCCCCAC AGCCTCCCCA CCCTTCACTG             360

AGTTACGAAC CTGCCTTGCT GCAGCCCTAC CTGTTCCACC             400

AGTTTGGCTC CCGTGATGGC TCCAGGGTCT CAGAGGGCTC             440

CCCAGGGATG GTCAGTGTCG GCCCCCTGCC CAAGGCTGAA             480

GCCCCTGCCC TCTTCAGCAG AACTGCCTCC AAGGGCATAT             520

TTGGGGACCA CCCTGGCCAC TCCTACGGGG ACCTTCCAGG             560

GCCTTCACCT GCCCAGCTTT TTCAAGACTC TGGGCTGCTC             600

TATCTGGCCC AGGAGTTGCC AGCACCCAGC AGGGCCAGGG             640

TGCCAAGGCT GCCAGAGCAA GGGAGCAGCA GCCGGGCAGA             680

GGACTCCCCA GAGGGCTATG AGAAGGAAGG ACTAGGGGAT             720

CGTGGAGAGA AGCCTGCTTC CCCAGCTGTG CAGCCAGATG             760
```

-continued

```
CGGCTCTGCA GAGGCTGGCC GCTGTGCTGG CGGGCTATGG                    800

GGTAGAGCTG CGTCAGCTGA CCCCTGAGCA GCTCTCCACA                    840

CTCCTGACCC TGCTGCAGCT ACTGCCCAAG GGTGCAGGAA                    880

GAAATCCGGG AGGGGTTGTA AATGTTGGAG CTGATATCAA                    920

GAAAACA ATG GAG GGG CCG GTG GAG GGC                            948
        Met Glu Gly Pro Val Glu Gly
         1               5

AGA GAC ACA GCA GAG CTT CCA GCC CGC ACA                        978
Arg Asp Thr Ala Glu Leu Pro Ala Arg Thr
         10                  15

TCC CCC ATG CCT GGA CAC CCC ACT GCC AGC                        1008
Ser Pro Met Pro Gly His Pro Thr Ala Ser
         20                  25

CCT ACC TCC AGT GAA GTC CAG CAG GTG CCA                        1038
Pro Thr Ser Ser Glu Val Gln Gln Val Pro
         30                  35

AGC CCT GTC TCC TCT GAG CCT CCC AAA GCT                        1068
Ser Pro Val Ser Ser Glu Pro Pro Lys Ala
         40                  45

GCC AGA CCC CCT GTG ACA CCT GTC CTG CTA                        1098
Ala Arg Pro Pro Val Thr Pro Val Leu Leu
         50                  55

GAG AAG AAA AGC CCA CTG GGC CAG AGC CAG                        1128
Glu Lys Lys Ser Pro Leu Gly Gln Ser Gln
         60                  65

CCC ACG GTG GCA GGA CAG CCC TCA GCC CGC                        1158
Pro Thr Val Ala Gly Gln Pro Ser Ala Arg
         70                  75

CCA GCA GCA GAG GAA TAT GGC TAC ATC GTC                        1188
Pro Ala Ala Glu Glu Tyr Gly Tyr Ile Val
         80                  85

ACT GAT CAG AAG CCC CTG AGC CTG GCT GCA                        1218
Thr Asp Gln Lys Pro Leu Ser Leu Ala Ala
         90                  95

GGA GTG AAG CTG CTG GAG ATC CTG GCT GAG                        1248
Gly Val Lys Leu Leu Glu Ile Leu Ala Glu
        100                 105

CAT GTG CAC ATG TCC TCA GGC AGC TTC ATC                        1278
His Val His Met Ser Ser Gly Ser Phe Ile
        110                 115

AAC ATC AGT GTG GTG GGA CCA GCC CTC ACC                        1308
Asn Ile Ser Val Val Gly Pro Ala Leu Thr
        120                 125

TTC CGC ATC CGG CAC AAT GAG CAG AAC CTG                        1338
Phe Arg Ile Arg His Asn Glu Gln asn Leu
        130                 135

TCT TTG GCT GAT GTG ACC CAA CAA GCA GGG                        1368
Ser Leu Ala Asp Val Thr Gln Gln Ala Gly
        140                 145

CTG GTG AAG TCT GAA CTG GAA GCA CAG ACA                        1398
Leu Val Lys Ser Glu Leu Glu Ala Gln Th
        150                 155

GGG CTC CAA ATC TTG CAG ACA GGA GTG GGA                        1428
Gly Leu Gln Ile Leu Gln Thr Gly Val Gly
        160                 165

CAG AGG GAG GAG GCA GCT GCA GTC CTT CCC                        1458
Gln Arg Glu Glu Ala Ala Ala Val Leu Pro
        170                 175
```

```
CAA ACT GCG CAC AGC ACC TCA CCC ATG CGC                     1488
Gln Thr Ala His Ser Thr Ser Pro Met Arg
    180                 185

TCA GTG CTG CTC ACT CTG GTG GCC CTG GCA                     1518
Ser Val Leu Leu Thr Leu Val Ala Leu Ala
    190                 195

GGT GTG GCT GGG CTG CTG GTG GCT CTG GCT                     1548
Gly Val Ala Gly Leu Leu Val Ala Leu Ala
    200                 205

GTG GCT CTG TGT GTG CGG CAG CAT GCG CGG                     1578
Val Ala Leu Cys Val Arg Gln His Ala Arg
    210                 215

CAG CAA GAC AAG GAG CGC CTG GCA GCC CTG                     1608
Gln Gln Asp Lys Glu Arg Leu Ala Ala Leu
    220                 225

GGG CCT GAG GGG GCC CAT GGT GAC ACT ACC                     1638
Gly Pro Glu Gly Ala His Gly Asp Thr Thr
    230                 235

TTT GAG TAC CAG GAC CTG TGC CGC CAG CAC                     1668
Phe Glu Tyr Gln Asp Leu Cys Arg Gln His
    240                 245

ATG GCC ACG AAG TCC TTG TTC AAC CGG GCA                     1698
Met Ala Thr Lys Ser Leu Phe Asn Arg Al
    250                 255

GAG GGT CCA CCG GAG CCT TCA CGG GTG AGC                     1728
Glu Gly Pro Pro Glu Pro Ser Arg Val Ser
    260                 265

AGT GTG TCC TCC CAG TTC AGC GAC GCA GCC                     1758
Ser Val Ser Ser Gln Phe Ser Asp Ala Ala
    270                 275

CAG GCC AGC CCC AGC TCC CAC AGC AGC ACC                     1788
Gln Ala Ser Pro Ser Ser His Ser Ser Thr
    280                 285

CCG TCC TGG TGC GAG GAG CCG GCC CAA GCC                     1818
Pro Ser Trp Cys Glu Glu Pro Ala Gln Ala
    290                 295

AAC ATG GAC ATC TCC ACG GGA CAC ATG ATT                     1848
Asn Met Asp Ile Ser Thr Gly His Met Ile
    300                 305

CTG GCA TAC ATG GAG GAT CAC CTG CGG AAC                     1878
Leu Ala Tyr Met Glu Asp His Leu Arg Asn
    310                 315

CGG GAC CGC CTT GCC AAG GAG TGG CAG GCC                     1908
Arg Asp Arg Leu Ala Lys Glu Trp Gln Ala
    320                 325

CTC TGT GCC TAC CAA GCA GAG CCA AAC ACC                     1938
Leu Cys Ala Tyr Gln Ala Glu Pro Asn Thr
    330                 335

TGT GCC ACC GCG CAG GGG GAG GGC AAC ATC                     1968
Cys Ala Thr Ala Gln Gly Glu Gly Asn Ile
    340                 345

AAA AAG AAC CGG CAT CCT GAC TTC CTG CCC                     1998
Lys Lys Asn Arg His Pro Asp Phe Leu Pr
    350                 355

TAT GAC CAT GCC CGC ATA AAA CTG AAG GTG                     2028
Tyr Asp His Ala Arg Ile Lys Leu Lys Val
    360                 365

GAG AGC AGC CCT TCT CGG AGC GAT TAC ATC                     2058
Glu Ser Ser Pro Ser Arg Ser Asp Tyr Ile
    370                 375
```

| | | |
|---|---|---|
| AAC GCC AGC CCC ATT ATT GAG CAT GAC CCT<br>Asn Ala Ser Pro Ile Ile Glu His Asp Pro<br>380                    385 | | 2088 |
| CGG ATG CCA GCC TAC ATA GCC ACG CAG GGC<br>Arg Met Pro Ala Tyr Ile Ala Thr Gln Gly<br>390                    395 | | 2118 |
| CCG CTG TCC CAT ACC ATC GCA GAC TTC TGG<br>Pro Leu Ser His Thr Ile Ala Asp Phe Trp<br>400                    405 | | 2148 |
| CAG ATG GTG TGG GAG AGC GGC TGC ACC GTC<br>Gln Met Val Trp Glu Ser Gly Cys Thr Val<br>410                    415 | | 2178 |
| ATC GTC ATG CTG ACC CCG CTG GTG GAG GAT<br>Ile Val Met Leu Thr Pro Leu Val Glu Asp<br>420                    425 | | 2208 |
| GGT GTC AAG CAG TGT GAC CGC TAC TGG CCA<br>Gly Val Lys Gln Cys Asp Arg Tyr Trp Pro<br>430                    435 | | 2238 |
| GAT GAG GGT GCC TCC CTC TAC CAC GTA TAT<br>Asp Glu Gly Ala Ser Leu Tyr His Val Tyr<br>440                    445 | | 2268 |
| GAG GTG AAC CTG GTG TCG GAG CAC ATC TGG<br>Glu Val Asn Leu Val Ser Glu His Ile Trp<br>450                    455 | | 2298 |
| TGC GAG GAC TTT CTG GTG CGG AGC TTC TAC<br>Cys Glu Asp Phe Leu Val Arg Ser Phe Tyr<br>460                    465 | | 2328 |
| CTG AAG AAC GTG CAG ACC CAG GAG ACG CGC<br>Leu Lys Asn Val Gln Thr Gln Glu Thr Arg<br>470                    475 | | 2358 |
| ACG CTC ACG CAG TTC CAC TTC CTC AGC TGG<br>Thr Leu Thr Gln Phe His Phe Leu Ser Trp<br>480                    485 | | 2388 |
| CCG GCA GAG GGC ACA CCG GCC TCC ACG CGG<br>Pro Ala Glu Gly Thr Pro Ala Ser Thr Arg<br>490                    495 | | 2418 |
| CCC CTG CTG GAC TTC CGC AGG AAG GTG AAC<br>Pro Leu Leu Asp Phe Arg Arg Lys Val Asn<br>500                    505 | | 2448 |
| AAG TGC TAC CGG GGC CGC TCC TGC CCC ATC<br>Lys Cys Tyr Arg Gly Arg Ser Cys Pro Ile<br>510                    515 | | 2478 |
| ATC GTG CAC TGC AGT GAT GGT GCG GGG AGG<br>Ile Val His Cys Ser Asp Gly Ala Gly Arg<br>520                    525 | | 2508 |
| ACC GGC ACC TAC ATC CTC ATC GAC ATG GTC<br>Thr Gly Thr Tyr Ile Leu Ile Asp Met Val<br>530                    535 | | 2538 |
| CTG AAC CGC ATG GCA AAA GGA GTG AAG GAG<br>Leu Asn Arg Met Ala Lys Gly Val Lys Glu<br>540                    545 | | 2568 |
| ATT GACATCGCTG CCACCCTGGA GCATGTCCGT<br>Ile | | 2601 |
| GACCAGCGGC CTGGCCTTGT CCGCTCTAAG GACCAGTTTG | | 2641 |
| AATTTGCCCT GACAGCCGTG GCGGAGGAAG TGAATGCCAT | | 2681 |
| CCTCAAGGCC CTGCCCCAGT GAGACCCTGG GGCCCCTTGG | | 2721 |
| CGGGCAGCCC AGCCTCTGTC CCTCTTTGCC TGTGTGAGCA | | 2761 |
| TCTCTGTGTA CCCACTCCTC ACTGCCCCAC CAGCCACCTC | | 2801 |

```
        TTGGGCATGC TCAGCCCTTC CTAGAAGAGT CAGGAAGGGA              2841

AAGCCAGAAG GGGCACGCCT GCCCAGCCTC GCATGCCAGA              2881

GCCTGGGGCA TCCCAGAGCC CAGAGCATCC CATGGGGGTG              2921

CTGCAGCCAG GAGGAGAGGA AAGGACATGG GTAGCAATTC              2961

TACCCAGAGC CTTCTCCTGC CTACATTCCC TGGCCTGGCT              3001

CTCCTGTAGC TCTCCTGGGG TTCTGGGAGT TCCCTGAACA              3041

TCTGTGTGTG TCCCCCTATG CTCCAGTATG GAAGAATGGG              3081

GTGGAGGGTC GCCACACCCG GCTCCCCCTG CTTCTCAGCC              3121

CCGGGCCTGC CTCTGACTCA CACTTGGGCG CTCTGCCCTC              3161

CCTGGCCTCA CGCCCAGCCT CCTCCCACCA CCCTCCCACC              3201

ATGCGCTGCT CAACCTCTCT CCTTCTGGCG CAAGAGAACA              3241

TTTCTAGAAA AAACTACTTT TGTACCAGTG TGAATAAAGT              3281

TAGTGTGTTG TCTGTGCAGC TGCAAAAAAA                         3311

(2) INFORMATION FOR SEQ ID NO: 11:

(i) SEQUENCE CHARACTERISTICS:
        (A) LENGTH: 195 amino acids
        (B) TYPE: amino acid
        (D) TOPOLOGY: linear (xi) SEQUENCE DESCRIPTION: SEQ ID NO: 11:

Pro Met Asn Ala Phe Met Val Trp Ala Lys
         1               5                  10

Asp Glu Arg Arg Lys Ile Leu Gln Ala Phe
                        15                  20

Pro Asp Met His Asn Ser Ser Ile Ser Lys
                        25                  30

Ile Leu Gly Ser Arg Trp Lys Ser Met Thr
                        35                  40

Asn Gln Glu Xaa Gln Pro Tyr Tyr Glu Glu
                        45                  50

Gln Ala Leu Leu Ile Val Ile Thr Trp Arg
                        55                  60

Ser Ile Leu Thr Thr Ser Thr Ser Arg Gly
                        65                  70

Gln Ala His Leu His Arg Gly Gly Gln Ala
                        75                  80

Ala Ala Arg Gly Arg Val Gln Gly Pro Asp
                        85                  90

Glu Asp Pro Ala Ser Gly Cys Pro Pro Glu
                        95                 100

Leu Arg Asp Pro Pro Ala Gly Trp Pro Gly
                       105                 110

Ala Asp Glu Leu Leu Arg Cys Pro Val Pro
                       115                 120

Ser Gly Ser Arg His Ala Ala Ala Gln Pro
                       125                 130

Leu Val Glu His Tyr Val Pro Arg Ser Leu
                       135                 140
```

```
        Asp Pro Asn Met Pro Val Ile Val Asn Thr
                        145                 150

Cys Ser Leu Arg Glu Glu Gly Glu Gly Thr
                        155                 160

Asp Asp Arg His Ser Val Ala Asp Gly Glu
                        165                 170

Met Tyr Arg Tyr Ser Glu Asp Glu Asp Ser
                        175                 180

Glu Gly Glu Glu Lys Ser Asp Gly Glu Leu
                        185                 190

Val Val Leu Thr Asp
                        195

(2) INFORMATION FOR SEQ ID NO: 12:

(i) SEQUENCE CHARACTERISTICS:
        (A) LENGTH: 604 amino acids
        (B) TYPE: amino acid
        (D) TOPOLOGY: linear (xi) SEQUENCE DESCRIPTION: SEQ ID NO: 12:

Met Ser Ser Lys Gln
        1               5

Ala Thr Ser Pro Phe Ala Cys Ala Ala Asp
                        10                  15

Gly gln Asp Ala Met Thr Gln Asp Leu Thr
                        20                  25

Ser Arg Glu Lys Glu Gly Ser Asp Gln
                        30                  35

His Val Ala Ser His Leu Pro Leu His Pro
                        40                  45

Ile Met His Asn Leu Pro His Ser Glu Glu
                        50                  55

Leu Pro Thr Leu Val Ser Thr Ile Gln Gln
                        60                  65

Asp Ala Asp Trp Asp Ser Val Leu Ser Ser
                        70                  75

Gln Gln Arg Met Glu Ser Gln Asn Asn Lys
                        80                  85

Leu Cys Ser Leu Tyr Ser Phe Arg Asn Thr
                        90                  95

Ser Thr Ser Pro His Lys Pro Asp Glu Gly
                        100                 105

Ser Arg Asp Arg Glu Ile Met Thr Ser Val
                        110                 115

Thr Phe Gly Thr Pro Glu Arg Arg Lys Gly
                        120                 125

Ser Leu Ala Asp Val Val Asp Thr Leu Lys
                        130                 135

Gln Lys Lys Leu Glu Glu Met Thr Arg Thr
                        140                 145

Glu Gln Glu Asp Ser Ser Cys Met Glu Lys
                        150                 155

Leu Leu Ser Lys Asp Trp Lys Glu Lys Met
                        160                 165
```

-continued

```
Glu Arg Leu Asn Thr Ser Glu Leu Leu Gly
            170                 175

Glu Ile Lys Gly Thr Pro Glu Ser Leu Ala
            180                 185

Glu Lys Glu Arg Gln Leu Ser Thr Met Ile
            190                 195

Thr Gln Leu Ile Ser Leu Arg Glu Gln Leu
            200                 205

Leu Ala Ala His Asp Glu Gln Lys Lys Leu
            210                 215

Ala Ala Ser Gln Ile Glu Lys Gln Arg Gln
            220                 225

Gln Met Asp Leu Ala Arg Gln Gln Gln Glu
            230                 235

Gln Ile Ala Arg Gln Gln Gln Gln Leu Leu
            240                 245

Gln Gln Gln His Lys Ile Asn Leu Leu Gln
            250                 255

Gln Gln Ile Gln Val Gln Gly His Met Pro
            260                 265

Pro Leu Met Ile Pro Ile Phe Pro His Asp
            270                 275

Gln Arg Thr Leu Ala Ala Ala Ala Ala Ala
            280                 285

Gln Gln Gly Phe Leu Phe Pro Pro Gly Ile
            290                 295

Thr Tyr Lys Pro Gly Asp Asn Tyr Pro Val
            300                 305

Gln Phe Ile Pro Ser Thr Met Ala Ala Ala
            310                 315

Ala Ala Ser Gly Leu Ser Pro Leu Gln Leu
            320                 325

Gln Lys Gly His Val Ser His Pro Gln Ile
            330                 335

Asn Gln Arg Leu Lys Gly Leu Ser Asp Arg
            340                 345

Phe Gly Arg Asn Leu Asp Thr Phe Glu His
            350                 355

Gly Gly Gly His Ser Tyr Asn His Lys Gln
            360                 365

Ile Glu Gln Leu Tyr Ala Ala Gln Leu Ala
            370                 375

Ser Met Gln Val Ser Pro Gly Ala Lys Met
            380                 385

Pro Ser Thr Pro Gln Pro Pro Asn Thr Ala
            390                 395

Gly Thr Val Ser Pro Thr Gly Ile Lys Asn
            400                 405

Glu Lys Arg Gly Thr Ser Pro Val Thr Gln
            410                 415

Val Lys Asp Glu Ala Ala Ala Gln Pro Leu
            420                 425

Asn Leu Ser Ser Arg Pro Lys Thr Ala Glu
            430                 435
```

```
       Pro Val Lys Ser Pro Thr Ser Pro Thr Gln
                   440                 445

Asn Leu Phe Pro Ala Ser Lys Thr Ser Pro
                   450                 455

Val Asn Leu Pro Asn Lys Ser Ser Ile Pro
                   460                 465

Ser Pro Ile Gly Gly Ser Leu Gly Arg Gly
                   470                 475

Ser Ser Leu Asp Ile Leu Ser Ser Leu Asn
                   480                 485

Ser Pro Ala Leu Phe Gly Asp Gln Asp Thr
                   490                 495

Val Met Lys Ala Ile Gln Glu Ala Arg Lys
                   500                 505

Met Arg Glu Gln Ile Gln Arg Glu Gln Gln
                   510                 515

Gln Gln Gln Pro His Gly Val Asp Gly Lys
                   520                 525

Lys Ser Ser Ile Asn Asn Met Gly Leu Asn
                   530                 535

Ser Cys Arg Asn Glu Lys Glu Arg Thr Arg
                   540                 545

Phe Glu Asn Leu Xaa Pro Gln Leu Thr Gly
                   550                 555

Lys Ser Asn Glu Asp Gly Lys Leu Gly Pro
                   560                 565

Gly Val Ile Asp Leu Thr Arg Pro Glu Asp
                   570                 575

Ala Glu Gly Gly Ala Thr Val Ala Glu Ala
                   580                 585

Arg Val Tyr Arg Asp Ala Arg Gly Leu Pro
                   590                 595

Ala Ala Ser His Thr Leu Ser Asp Gln
                   600

(2) INFORMATION FOR SEQ ID NO: 13:

(i) SEQUENCE CHARACTERISTICS:
       (A) LENGTH: 191 amino acids
       (B) TYPE: amino acid
       (D) TOPOLOGY: linear (xi) SEQUENCE DESCRIPTION: SEQ ID NO: 13:

Ile Glu Lys Leu Lys Leu Glu Ile Glu Lys
       1               5                   10

Leu Lys Ala Glu Ser Gly Asn Pro Ser Ile
                       15                  20

Arg Gln Lys Ile Arg Leu Asp Lys Ala
                       25                  30

Ala Asp Ala Lys Lys Ile Gln Asp Leu Glu
                       35                  40

Arg Gln Val Lys Glu Met Glu Gly Ile Leu
                       45                  50

Lys Arg Arg Tyr Pro Asn Ser Leu Pro Ala
                       55                  60
```

-continued

```
        Leu Ile Leu Ala Ala Ser Ala Ala Gly Asp
                         65                  70

Thr Val Asp Lys Asn Thr Val Glu Phe Met
                         75                  80

Glu Lys Arg Ile Lys Lys Leu Glu Ala Asp
                         85                  90

Leu Glu Gly Lys Asp Glu Asp Ala Lys Lys
                         95                 100

Ser Leu Arg Thr Met Glu Gln Gln Phe Gln
                        105                 110

Lys Met Lys Ile Gln Tyr Glu Gln Arg Leu
                        115                 120

Glu Gln Gln Glu Gln Leu Leu Ala Cys Lys
                        125                 130

Leu Asn Gln His Asp Ser Pro Arg Ile Lys
                        135                 140

Ala Leu Glu Lys Glu Leu Asp Asp Ile Lys
                        145                 150

Glu Ala His Gln Ile Thr Val Arg Asn Leu
                        155                 160

Glu Ala Glu Ile Asp Val Leu Lys His Gln
                        165                 170

Asn Ala Glu Leu Asp Val Lys Lys Asn Asp
                        175                 180

Lys Asp Asp Glu Asp Phe Gln Ser Ile Glu
                        185                 190

Phe (2) INFORMATION FOR SEQ ID NO: 14:

(i) SEQUENCE CHARACTERISTICS:
        (A) LENGTH: 264 amino acids
        (B) TYPE: amino acid
        (D) TOPOLOGY:  linear (xi) SEQUENCE DESCRIPTION:  SEQ ID NO: 14:

Asp Thr Pro Cys Val Lys Val Gly Asp Glu
        1                 5                  10

Val Glu Val Met Val Val Glu Lys Glu Asp
                         15                  20

Arg Asn Gly Asn Leu Asn Leu Ser Arg Lys
                         25                  30

Ser Ala Arg Ile Phe Arg Ala Trp Glu Arg
                         35                  40

Ile Met Glu Val His Lys Thr Gly Glu Val
                         45                  50

Val Thr Gly Leu Val Thr Ser Lys Thr Lys
                         55                  60

Gly Gly Leu Ile Val Asp Val Phe Gly Met
                         65                  70

Glu Thr Phe Leu Pro Gly Ser Gln Ile Asp
                         75                  80

Val Lys Pro Val Thr Asp Tyr Asp Gln Phe
                         85                  90

Val Gly Lys Thr Met Glu Phe Lys Val Val
                         95                 100
```

```
          Lys Ile Asn Glu Thr Ile Lys Asn Ala Val
                          105                 110

Val Ser His Lys Ala Leu Ile Glu Ser Asp
                          115                 120

Ile Glu Ala Gln Arg Ala Glu Ile Met Ser
                          125                 130

Lys Leu Glu Lys Gly Gln Val Leu Glu Gly
                          135                 140

Thr Val Lys Asn Ile Thr Asp Phe Gly Ala
                          145                 150

Phe Met Asp Leu Gly Gly Leu Asp Gly Leu
                          155                 160

Leu Tyr Ile Thr Asp Ile Ser Trp Gly Arg
                          165                 170

Ile Ser His Pro Ser Glu Val Leu Lys Met
                          175                 180

Asp Gln Lys Leu Asn Val Val Val Leu Asp
                          185                 190

Phe Asp Asp Asp Lys Lys Arg Ile Ser Leu
                          195                 200

Gly Leu Lys Gln Leu Thr Pro His Pro Trp
                          205                 210

Glu Val Leu Pro Glu Gly Leu Ala Glu Gly
                          215                 220

Ala Ile Val Lys Gly Lys Val Val Asn Ile
                          225                 230

Glu Asp Tyr Gly Ala Phe Leu Glu Ile Gln
                          235                 240

Pro Gly Val Glu Gly Leu Val His Val Ser
                          245                 250

Glu Ile Thr Trp Glu Asn Thr Pro Ile Asn
                          255                 260

Ala Lys Glu Phe (2) INFORMATION FOR SEQ ID NO: 15:

(i) SEQUENCE CHARACTERISTICS:
          (A) LENGTH: 253 amino acids
          (B) TYPE: amino acid
          (D) TOPOLOGY: linear (xi) SEQUENCE DESCRIPTION: SEQ ID NO: 15:

Asp Gly Ser Pro Asn Thr Pro Phe Arg Lys
          1               5                   10

Asp Leu Ile Ser Leu Asp Ser Ser Pro Ala
                          15                  20

Lys Glu Arg Leu Glu Asp Gly Cys Val His
                          25                  30

Pro Leu Glu Glu Ala Met Leu Ser Cys Asp
                          35                  40

Met Asp Gly Ser Arg His Phe Pro Glu Ser
                          45                  50

Arg Asn Ser Ser His Ile Lys Arg Pro Met
                          55                  60
```

```
            Asn Ala Phe Met Val Trp Ala Lys Asp Glu
                             65                  70

Arg Arg Lys Ile Leu Gln Ala Phe Pro Asp
                             75                  80

Met His Asn Ser Ser Ile Ser Lys Ile Leu
                             85                  90

Gly Ser Arg Trp Lys Ser Met Thr Asn Gln
                             95                 100

Glu Lys Gln Pro Tyr Tyr Glu Glu Gln Ala
                            105                 110

Leu Leu Ile Val Ile Thr Trp Arg Ser Ile
                            115                 120

Leu Thr Thr Ser Thr Ser Arg Gly Gln Ala
                            125                 130

His Leu His Arg Gly Gly Gln Ala Ala Ala
                            135                 140

Arg Gly Arg Val Gln Gly Pro Asp Glu Asp
                            145                 150

Pro Ala Ser Gly Cys Pro Pro Glu Leu Arg
                            155                 160

Asp Pro Pro Ala Gly Trp Pro Gly Ala Asp
                            165                 170

Glu Leu Leu Arg Cys Pro Val Pro Ser Gly
                            175                 180

Ser Arg His Ala Ala Ala Gln Pro Leu Val
                            185                 190

Glu His Tyr Val Pro Arg Ser Leu Asp Pro
                            195                 200

Asn Met Pro Val Ile Val Asn Thr Cys Ser
                            205                 210

Leu Arg Glu Glu Gly Glu Gly Thr Asp Asp
                            215                 220

Arg His Ser Val Ala Asp Gly Glu Met Tyr
                            225                 230

Arg Tyr Ser Glu Asp Glu Asp Ser Glu Gly
                            235                 240

Glu Glu Lys Ser Asp Gly Glu Leu Val Val
                            245                 250

Leu Thr Asp (2) INFORMATION FOR SEQ ID NO: 16:

(i) SEQUENCE CHARACTERISTICS:
         (A) LENGTH: 308 amino acids
         (B) TYPE: amino acid
         (D) TOPOLOGY: linear (xi) SEQUENCE DESCRIPTION: SEQ ID NO: 16:

Met Ser Ser Cys Val Pro Arg Pro
          1               5

Pro Ser His Gly Gly Pro Thr Arg Asp Leu
                          10                  15

Gln Ser Ser Pro Pro Ser Leu Pro Leu Gly
                          20                  25

Phe Leu Gly Glu Gly Asp Ala Val Thr Lys
                          30                  35
```

```
Ala Ile Gln Asp Ala Arg Gln Leu Leu His
         40                  45

Ser His Ser Gly Ala Leu Asp Gly Ser Pro
         50                  55

Asn Thr Pro Phe Arg Lys Asp Leu Ile Ser
         60                  65

Leu Asp Ser Ser Pro Ala Lys Glu Arg Leu
         70                  75

Glu Asp Gly Cys Val His Pro Leu Glu Glu
         80                  85

Ala Met Leu Ser Cys Asp Met Asp Gly Ser
         90                  95

Arg His Phe Pro Glu Ser Arg Asn Ser Ser
        100                 105

His Ile Lys Arg Pro Met Asn Ala Phe Met
        110                 115

Val Trp Ala Lys Asp Glu Arg Arg Lys Ile
        120                 125

Leu Gln Ala Phe Pro Asp Met His Asn Ser
        130                 135

Ser Ile Ser Lys Ile Leu Gly Ser Arg Trp
        140                 145

Lys Ser Met Thr Asn Gln Glu Lys Gln Pro
        150                 155

Tyr Tyr Glu Glu Gln Ala Arg Leu Ser Lys
        160                 165

Gln His Leu Glu Lys Tyr Pro Asp Tyr Lys
        170                 175

Tyr Lys Pro Arg Pro Lys Arg Thr Cys Ile
        180                 185

Val Glu Gly Lys Arg Leu Arg Val Gly Glu
        190                 195

Tyr Lys Ala Leu Met Arg Thr Arg Arg Gln
        200                 205

Asp Ala Arg Gln Ser Tyr Val Ile Pro Pro
        210                 215

Gln Ala Gly Gln Val Gln Met Ser Ser Ser
        220                 225

Asp Val Leu Tyr Pro Arg Ala Ala Gly Met
        230                 235

Pro Leu Ala Gln Pro Leu Val Glu His Tyr
        240                 245

Val Pro Arg Ser Leu Asp Pro Asn Met Pro
        250                 255

Val Ile Val Asn Thr Cys Ser Leu Arg Glu
        260                 265

Glu Gly Glu Gly Thr Asp Asp Arg His Ser
        270                 275

Val Ala Asp Gly Glu Met Tyr Arg Tyr Ser
        280                 285

Glu Asp Glu Asp Ser Glu Gly Glu Glu Lys
        290                 295
```

```
        Ser Asp Gly Glu Leu Val Val Leu Thr Asp
                        300                 305
```

(2) INFORMATION FOR SEQ ID NO: 17:

(i) SEQUENCE CHARACTERISTICS:
        (A) LENGTH: 712 amino acids
        (B) TYPE: amino acid
        (D) TOPOLOGY: linear (xi) SEQUENCE DESCRIPTION: SEQ ID NO: 17:

```
        Met Met Ala Gln Ser
        1               5

Asn Met Phe Thr Val Ala Asp Val Leu Ser
                        10              15

Gln Asp Glu Leu Arg Lys Lys Leu Tyr Gln
                        20              25

Thr Phe Lys Asp Arg Gly Ile Leu Asp Thr
                        30              35

Leu Lys Thr Gln Leu Arg Asn Gln Leu Ile
                        40              45

His Glu Leu Met His Pro Val Leu Ser Gly
                        50              55

Glu Leu Gln Pro Arg Ser Ile Ser Val Glu
                        60              65

Gly Ser Ser Leu Leu Ile Gly Ala Ser Asn
                        70              75

Ser Leu Val Ala Asp His Leu Gln Arg Cys
                        80              85

Gly Tyr Glu Tyr Ser Leu Ser Val Phe Phe
                        90              95

Pro Glu Ser Gly Leu Ala Lys Glu Lys Val
                        100             105

Phe Thr Met Gln Asp Leu Leu Gln Leu Ile
                        110             115

Lys Ile Asn Pro Thr Ser Ser Leu Tyr Lys
                        120             125

Ser Leu Val Ser Gly Ser Asp Lys Glu Asn
                        130             135

Gln Lys Gly Phe Leu Met His Phe Leu Lys
                        140             145

Glu Leu Ala Glu Tyr His Gln Ala Lys Glu
                        150             155

Ser Cys Asn Met Glu Thr Gln Thr Ser Ser
                        160             165

Thr Phe Asn Arg Asp Ser Leu Ala Glu Lys
                        170             175

Leu Gln Leu Ile Asp Asp Gln Phe Ala Asp
                        180             185

Ala Tyr Pro Gln Arg Ile Lys Phe Glu Ser
                        190             195

Leu Glu Ile Lys Leu Asn Val Tyr Lys Arg
                        200             205

Glu Ile Glu Glu Gln Leu Arg Ala Glu Met
                        210             215
```

```
Cys Gln Lys Leu Lys Phe Phe Lys Asp Thr
                220                 225

Glu Ile Ala Lys Ile Lys Met Glu Ala Lys
                230                 235

Lys Lys Tyr Glu Lys Glu Leu Thr Met Phe
                240                 245

Gln Asn Asp Phe Glu Lys Ala Cys Gln Ala
                250                 255

Lys Ser Glu Ala Leu Val Leu Arg Glu Lys
                260                 265

Ser Thr Leu Glu Arg Ile His Lys His Gln
                270                 275

Glu Ile Glu Thr Lys Glu Ile Tyr Ala Gln
                280                 285

Arg Gln Leu Leu Leu Lys Asp Met Asp Leu
                290                 295

Leu Arg Gly Arg Glu Ala Glu Leu Lys Gln
                300                 305

Arg Val Glu Ala Phe Glu Leu Asn Gln Lys
                310                 315

Leu Gln Glu Glu Lys Met Lys Ser Ile Thr
                320                 325

Glu Ala Leu Arg Arg Gln Glu Gln Asn Ile
                330                 335

Lys Ser Phe Glu Glu Thr Tyr Asp Arg Lys
                340                 345

Leu Lys Asn Glu Leu Leu Lys Tyr Gln Leu
                350                 355

Glu Leu Lys Asp Asp Tyr Ile Ile Arg Thr
                360                 365

Asn Arg Leu Ile Glu Asp Glu Arg Lys Asn
                370                 375

Lys Glu Lys Ala Val His Leu Gln Glu Glu
                380                 385

Leu Ile Ala Ile Asn Ser Lys Lys Glu Glu
                390                 395

Leu Asn Gln Ser Val Asn Arg Val Lys Glu
                400                 405

Leu Glu Leu Glu Leu Glu Ser Val Lys Ala
                410                 415

Gln Ser Leu Ala Ile Thr Lys Gln Asn His
                420                 425

Met Leu Asn Glu Lys Val Lys Glu Met Ser
                430                 435

Asp Tyr Ser Leu Leu Lys Glu Glu Lys Leu
                440                 445

Glu Leu Leu Ala Gln Asn Lys Leu Leu Lys
                450                 455

Gln Gln Leu Glu Glu Ser Arg Asn Glu Asn
                460                 465

Leu Arg Leu Leu Asn Arg Leu Ala Gln Pro
                470                 475

Ala Pro Glu Leu Ala Val Phe Gln Lys Glu
                480                 485
```

```
Leu Arg Lys Ala Glu Lys Ala Ile Val Val
            490                 495

Glu His Glu Glu Phe Glu Ser Cys Arg Gln
            500                 505

Ala Leu His Lys Gln Leu Gln Asp Glu Ile
            510                 515

Glu His Ser Ala Gln Leu Lys Ala Gln Ile
            520                 525

Leu Gly Tyr Lys Ala Ser Val Lys Ser Leu
            530                 535

Thr Thr Gln Val Ala Asp Leu Lys Leu Gln
            540                 545

Leu Lys Gln Thr Gln Thr Ala Leu Glu Asn
            550                 555

Glu Val Tyr Cys Asn Pro Lys Gln Ser Val
            560                 565

Ile Asp Arg Ser Val Asn Gly Leu Ile Asn
            570                 575

Gly Asn Val Val Pro Cys Asn Gly Glu Ile
            580                 585

Ser Gly Asp Phe Leu Asn Asn Pro Phe Lys
            590                 595

Gln Glu Asn Val Leu Ala Arg Met Val Ala
            600                 605

Ser Arg Ile Thr Asn Tyr Pro Thr Ala Trp
            610                 615

Val Glu Gly Ser Ser Pro Asp Ser Asp Leu
            620                 625

Asn Thr Lys Ala Arg Val Lys Glu Leu Gln
            630                 635

Gln Glu Ala Glu Arg Leu Glu Lys Ala Phe
            640                 645

Arg Ser Tyr His Arg Arg Val Ile Lys Asn
            650                 655

Ser Ala Lys Ser Pro Lys Ala Ala Lys Ser
            660                 665

Pro Pro Leu Cys Thr Cys Trp Lys Pro Ser
            670                 675

Lys Thr Leu Leu Pro Val Pro Arg Lys Asp
            680                 685

Ile Phe Leu Glu Arg Thr Glu Leu Ser Leu
            690                 695

Ser Ser Leu Lys Trp Ala His Leu Lys Lys
            700                 705

Gly Met Thr Ser Trp Lys His
            710
```

(2) INFORMATION FOR SEQ ID NO: 18:

(i) SEQUENCE CHARACTERISTICS:

(A) LENGTH: 294 amino acids
    (B) TYPE: amino acid
    (D) TOPOLOGY: linear (xi) SEQUENCE DESCRIPTION: SEQ ID NO: 18:

-continued

```
Asn Arg Ala Glu Gly Pro Pro Glu Pro Ser
 1               5                  10

Arg Val Ser Ser Val Ser Ser Gln Phe Ser
                    15                  20

Asp Ala Ala Gln Ala Ser Pro Ser Ser His
                    25                  30

Ser Ser Thr Pro Ser Trp Cys Glu Glu Pro
                    35                  40

Ala Gln Ala Asn Met Asp Ile Ser Thr Gly
                    45                  50

His Met Ile Leu Ala Tyr Met Glu Asp His
                    55                  60

Leu Arg Asn Arg Asp Arg Leu Ala Lys Glu
                    65                  70

Trp Gln Ala Leu Cys Ala Tyr Gln Ala Glu
                    75                  80

Pro Asn Thr Cys Ala Thr Ala Gln Gly Glu
                    85                  90

Gly Asn Ile Lys Lys Asn Arg His Pro Asp
                    95                  100

Phe Leu Pro Tyr Asp His Ala Arg Ile Lys
                    105                 110

Leu Lys Val Glu Ser Ser Pro Ser Arg Ser
                    115                 120

Asp Tyr Ile Asn Ala Ser Pro Ile Ile Glu
                    125                 130

His Asp Pro Arg Met Pro Ala Tyr Ile Ala
                    135                 140

Thr Gln Gly Pro Leu Ser His Thr Ile Ala
                    145                 150

Asp Phe Trp Gln Met Val Trp Glu Ser Gly
                    155                 160

Cys Thr Val Ile Val Met Leu Thr Pro Leu
                    165                 170

Val Glu Asp Gly Val Lys Gln Cys Asp Arg
                    175                 180

Tyr Trp Pro Asp Glu Gly Ala Ser Leu Tyr
                    185                 190

His Val Tyr Glu Val Asn Leu Val Ser Glu
                    195                 200

His Ile Trp Cys Glu Asp Phe Leu Val Arg
                    205                 210

Ser Phe Tyr Leu Lys Asn Val Gln Thr Gln
                    215                 220

Glu Thr Arg Thr Leu Thr Gln Phe His Phe
                    225                 230

Leu Ser Trp Pro Ala Glu Gly Thr Pro Ala
                    235                 240

Ser Thr Arg Pro Leu Leu Asp Phe Arg Arg
                    245                 250

Lys Val Asn Lys Cys Tyr Arg Gly Arg Ser
                    255                 260
```

```
            Cys Pro Ile Ile Val His Cys Ser Asp Gly
                            265                 270

Ala Gly Arg Thr Gly Thr Tyr Ile Leu Ile
                            275                 280

Asp Met Val Leu Asn Arg Met Ala Lys Gly
                            285                 290

Val Lys Glu Ile (2) INFORMATION FOR SEQ ID NO: 19:

(i) SEQUENCE CHARACTERISTICS:
        (A) LENGTH: 548 amino acids
        (B) TYPE: amino acid
        (D) TOPOLOGY: linear (xi) SEQUENCE DESCRIPTION: SEQ ID NO: 19:

Met Glu Gly Pro Val Glu Gly
            1               5

Arg Asp Thr Ala Glu Leu Pro Ala Arg Thr
                            10                  15

Ser Pro Met Pro Gly His Pro Thr Ala Ser
                            20                  25

Pro Thr Ser Ser Glu Val Gln Gln Val Pro
                            30                  35

Ser Pro Val Ser Ser Glu Pro Pro Lys Ala
                            40                  45

Ala Arg Pro Pro Val Thr Pro Val Leu Leu
                            50                  55

Glu Lys Lys Ser Pro Leu Gly Gln Ser Gln
                            60                  65

Pro Thr Val Ala Gly Gln Pro Ser Ala Arg
                            70                  75

Pro Ala Ala Glu Glu Tyr Gly Tyr Ile Val
                            80                  85

Thr Asp Gln Lys Pro Leu Ser Leu Ala Ala
                            90                  95

Gly Val Lys Leu Leu Glu Ile Leu Ala Glu
                            100                 105

His Val His Met Ser Ser Gly Ser Phe Ile
                            110                 115

Asn Ile Ser Val Val Gly Pro Ala Leu Thr
                            120                 125

Phe Arg Ile Arg His Asn Glu Gln asn Leu
                            130                 135

Ser Leu Ala Asp Val Thr Gln Gln Ala Gly
                            140                 145

Leu Val Lys Ser Glu Leu Glu Ala Gln Thr
                            150                 155

Gly Leu Gln Ile Leu Gln Thr Gly Val Gly
                            160                 165

Gln Arg Glu Glu Ala Ala Ala Val Leu Pro
                            170                 175

Gln Thr Ala His Ser Thr Ser Pro Met Arg
                            180                 185

Ser Val Leu Leu Thr Leu Val Ala Leu Ala
                            190                 195
```

```
Gly Val Ala Gly Leu Leu Val Ala Leu Ala
            200                 205

Val Ala Leu Cys Val Arg Gln His Ala Arg
            210                 215

Gln Gln Asp Lys Glu Arg Leu Ala Ala Leu
            220                 225

Gly Pro Glu Gly Ala His Gly Asp Thr Thr
            230                 235

Phe Glu Tyr Gln Asp Leu Cys Arg Gln His
            240                 245

Met Ala Thr Lys Ser Leu Phe Asn Arg Ala
            250                 255

Glu Gly Pro Pro Glu Pro Ser Arg Val Ser
            260                 265

Ser Val Ser Ser Gln Phe Ser Asp Ala Ala
            270                 275

Gln Ala Ser Pro Ser Ser His Ser Ser Thr
            280                 285

Pro Ser Trp Cys Glu Glu Pro Ala Gln Ala
            290                 295

Asn Met Asp Ile Ser Thr Gly His Met Ile
            300                 305

Leu Ala Tyr Met Glu Asp His Leu Arg Asn
            310                 315

Arg Asp Arg Leu Ala Lys Glu Trp Gln Ala
            320                 325

Leu Cys Ala Tyr Gln Ala Glu Pro Asn Thr
            330                 335

Cys Ala Thr Ala Gln Gly Glu Gly Asn Ile
            340                 345

Lys Lys Asn Arg His Pro Asp Phe Leu Pro
            350                 355

Tyr Asp His Ala Arg Ile Lys Leu Lys Val
            360                 365

Glu Ser Ser Pro Ser Arg Ser Asp Tyr Ile
            370                 375

Asn Ala Ser Pro Ile Ile Glu His Asp Pro
            380                 385

Arg Met Pro Ala Tyr Ile Ala Thr Gln Gly
            390                 395

Pro Leu Ser His Thr Ile Ala Asp Phe Trp
            400                 405

Gln Met Val Trp Glu Ser Gly Cys Thr Val
            410                 415

Ile Val Met Leu Thr Pro Leu Val Glu Asp
            420                 425

Gly Val Lys Gln Cys Asp Arg Tyr Trp Pro
            430                 435

Asp Glu Gly Ala Ser Leu Tyr His Val Tyr
            440                 445

Glu Val Asn Leu Val Ser Glu His Ile Trp
            450                 455
```

```
Cys Glu Asp Phe Leu Val Arg Ser Phe Tyr
            460                 465

Leu Lys Asn Val Gln Thr Gln Glu Thr Arg
            470                 475

Thr Leu Thr Gln Phe His Phe Leu Ser Trp
            480                 485

Pro Ala Glu Gly Thr Pro Ala Ser Thr Arg
            490                 495

Pro Leu Leu Asp Phe Arg Arg Lys Val Asn
            500                 505

Lys Cys Tyr Arg Gly Arg Ser Cys Pro Ile
            510                 515

Ile Val His Cys Ser Asp Gly Ala Gly Arg
            520                 525

Thr Gly Thr Tyr Ile Leu Ile Asp Met Val
            530                 535

Leu Asn Arg Met Ala Lys Gly Val Lys Glu
            540                 545

Ile
```

NUCLEIC ACIDS ENCODING PANCREATIC ISLET CELL ANTIGENS OBTAINED BY MOLECULAR CLONING

CROSS-REFERENCE TO RELATED APPLICATION

This application is a divisional of application Ser. No. 08,239,276, filed May 5, 1994, pending, which is, in turn, a continuation of Ser. No. 07/872,646, filed Jun. 8, 1992, now abandoned, which is, in turn, a continuation of Ser. No. 07/715,181, filed Jun. 14, 1991, now abandoned, which is, in turn, a continuation-in-part of Ser. No. 07/441,703, filed Dec. 4, 1989, now abandoned, which is, in turn, a continuation-in-part of Ser. No. 07/312,543, filed Feb. 17, 1989, now abandoned.

BACKGROUND OF THE INVENTION

This invention relates to pancreatic islet cell antigens that bind with antibodies found in the sera of patients afflicted with insulin-dependent (Type I) diabetes mellitus (IDDM). More particularly, the invention relates to proteins and peptides that bind with islet cell antibodies (ICA) and that are prepared by recombinant DNA (rDNA) or synthetic methods. The invention also concerns cloned DNA encoding such ICA proteins and peptides. The ICA proteins and peptides of the present invention are useful as immunoassay reagents in the presymptomatic diagnosis of IDDM.

The accumulating evidence of cellular and humoral abnormalities associated with IDDM has led to the hypothesis that the disease is an autoimmune disorder. Serum antibodies directed against the insulin-producing beta cells of the pancreatic islets have been detected by immunofluorescence, [G. F. Bottazzo, A. Florin-Christensen, and D. Doniach: Islet Cell Antibodies in Diabetes Mellitus With Autoimmune Polyendocrine Deficiencies, Lancet ii:1279–1283 (1974), and A. C. MacCuish, J. Jordan, C. J. Campbell, L. J. P. Duncan, and W. J. Irvine: Antibodies to Islet-cell in Insulin-dependent Diabetics With Coexistent Autoimmune Disease, Lancet ii:1529–1533 (1974)]. These autoantibodies are observed in 70–80% of newly diagnosed diabetics (NDD), but only in 0.1–1% of normal control subjects [C. H. Brogren and A. Lernmark: Islet Cell Antibodies in Diabetes. Clin. Endocrinol. Metab. 11:409–430 (1982)], and G. F. Bottazzo, R. Pujol-Borrell, and D. Doniach: Humoral and Cellular Immunity in Diabetes Mellitus. Clin. Immunol. Allergy 1:139–159 (1981)]. ICAs have come to be accepted as one predictive factor for IDDM. A review of current knowledge on ICA is provided by A. Lernmark, Diabetic Medicine 4:285–292 (1987).

The conventional ICA assay consists of exposing pancreas sections to sera, staining with a second antibody bearing either a fluorescent [G. F. Bottazzo et al., supra] or enzyme label [P. G. Colman, M. Tatkus, A. Rabizadeh, C. Cahill, and G. S. Eisenbarth: Assay for Islet Cell Antibodies with Rat Pancreas and Peroxidase Protein A. Diabetes Care 11:367–368 (1988)], and observing under a microscope. Another similar method involves a biotin-avidin sandwich and immunofluorescent detection [T. Kobayashi, T. Sugimoto, T. Itoh, K. Kosaka, T. Tanaka, S. Suwa, K. Sato and K. Tsuju: The Prevalence of Islet Cell Antibodies in Japanese Insulin-dependent and Non-insulin-dependent Diabetic Patients Studied by Indirect Immunofluorescence and by a New Method. Diabetes 35:335–340 (1986)]. These methods are time consuming, laborious, difficult to reproduce, and have limited sensitivity. The development of a more convenient immunoassay for ICA would permit widespread testing for epidemiology and correlation with IDDM, and ultimately prediction of the disease with a screening test.

A major limitation of current ICA tests is the limited knowledge and characterization of the islet is cell antigens involved. The ICA's may be of low titer or affinity and approachable only with characterized antigens. ICA antigens that are detected by the immunofluorescence test are of w special interest; these antigens may include:

(1) islet cell surface moieties [N. K. MacLaren, S. W. Hugng, and J. Fogh: Antibody to Cultured Human Insulinoma Cells in Insulin-dependent Diabetes. Lancet 1:997–1000 (1975), and A. Lernmark, Z. R. Freedman, C. Hofmann, A. H. Rubenstein, D. F. Steiner, R. L. Jackson, R. J. Winter and H. S. Traisman: Islet-cell-surface Antibodies in Juvenile Diabetes Mellitus. N. Engl. J. Med. 299:375–380 (1978)], (2) insulin [J. P. Palmer, C. M. Asplin, P. Clemons, K. Lyen, 0. Tetpati, P. K. Raghu and T. L. Paquette: Insulin Antibodies in Insulin-dependent Diabetics Before Insulin Treatment. Science 222:1337–1339 (1983), and S. Srikanta, A. T. Ricker, D. K. McCulloch, J. S. Soeldner, G. S. Eisenbarth and J. P. Palmer: Autoimmunity to Insulin, Beta Cell Dysfunction, and Development of Insulin-dependent Diabetes Mellitus. Diabetes 35:139–142 (1986)], (3) a 64,000 dalton (64 kd) islet protein of unknown cellular localization (S. Baekkeskov, J. H. Nielsen, B. Marner, T. Bilde, J. Ludvigsson, and A. Lernmark: Autoantibodies in Newly Diagnosed Diabetic Children Immunoprecipitate Human Pancreatic Islet Cell Proteins. Nature 298:167–169 (1982). Recent evidence indicates that the 64 kd protein is glutamic acid decarboxylase (GAD). [S. Baekkeskov, J-H. Aanstoot, S. Christgau, A. Reetz, M. Solimena, M. Cascalho, F. Folli, H. Richter-Olesen and P. De-Camilli: Identification of the 64k autoantigen in insulin-dependent diabetes as the GABA-synthesizing enzyme glutamic acid decarboxylase. Nature 347:151–156 (1990)], (4) cytoplasmic antigens [G. F. Bottazzo, A. Florin-Christensen, and D. Doniach: Islet Cell Antibodies in Diabetes Mellitus With Autoimmune Polyendocrine Deficiencies. Lancet 2:1279–1283 (1974), A. C. MacCuish, J. Jordan, C. J. Campbell, L. J. P. Duncan, and W. J. Irvine: Antibodies to Islet-Cell in Insulin-Dependent Diabetics With Coexistent Autoimmune Disease. Lancet 2:1529–1533 (1974), R. Lendrum, G. Walker, and D. R. Gambli: Islet-Cell Antibodies in Juvenile Diabetes Mellitus of Recent Onset. Lancet 1:880–883 (1975), and W. J. Irvine, C. J. McCallum, R. S. Gray, G. J. Campbell, L. J. P. Duncan, J. W. Farquhar, H. Vaughan, and P. J. Morris: Pancreatic Islet Cell Antibodies in Diabetes Mellitus Correlated With The Duration and Type of Diabetes, Co-existent Autoimmune Disease, and HLA-type. Diabetes 26:138–147 (1977)], (5) glycoconjugates [R. C. Nayak, M. A. K. Omar, A. Rabizadeh, S. Srikanta, and G. S. Eisenbarth, "Cytoplasmic" Islet Cell Antibodies: Evidence That the Target Antigen is a Sialoglycoconjugate. Diabetes 34:617–619 (1985); P. Vardi, E. E. Dibella, T. J. Pasquarello, and S. Srikanta, Islet Cell Autoantibodies: Pathobiology and Clinical Applications. Diabetes Care 10:645–56 (1987); B. K. Gillard, J. W. Thomas, L. J. Nell and D. M. Marcus, Antibodies Against Ganglioside GT3 in the Sera of Patients with Type I Diabetes Mellitus. Journal of Immunology 142:3826–32 (1989)].

Several reports indicate a high prevalence of anti-64 kd antibody in prediabetic sera as well as newly diagnosed diabetic sera [S. Baekkeskov, M. Landin, J. K. Kristensen, S. Srikanta, G. Jan Bruining, R. Mandrup-Poulsen, C. de Beaufort, J. S. Soeldner, G. Eisenbarth, F. Lindgren, G. Sundquist, and A. Lernmark: Antibodies to a 64,000 MW Human Islet Cell Antigen Precede the Clinical Onset of Insulin-dependent Diabetes. J. Clin. Invest. 79:926–934 (1987), M. A. Atkinson, N. K. Maclaren, W. J. Riley, D. W. Sharp and L. Holmes: Mr 64,000 Autoantibodies (64 KA) Predict Insulin Dependent Diabetes. American Diabetes Assoc. 48th Annual Meeting (1988) Abstract #391, and M. A. Atkinson, N. K. Maclaren, D. W. Scharp, P. E. Lacy, and W. J. Riley: 64000 Mr autoantibodies as predictors of insulin-dependent diabetes. The Lancet 335:1357–1360 (1990)].

Some other molecular species have been characterized by Western blotting as being "common antigens" recognized by diabetic sera [D. G. Karounos, V. J. Virta, L. J. Nell, and J. W. Thomas: Analysis of Human and RINm5F Islet Cell Antigens. American Diabetes Assoc. Res. Symp. Woods Hole, Mass. October 1987; Abstract #120]. These antigens have molecular weights of 150 kd, 84 kd, 60 kd, 49 kd, and 36 kd. A more recent report from the same laboratory indicates that there is a RIN antigen of Mr 52,000 that reacts with 29% of diabetic sera. [D. G. Karounos and J. W. Thomas: Recognition of Common Islet Antigen by autoantibodies From NOD Mice and Humans With IDDM. Diabetes 39:1085–1090 (1990), D. G. Karounos, L. J. Nell, and J. W. Thomas: Autoantibodies present at onset of type I diabetes recognize multiple islet cell antigens. Autoimmunity 6:79–91(1990), and D. G. Karounos, J. S. wolinsky, B. K. Gillard, and J. W. Thomas: Molecular Mimicry in Type I Diabetes: An Antigenic Determinant on a Rubella Virus Protein is Shared with a 52 kD Beta Cell autoantigen. Diabetes 39:96A (1990)]. The first and third references indicate that the 52,000 antigen is RIN specific, not found in human islets or other tissue.

SUMMARY OF THE INVENTION

The present invention provides a series of cloned nucleic acids that code for one or more proteins or protein fragments which bind selectively with pancreatic islet cell antibodies (ICA). Such cloned nucleic acids are characterized by the cDNA inserts in deposited recombinant bacteriophages ATCC 40550, 40551, 40552, 40553, 40554, 40703, 40704, 40705, 40706, and ICA-512.3 (ATCC75030).

The present invention, accordingly, also provides ICA proteins and peptide fragments thereof which are encoded by the cloned nucleic acids and are useful in the diagnosis of insulin-dependent (Type I) diabetes mellitus (IDDM). The ability of such proteins and peptides to bind to the antibody combining site on ICAs also confers utility in the binding or blocking of human immunoglobulin, T-cells or B-cells involved in IDDM, including circulating immunoglobulin, T-cells, and B-cells.

The ICA proteins and peptides of the present invention are obtained by such methods as full or partial expression, optionally with subsequent fragmentation, of the present cloned nucleic acids; and peptide or polypeptide synthesis based on the amino acid sequences determined from the present cloned cDNAs or from the full length ICA antigen genes that can be determined or isolated from islet cell nucleic acid libraries with the aid of the present complementary cloned cDNA sequences. Accordingly, such ICA proteins and peptides include the full length ICA proteins present in or on islet cells and which are expressed by the human gene whose mRNA is at least in part complementary with the complete sequence of the present cloned cDNAs. Also included in the ICA proteins and peptides of the present invention are the proteins expressed by recombinant cloning vehicles comprising the present cDNA inserts and fragments of such proteins obtained by partial expression or by subsequent fragmentation such as with restriction nucleases. The ICA proteins and peptides of the present invention also include peptides obtained by protein synthesis, such as those that are 3 amino acids in length or longer, which represent ICA epitopes or analogues or derivatives thereof.

The present invention offers a number of significant advantages. The molecular cloning of ICA antigens affords the preparation of large and reproducible amounts of material for use in research, diagnosis, and treatment of IDDM, as well as the opportunity to study the biological mechanisms involved in islet cell destruction and the appearance of ICA. The availability of large quantities of pure antigen enables the development of highly sensitive and specific immunoassays which can be used to screen the general population for presymptomatic IDDM or a predisposition to develop IDDM.

BRIEF DESCRIPTION OF THE DRAWINGS AND SEQUENCE LISTING

FIGS. 1–5, 8 and 9 are reactivity profiles of ATCC-deposited ICA clones prepared in accordance with the present invention with diabetic and normal sera under conditions described in the Examples.

FIGS. 7 and 10 are summaries of the sera profiles of ICA clones showing reactivity values assigned by visual interpretation of the profiles in FIGS. 1–5 and 14–15, respectively.

Figure 1B:
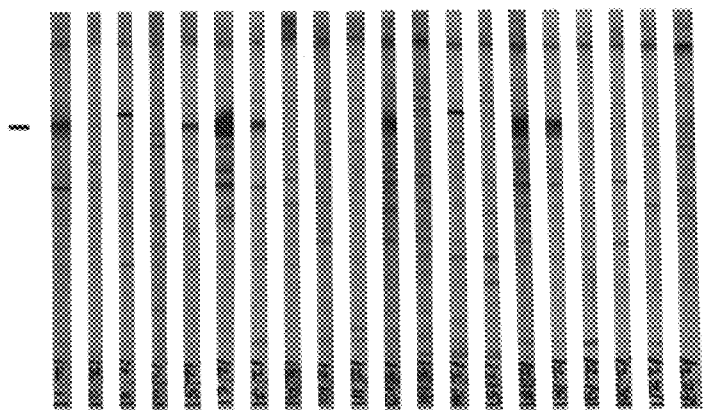
Figure 1A:
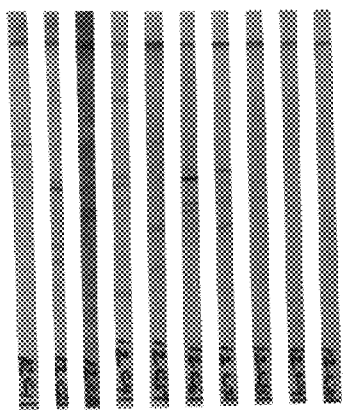
Figure 2A:
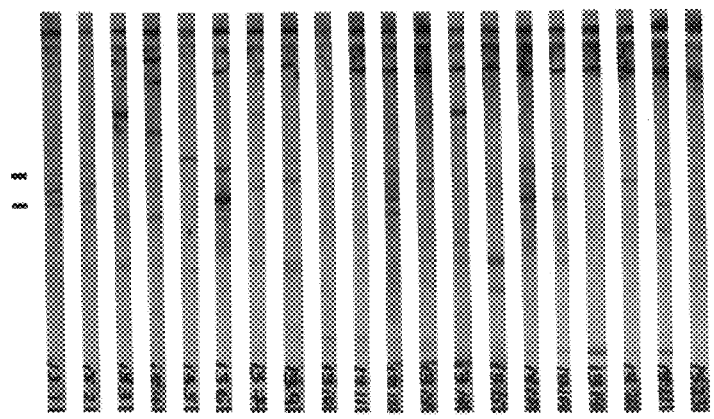
Figure 2B:
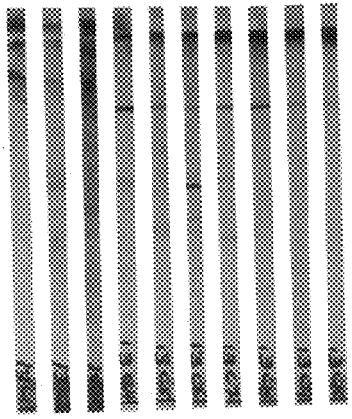
Figure 3A:
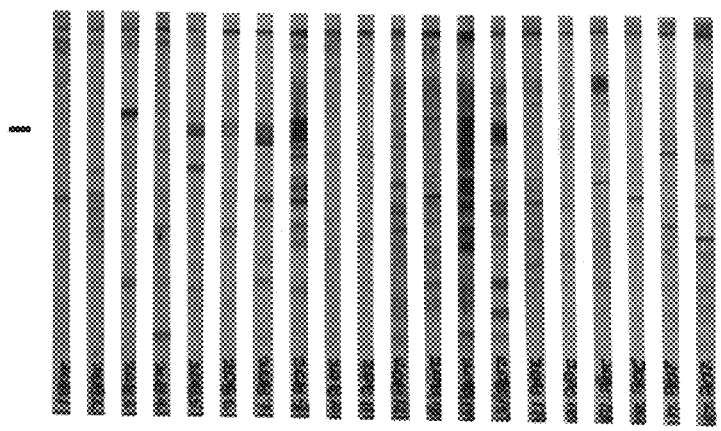
Figure 3B:
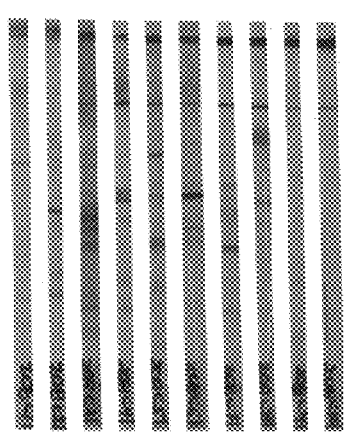
Figure 4A:
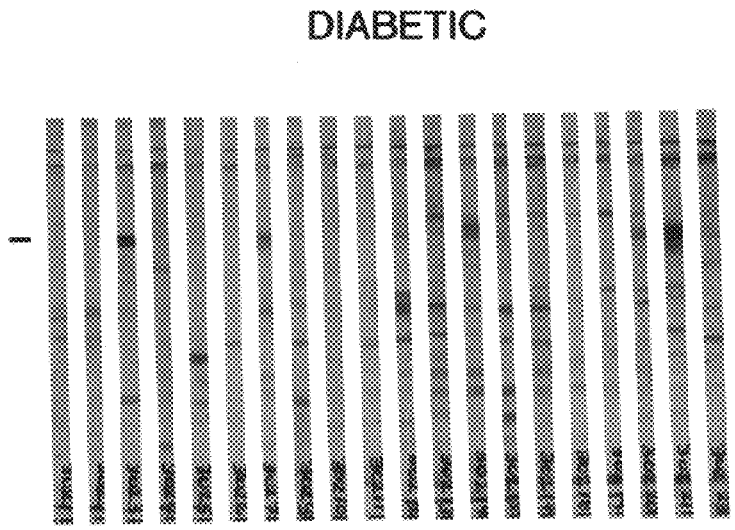
Figure 4B:
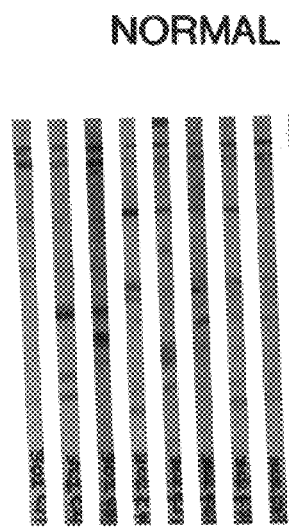
Figure 5A:
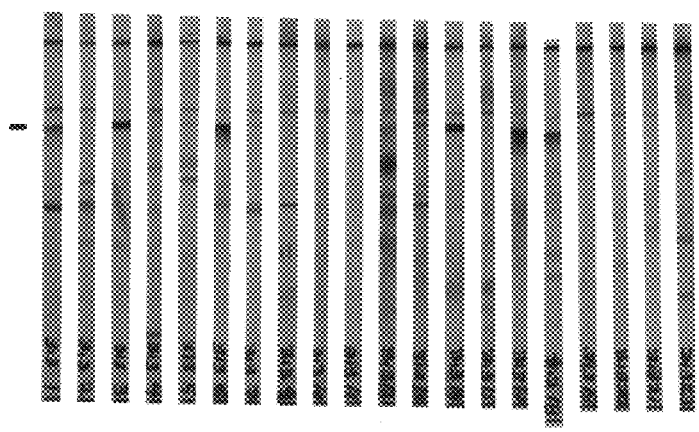
Figure 5B:
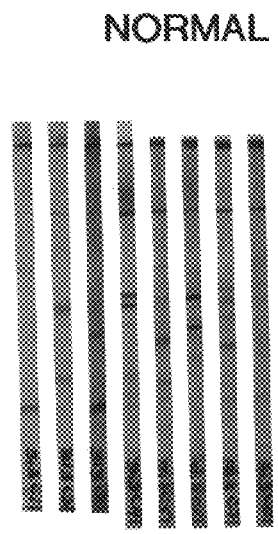

The sequence listing provides the DNA and inferred protein sequences for particular ICA clones as following:

| SEQ ID NO. | ICA CLONE |
| --- | --- |
| 1 | 12 |
| 2 | 13 |
| 3 | 208 |
| 4 | 302 |
| 5 | 313 |
| 6 | 12.3 |
| 7 | 525 |
| 8 | 505 |
| 9 | 512 |
| 10 | 512.3 |

DESCRIPTION OF THE PREFERRED EMBODIMENTS

As used herein, the term "ICA antigens" shall be understood to refer to the proteins and peptides provided by the present invention even though it is recognized that in some cases peptide forms will not be "antigens" in the strict sense, i.e., they will be haptenic since they will require attachment to a conventional macromolecular carrier in order to stimulate the production of antibodies in a host animal.

Furthermore, the "cloned nucleic acids", "cloned ICA antigen sequences", "cDNA inserts", and like terms shall refer to the inserts in deposited recombinant phages ATCC 40550, 40551, 40552, 40553, 40554, 40703, 40704, 40705, 40706, and 75030 and also to other nucleic acid sequences of full length genes, or fragments of such sequences, comprising such deposited sequences. It will be recognized that one or more full length ICA antigens are characterized by homology with the above deposited cDNA inserts, however, it is possible that two or more of such cDNA inserts correspond to a single ICA antigen. For example, the insert in ATCC 40703 appears to encompass the inserts for both ATCC 40550 and ATCC 40554, and thus these three inserts may all correspond to different and/or overlapping portions of a single ICA antigen. Moreover, ATCC 40706 is comprised in ICA-512.3 (ATCC 75030).

Preparation of Cloned ICA Antigen Sequences

In general, the cloned ICA antigen sequences of the present invention are obtained by expressing human genes in a suitable recombinant cloning vehicle, e.g., bacteriophage, and probing the resulting gene library with IDDM serum to select antigens that are recognized by ICA antibodies. Recombinant antigens are then screened with a panel of diabetic and normal sera to determine the disease specificity of the identified clones.

The particular deposited clones were more particularly obtained by the following method (further details can be found in the Examples below). A human cDNA library was generated by extracting RNA from purified human islets. This RNA was fractionated by chromatography to separate poly-A mRNA from other RNA such as ribosomal RNA and fragments of degraded RNA. The separated MRNA was reverse transcribed with a commercially available cDNA kit (Bethesda Research Laboratories), ligated to Eco RI DNA linkers, and ligated into lambda gt-11 arms for in vitro packaging. The ligated lambda was packaged using a commercial kit (Stratagene) and then amplified on a bacterial lawn in a plate format.

The phage library was screened with antibodies from autoimmune patients with Type I diabetes. Agarose plates were spread with bacteria infected with the phage, and recombinant protein expression was induced chemically. The protein was deposited onto filters which were then probed with serum. Plaques that appeared to be positive were isolated from the agarose plates and purified through two rounds of isolation. Subsequent to cloning, the gt-11 phage was infected into a bacterial host for large scale expression. Specificity of the proteins expressed by the cloned cDNA was evaluated by Western blotting of bacterial extracts containing the cloned human protein. Preparative polyacrylamide gels were run and electroblotted onto membranes, the membranes were cut into strips, and then reacted with a series of normal and diabetic sera. The clones that generated proteins that reacted exclusively or predominantly with diabetic sera were selected.

Recombinant Cloning Vehicles and Subcloning

As is conventionally known in the art, the cDNA transcripts of the present invention, such as library cDNA or cDNA inserts excised from a cloning vehicle, can be incorporated into a variety of recombinant cloning vehicles for amplification of sequences of interest and for expression of ICA antigens of interest. A recombinant cloning vehicle will be understood to be a biochemical molecule or structure, e.g., DNA, that allows insertion of polynucleotide sequences and replication of the inserted polynucleotide sequences when the vehicle is appropriately incorporated into a host cell. An expression vehicle additionally includes the property of expressing the protein encoded by the inserted polynucleotide. In an expression vector, the inserted ICA antigen sequence is operably linked to a suitable control sequence capable of effecting the expression of ICA antigen in a suitable host. is The control sequence involved will vary according to the host and transformation method selected. These matters are within the ordinary skill of the art.

Suitable recombinant cloning vehicles include plasmids, viruses and bacteriophage, and integratable fragments of DNA (i.e., fragments integratable into the host genome by recombination). Expression vehicles are particularly preferred and are exemplified, without limitation, by bacterial pEMBL, PMMB, pUK, pATH, and pGEX, yeast pAAH5, pYE4, and pAB112, mammalian pRSV, vaccinia derived vectors, baculovirus derived vectors, papilloma derived vectors, retroviral vectors, and shuttle vectors such as pCDM8. For a review, see D. M. Glover, DNA Cloning: A Practical Approach (1985) IRL Press Ltd. Suitable host cells include procaryotes, yeast, and higher eucaryotic cells including mammalian cells.

Subcloning of cDNA inserts can involve excising the insert for ligation into a different cloning vehicle. The insert can be excised using the restriction enzyme corresponding to the linkers used in the original insertion or using restriction enzymes selected from a restriction map of the insert. The excised cDNA can be inserted into another suitable vector for sequencing, amplification, or expression as desired. Should the terminal restriction sites in the original cloning vehicle have been destroyed, other enzymes can be used to recover the insert and resulting flanking regions from the cloning vehicle deleted by conventional means.

Another method of preparing DNA fragments for insertion into a cloning vehicle is the use of polymerase chain reaction (PCR) amplification. This procedure can be used on ligation reaction products to amplify the amount of DNA and introduce desired restriction sites for subcloning. PCR can also be used to replicate a fragment with desired restriction sites for transfer from one vehicle into another vehicle.

Full-Length Gene Cloning

Fragments of the cDNA inserts of the present invention can be used to isolate full-length cDNA or genomic DNA clones from appropriate libraries by standard methods. The target library is spread on plates, allowed to grow, transferred to filters, and reacted with DNA probes. Such DNA probes are generated from restriction fragments of the cDNA inserts by such methods as end labeling, nick translation, random primed transcription, or photochemical means. Oligonucleotides can be synthesized, labeled, and used as hybridization probes. RNA probes can also be generated from subcloned cDNA by transcription from appropriate templates.

Recombinant cloning vehicles, e.g., phage or plasmids, that appear to react with the partial cDNA clones are re-screened and then restriction mapped. Promising clones are then sequenced to confirm the hybridization of the original probes and to obtain extended sequence information on the larger fragment. If full-length clones are not obtained in this procedure, the complete sequence of the nucleic acid coding for the human gene can be pieced together from overlapping sequences of cloned fragments.

An alternative method for obtaining longer fragments, and possibly full-length clones, uses antibodies raised against ICA antigens expressed by partial clones. After identifying an antigen of interest, it can be used as an immunogen to raise monoclonal or polyclonal antibodies of high titer and affinity. Such antibodies will enable the detection of longer cDNA clones and cDNA clones present in lower amounts in the library.

Antigen and Peptide Synthesis

ICA antigens, as defined herein, can be prepared in a number of different ways from the clones and sequence information provided by the present invention. One can simply express the proteins from ICA antigen clones obtained according to the present invention, particularly from the deposited clones. Such expressed proteins, or fragments or digestion products thereof, can be used as antigens for binding to islet cell antibodies. However, direct use of bacterial expression extracts may not be possible in some cases since human sera normally react nonspecifically with E. coli proteins. In such cases, the expressed ICA antigens can be isolated by conventional techniques such as electrophoretic separation followed by immobilization on membranes (western blotting), or by column chromatography or affinity purification (e.g., anti-beta-galactosidase affinity resin chromatography or other conventional biochemical means, e.g., salt or temperature precipitation).

Alternatively, peptide fragments can be synthesized by well-known methods from the amino acid sequences deduced from experimentally determined DNA sequences of ICA antigen clones. Overlapping peptides can be synthesized and tested for reactivity with ICA sera. As reactive peptides are found, smaller peptides can be prepared in order to map the smallest reacting unit, i.e., the epitope.

Methods

A principal use of the ICA antigens provided by the present invention is in the diagnosis and prediction of IDDM. In such a method, a blood sample, normally a serum sample, is reacted with a selected one or series of ICA antigens and immunoreactivity determined by any conventional technique. It is further contemplated that the immunoreactivity profile with different ICA antigens can provide diagnostically significant information concerning the nature of the disease, e.g., subtypes, the state of the disease, the proximity to onset of the disease, the efficacy of therapy, e.g., immune therapy, and the like.

A further use of the present ICA antigens is in the identification, marking, or specific destruction of autoreactive B-cells. If autoantibodies have a deleterious effect in IDDM, it is contemplated that anti-B-cell therapy can slow or stem the progress of the disease from prediabetes to clinical IDDM.

Another use of the present ICA antigens is in the identification of islet-reactive T-cell populations. ICA antigens can serve as stimulating antigens for T-cell culture, permitting significantly improved T-cell cloning, identification, and growth. It is contemplated that ICA T-cell detection can be significant in the diagnosis of the pre-diabetic state, and that monitoring the level of autoreactive T-cells can give an indication of the progress of the disease and the utility of immune modulating therapies. Further, the generation of ICA T-cell cultures can provide an in vitro model for designing diabetic therapies. Finally, it is contemplated that T-cell immunization can halt or retard autoimmunity by generating a humoral response against self-destructive elements.

The ability of ICA antigens to bind to human ICA immunoglobulin and T-cells can be used to block the binding of ICA to islet cells and islet cell components in vivo, and therefore are contemplated to provide a direct therapeutic effect.

The present invention will now be illustrated, but is not intended to be limited, by the following examples.

EXAMPLES 1. cDNA Library

Islets of Langerhans were purified by Dr.'s Paul Lacy and David Scharp at Washington Univ., St. Louis, Mo., USA, following a published procedure. [C. Ricordi, P. E. Lacy, E. H. Finke, B. J. Olack, and D. W. Scharp: An Automated Method for Isolation of Human Pancreatic Islets. Diabetes 37:413–420 (1988)]. Briefly, human pancreas was perfused with collagenase and then ground up. Ficoll gradient centrifugation was used to isolate the islets, which were then cultured for 1 week at room temperature. The islets were frozen and shipped.

Upon receipt, the islets were thawed, pooled, and washed. RNA was extracted using guanidinium thiocyanate and selectively precipitated with lithium chloride [G. Cathala, J. F. Savouret, B. Mendez, B. L. West, M. Karin, J. A. Martial, and J. D. Baxter: A Method for Isolation of Intact, Transtationally Active Ribonucleic Acid. DNA 2:329–335 (1983)]. About 770 $\mu$g of total RNA was obtained from each ml of centrifuged islets. Messenger RNA was purified using Pharmacia Oligo(dT)-cellulose Type 7 (Pharmacia Fine Chemicals, Piscataway, N.J., USA), following the procedure of Maniatis et al, [T. Maniatis, E. F. Fritsel, and J. Sambrook: Molecular Cloning, A Laboratory Manual (1982) Cold Spring Harbor Laboratory p. 197–198]. About 30 $\mu$g RNA was obtained after chromatography. In vitro translation using a BRL kit #8110 (Bethesda Research Laboratory, Gaithersburg, Md., USA), and $^{35}$S-methionine showed a broad range of molecular weight proteins being produced.

A BRL #8267SA kit was used for cDNA synthesis. Ten (10) $\mu$g of poly-A$^+$ RNA was used in the reaction. The ends were polished with $T_4$-DNA polymerase (Pharmacia), and the cDNA was methylated with Eco RI methylase (New England Biolabs, Beverly, Mass., USA) and S-adenosyl methionine and ligated to Eco RI linkers. The cDNA was digested with Eco RI and run on a Biogel A15M column (BioRad Laboratories, Rockville Center, N.Y., USA) to separate the linkers and fragments.

The cDNA was ligated into lambda gt-11 arms and packaged with a Stratagene Gigapack Plus kit (Stratagene Cloning Systems, LaJolla, Calif., USA). A library of approximately 8.5×10$^5$ insert-containing clones was obtained (measured with 5-bromo-4-chloro-3-indolyl-β-D-galactopyranoside), and amplified on E. coli Y1090 (Stratagene).

2. Sera

Sera from newly diagnosed diabetics were obtained from Dr. William Riley at the University of Florida, Gainesville, Fla., USA, and Dr. Alan Drash at the Children's Hospital of Pittsburgh, Pittsburgh, Pa., USA. Normal (non-diabetic) sera were collected from individuals in the laboratory. Sera from non-diabetic children were obtained from Dr. Jocelyn Hicks at the Children's National Medical Center in Washington, D.C. Sera were multiply adsorbed with filters that were prepared either by (a) lysing lambda-infected E. coli with chloroform and soaking nitrocellulose filters in this lysate, or (b) preparing filters by overlaying filters soaked with isopropyl-β-thio-galactopyranoside (IPTG) on lambda-infected E. coli in a plate format, essentially in the same manner as screening the library. Sera were diluted 1/20–1/200 in blotto solution (5% Carnation non-fat dry milk, 10 mM Tris pH 8.0, 150 mM NaCl, 0.05% Tween-20, and 0.05% sodium azide) after crude fractionation as noted below. Sera were used for ELISA experiments without preadsorption.

3. Screening

The screening procedure is based on standard protocols (T. V. Huynh, R. A. Young and R. W. Davis: Constructing and Screening cDNA Libraries in Fgt 10 and Gft 11 in DNA Cloning. D. M. Glover ed. (1985) IRL Press p. 490–78). Filters were prepared by plating about 50,000 plaque forming units (pfu) of the library onto each of ten 150 mm agarose plates. After growth at 42° C. for about 3 hours, filters (Nitrocellulose from Schleicher and Schuell, Keene, N.H., USA) containing IPTG were laid onto the plates and growth was continued at 37° C. for either 3–4 hours or overnight. Filters were blocked with a blotto solution and stored at 4° C.

Initially, all antibody reactions with filters were performed at room temperature for 3 hours. In later experiments, sera incubations were done overnight at 4° C. in blotto solution without S Tween-20, while secondary antibody reactions were done at room temperature for 1.5 hours. All incubations and washing were done on platform shakers with gentle rotation.

The library was screened with human antibody probes several times. In the first instance, antibody was purified from diabetic sera by HPLC. In the second and third, sera were precipitated with 50% ammonium sulfate and dialyzed. For the first and third screenings, a mixture of two sera were used for all rounds of purification. For the second screening, a mixture of 20 diabetic sera was used for the primary purifications. In a further screening, 22 sera were pooled, precipitated with ammonium sulfate and dialyzed, and the final working dilution of each serum was 1/500 in blotto without Tween 20.

After incubation in the diabetic sera, filters were washed 5–10 minutes each in Tris-buffered saline (TBS), TBS with 0.05% Tween-20, and then in TBS. Human antibody bound to the filters was detected by reaction with rabbit anti-human IgG conjugated to alkaline phosphatase (1/500 in blotto, Dakopatts antibody D-336—DAKO Corp., Santa Barbara, Calif., USA). Filters were washed in TBS/Tween-20, TBS, TBS, and then detection buffer (0.1 M Tris-HCl, pH 9.5, 0.1 M NaCl, 0.05 M $MgCl_2$, recommended by BRL for use in their DNA detection kit No. 8239SA). Chromogenic substrates (nitro-blue tetrazolium and 5-bromo-4-chloro-3-indolyl phosphate) were added and the reaction was protected from light. After color development, the filters were washed in water, then in 10 mM Tris (pH 8.0), 1 mM EDTA (TE) and dried. Best observation of the plaques could be made when the filters were still matte wet.

Positive plaques were located on the original plates by alignment with the filters. For primary screens, a plug containing a positive plaque was removed using the butt end of a sterile Pasteur pipet. For subsequent screenings where individual plaques could be distinguished, the tip of the pipet was used. Plaques were eluted into plaque storage buffer (Maniatis et al., supra) and eluted for at least several hours.

The above screening methods produced the specific deposited ICA clones described herein with the exception of ICA-12.3 (ATCC 40550) and ICA-512.3 (ATCC 75030) which were isolated as follows.

Approximately $10^6$ plaque forming units of the phage library were screened by DNA hybridization for the presence of sequences homologous with the ICA-12 (ATCC 40550) cDNA. The phage plaques distributed over 20 agar plates were replicated onto nylon filters, and the phage DNA was denatured and immobilized for hybridization, by the conventional procedure of Benton and Davis (1977) Science 196:180. The hybridization probe was an agarose gel-purified sample of the cloned ICA-12 (ATCC 40550) cDNA separated from its plasmid vector by Eco RI digestion. The cDNA segment was tagged with $^{32}P$ by the random primer labeling method (Feinberg and Vogelstein (1984) Anal. Biochem. 137:266). Hybridization of the probe to nylon filters was done according to Berent et al. (1985) BioTech. 3:208. Phage plaques identified as containing DNA homologous with the ICA-12 (ATCC 40550) probe were picked from the master plates, and the phage were replicated for a second round of hybridization screening. Individual plaques remaining positive for ICA-12 (ATCC 40550) sequences were then characterized as to properties of cDNA inserts. The clone ICA-12.3 (ATCC 40703) was found by DNA sequence analysis to contain the entire protein coding sequence of the mRNA partially represented in ICA-12 (ATCC 40550).

Monoclonal antibodies (mAb) were raised using GST-ICA-512 (ATCC 40706) (see below) as immunogen. A mixture of culture supernatants from three mAb clones were pooled and used to screen the human islet lambda-gtll expression library. The screening method was as described above, except that an alkaline phosphatase conjugated rabbit anti-mouse Ig (DAKO) was used as a second antibody. Clone ICA-512.2 was obtained and determined to have 670 bases more than ICA-512 (ATCC 40706) on the 5' end.

Since it appeared that ICA-512.2 did not contain the initiation site for the full length protein, a DNA probe was made by labelling a 230 base Pst I restriction fragment that was derived from the 5' section of ICA-512.2, (bases 201–431, corresponding to bases 1216–1446 of ICA-512.3 (ATCC 75030), shown in SEQ ID NO 10). This fragment was used to screen the library, and clone ICA-512.3 (ATCC 75030) was identified. SEQ ID NO 10 shows the DNA and inferred protein sequence of this clone.

4. Expression

The proteins expressed by individual clones were analyzed by expressing the clones in E. coli hosts. Initial expressions with clones identified as ICA-12 (ATCC 40550) and ICA-13 (ATCC 40553) were done with lysogens generated with the clones by standard means (Huynh, et al.). Subsequent expressions were done by infective expression into E. coli CAG-456 [M. Snyder, S. Elledge, D. Sweetser, R. A. Young, and R. W. Davis: Fgt-11: Gene Isolation with Antibody Probes and Other Applications, Meth. Enzymology 154:107–128 (1987)]. Cells were harvested and lysed by resuspension in Laemmli sample buffer [U. K. Laemmli, Nature 227:680 (1970)]. Better electrophoresis results were obtained when samples were sonicated to reduce the size of the DNA and reduce viscosity.

Protein gel electrophoresis and semi-dry electrotransfer onto either nitrocellulose (Schleicher and Shuell) or Immobilon (Millipore Company, Bedford, Mass., USA) were performed. Gels were stained with Coomassie Blue and filters were detected by immunoreaction with the same sera used to screen the library as detailed above.

5. Clone Analysis

In order to assess the usefulness of the individual clones for diagnosis of IDDM, each clone was tested for reactivity with a panel of diabetic and normal sera. This was done by reacting each serum with a western blot strip from each clone. Preparative gel electrophoresis was followed by semi-dry electrotransfer of the proteins to filters. Identical 3 mm strips were cut from the filters and exposed to the various sera. Localization of antigen bands was done by reference to analytical western blots and strips reacted with anti-beta-galactosidase antibody (1/2000 monoclonal antibody from Promega, Madison, Wis., USA). Antibody incubation and detection with secondary antibody were described above.

Figure 6A:
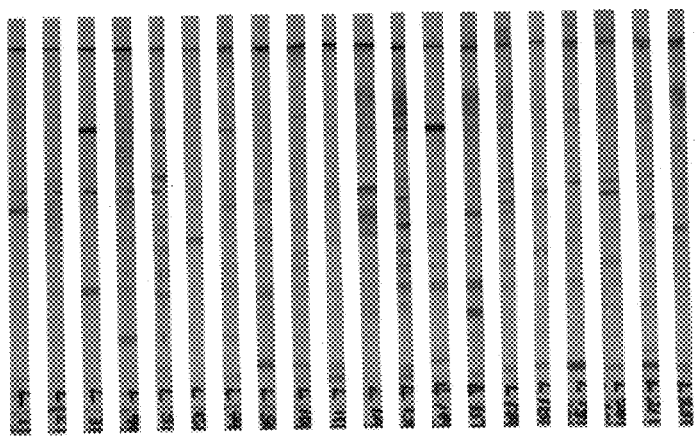
FIG. 6 is a control profile using the cloning phage with no recombinant insert.
Figure 6B:
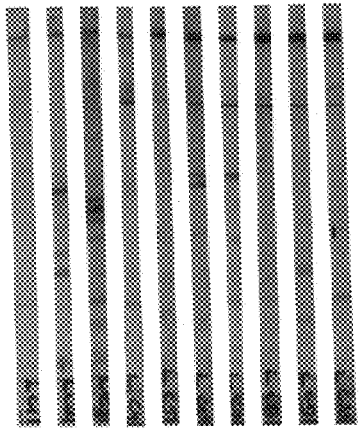
Figure 8A:
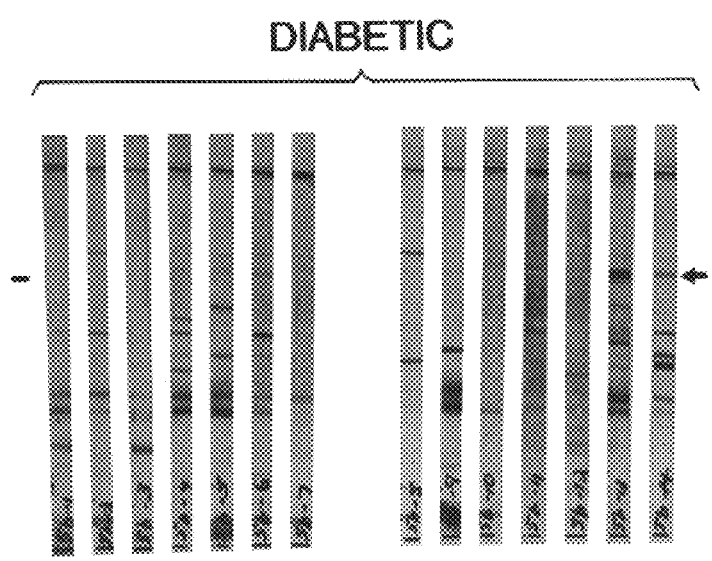
Figure 8B:
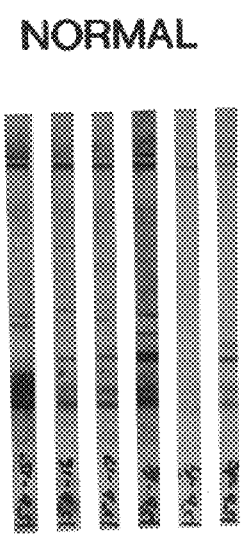
Figure 11A:
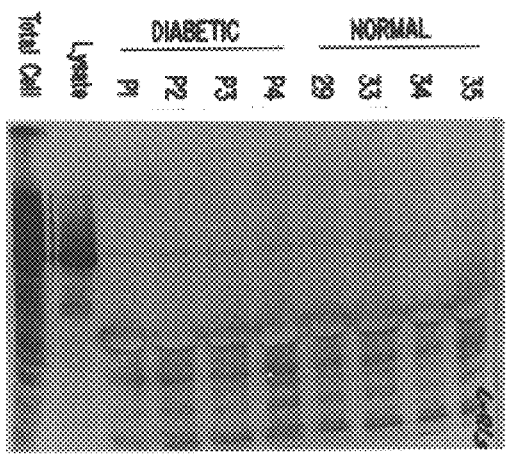
FIG. 11 shows the results of immuno-precipitation of one of the ICA clones with diabetic and normal sera.
Figure 11B:
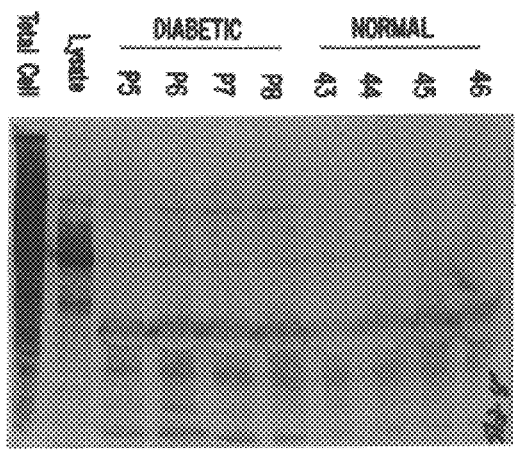
Figure 11C:
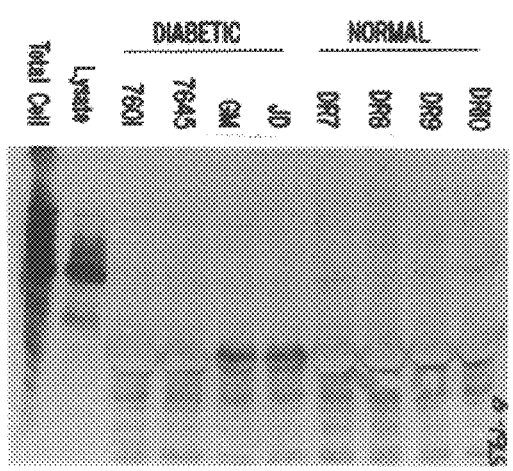
Figure 11D:
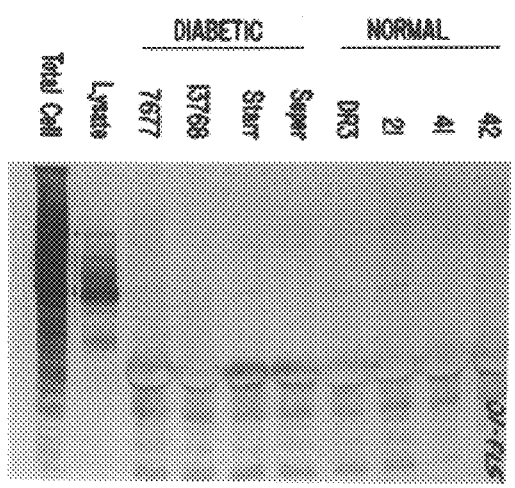

The reactivity profiles of the clones identified as ICA-12 (ATCC 40550), ICA-13 (ATCC 40553), ICA-208 (ATCC 40554), ICA-302 (ATCC 40551), ICA-313 (ATCC 40552), ICA-505 (ATCC 40705), and ICA-525 (ATCC 40704) are shown in FIGS. 1–5, 8 and 9 of the drawings. Identical filter strips were cut from preparative electrotransfer and reacted with diabetic and normal sera (for ICA-12 (ATCC 40550), 13 (ATCC 40553), 208 (ATCC 40554), 302 (ATCC 40551), and 313 (ATCC 40552), the strips were reacted with 20 diabetic and 10 normal sera; while 14 diabetic and 6 normal sera were used for ICA-505 (ATCC 40705) and 525 (ATCC 40704)). A control profile using the vector (lambda gt-11) having no DNA insert is shown in FIG. 6.

The filter strips were also rated according to intensity, 1=weak reactivity, 2, 3 and 4=very strong reactivity. Summaries of the reactivity ratings are given in FIGS. 7 and 10 of the drawings. In FIG. 7, sera 21–30 bearing the prefix "c" are the normal control sera, while the diabetic sera are presented with their source identification number. In FIG. 10, sera 15–20 bearing the "MRC" prefix are normal control sera, while again the diabetic sera are presented with their source identification numbers. In both Figures, the numbers shown under the clone headings represent the strength of immunoreactivity assigned by visual interpretation.

Some clones identified in the first screening were found to be unreactive in the western blot format. To test the serum reactivity of these clones, the lambda gt-11 phage were expressed in *E. coli* CAG456 as above and the antigen was extracted by treating the bacteria with 4 mg/ml lysozyme (Sigma, St. Louis, Mo., USA) in 25 mM Tris, pH 8, 10 mM EDTA, 50 mM glucose and 2 mM phenyl-methyl sulfonyl chloride (PMSF) for 5 minutes at room temperature. Cells were pelleted at 4° C. and resuspended in ice cold buffer (500 mM sodium chloride, 1% NP-40, 50 mM Tris, pH 8, 1 mg/ml aprotinin (Sigma), 2 mM PMSF, 2 µg/ml chymostatin (Sigma), 2 µg/ml Antipain (Sigma) and 2 µg/ml pepstatin. Extraction of antigen proceeded for 30 minutes on ice, during which time the solution was sonicated. Samples were spun in an Eppendorf microfuge for 5 minutes at 4° C. and supernatants were used for immunoprecipitation.

Immune reactions consisted of: 15 µl wash buffer (50 mM Tris, 150 mM sodium chloride, 1% NP-40, 5 mM EDTA, 2 mM PMSF, 2.5 µl human serum, and 10 µl extract. Reactions were left overnight. Antigen-antibody complexes were recovered with 20 µl of a 50% slurry of Protein-A Sepharose CL-4B (Pharmacia) for 1 hour on ice. The resin was washed six times with 500 µl of wash buffer and once with water. Sample buffer for PAGE was added and the samples were boiled for 5 minutes, centrifuged for 5 minutes, and run on 8% gels. Electroblotting was performed and the blots reacted with anti-beta-galactosidase antibody (1/1000 dilution of Sigma #G4644 in blotto solution) followed by anti-mouse Ig coupled to alkaline phosphatase (DAKO #D314) and development in dyes. The results are shown in FIG. 11 for an extract of ICA-512 (ATCC 40706). Arrows indicate the position of the recombinant antigen.

DNA insert size for the various clones was determined by growing them either in a plate lysate or liquid lysate format (Maniatis, et al., supra). Lambda DNA was extracted, and cut with Eco RI, and analyzed for size by agarose gel electrophoresis.

The above identified clones which reacted predominantly with diabetic sera have been deposited with the American Type Culture Collection, Rockville, Md., USA. The SEQ ID NOs, deposit numbers, deposit dates, and determined insert sizes are shown in Table 1 below. All restrictions upon public access to these deposits will be irrevocably removed upon the grant of a patent and each deposit will be replaced if viable samples cannot be dispensed by the depository.

TABLE 1

| SEQ ID NO | Clone # | ATCC# | Deposit Date | Insert size (kb) |
| --- | --- | --- | --- | --- |
| 1 | ICA-12 | 40550 | Feb. 8, 1989 | 1.400 |
| 2 | ICA-13 | 40553 | Feb. 8, 1989 | 5.043 |
| 3 | ICA-208 | 40554 | Feb. 8, 1989 | 0.575 |
| 4 | ICA-302 | 40551 | Feb. 8. 1989 | 0.794 |
| 5 | ICA-313 | 40552 | Feb. 8, 1989 | 2.391 |
| 6 | ICA-12.3 | 40703 | Nov. 14, 1989 | 3.243 |
| 7 | ICA-525 | 40704 | Nov. 14, 1989 | 3.4 |
| 8 | ICA-505 | 40705 | Nov. 14, 1989 | 0.346 |
| 9 | ICA-512 | 40706 | Nov. 14, 1989 | 1.8 |
| 10 | ICA-512.3 | 75030 | June 13, 1981 | 3.3 |

DNA inserts were transferred to a Stratagene Blue-script vector. Sequencing was done by standard techniques using the T7 Sequencing kit (Pharmacia) in conjunction with the Stratagene Exo III/Mung bean nuclease kit for generating overlapping nested deletion series of plasmids.

The sequence is considered to be complete for ICA-12 (ATCC 40550), 302 (ATCC 40551), 313 (ATCC 40552), 208 (ATCC 40554), 505 (ATCC 40305), 12.3 (ATCC 40703), 512 (ATCC 40706), and 512.3 (ATCC 75030), while only partial sequencing is available for ICA-13 (ATCC 40553) and 525 (ATCC 40704). The DNA sequences are those experimentally derived as described above. All three possible reading frames in both orientations were examined for protein coding capability, i.e., long open read frames. The most likely protein sequence for each clone is presented in capital letters below the DNA sequence (except for ICA-505 (ATCC 40705) for which the available information does not permit assignment of the reading frame encoding the protein antigen).

ICA-512 (ATCC 40706) was transferred to a modified version of plasmid pGEX (Pharmacia) for protein expression and purification. This modified plasmid, pGEXc, was adapted for expression of lambda-gt11 products by inserting 2 additional bases between the Bam H1 and EcoRI restriction sites.

A pGEXc clone that was determined to bear the ICA-512 (ATCC 40706) insert in the correct orientation by restriction analysis and DNA sequenceing was expressed following the protocol suggested by the manufacturer (Pharmacia) except that growth after induction with IPTG was at 25° C. Cell lysis, purification of the GST-ICA-512 (ATCC 40706) fusion protein on a glutathione-Sepharose 4B column, cleavage of the fusion protein with thrombin (Sigma T-7009) and purification of the ICA-512 (ATCC 40706) cleaved product with glutathione-Sepharose 4B were performed as described [D. B. Smith and K. S. Johnson: Single-step purification of polypeptides expressed in *Escherichia coli* as fusions with glutathione S-transferase. Gene 67:31–40 (1988)].

ICA-512 (ATCC 40706) was adapted to an ELISA format to provide quantitative information about a large number of samples. Both the GST-ICA-512 (ATCC 40706) and the cleaved ICA-512 were evaluated, and shown to give similar results with a panel of normal and diabetic sera.

Figure 12:
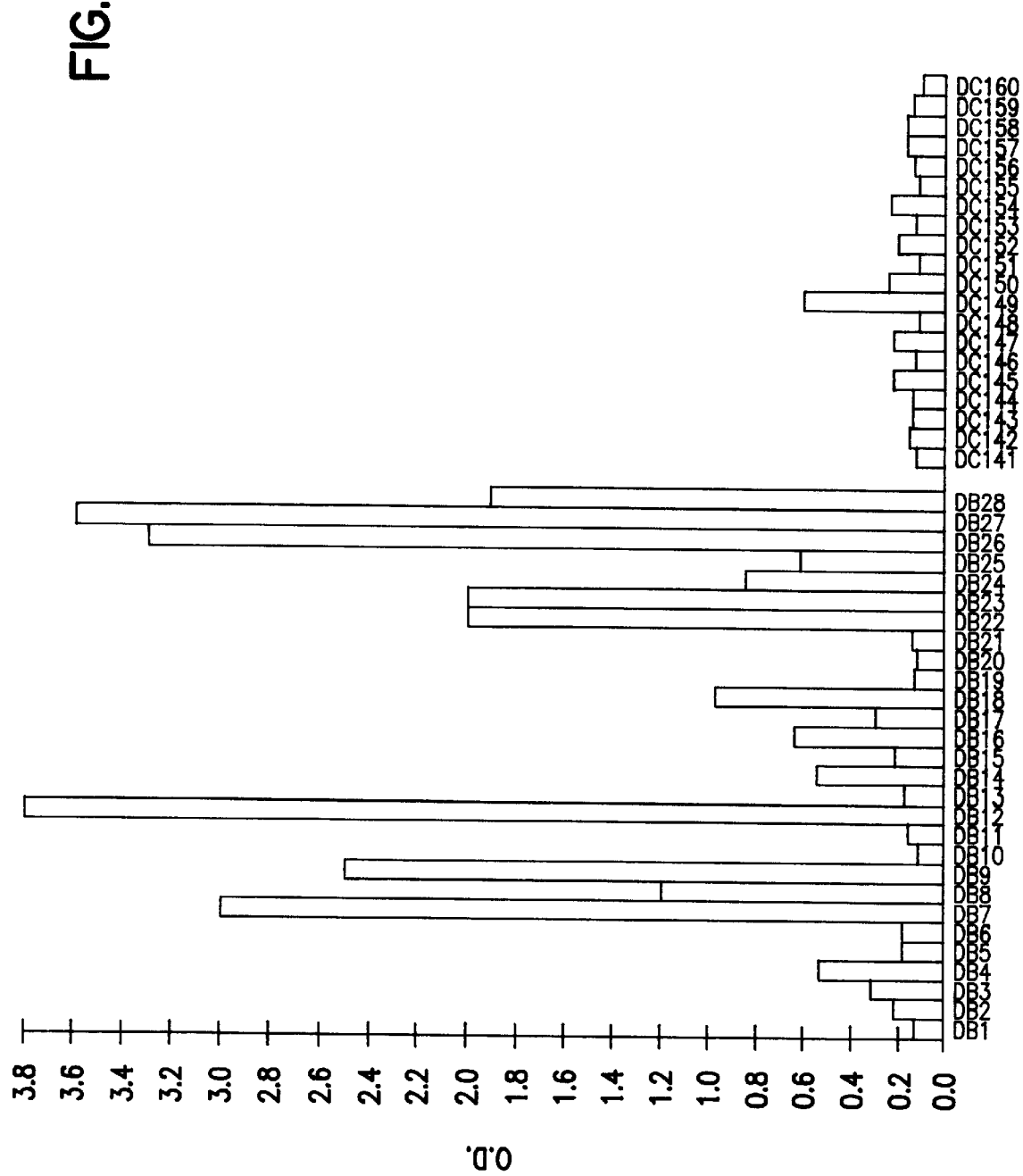
FIGS. 12 and 13 show ELISA profiles illustrating the specificity of reactivity of particular ICA clones (ICA-512 (ATCC40706) and ICA-12 (ATCC40550)) with diabetic sera.

FIG. 12 shows the reactivity of ICA-512 (ATCC 40706) with such a panel. The "DB" sera on the left are newly diagnosed diabetics, and the "DC" sera on the right are normal sera. In this experiment, 30 ng of cleaved and purified ICA-512 (ATCC 40706) was deposited in each well of an Immulon-2 microtiter plate (Dynatech, Chantilly, Va.) in TBS buffer and allowed to stand overnight. Other coating buffers have been tested and shown to be equivalent. All incubations and reactions were done at room temperature with orbital shaking. Unbound antigen was shaken out. The plate was blocked with a blotto solution containing Tween-20 for 1 hour, and then reacted with 1.5 µl of human serum diluted in 50 µl blotto/Tween. Incubation was for 1 hour. After washing 5 times with PBS/Tween, the wells were incubated with 100 µl of a 1/000 dilution of alkaline phosphatase (AP) conjugated anti-human IgG antibody (Sigma A-0287) for 1 hour. After washing 5 times in PBS/Tween and once for 15 minutes with TBS/Tween, the plate was developed with nitrophenyl-phosphate (1 Sigma tablet #104-105 in 10 ml of 1 M diethanolamine, 0.5 mM MgCl$_2$, pH 9.8) for 1–2 hours. Optical density was read at 405 nm.

Figure 13A:
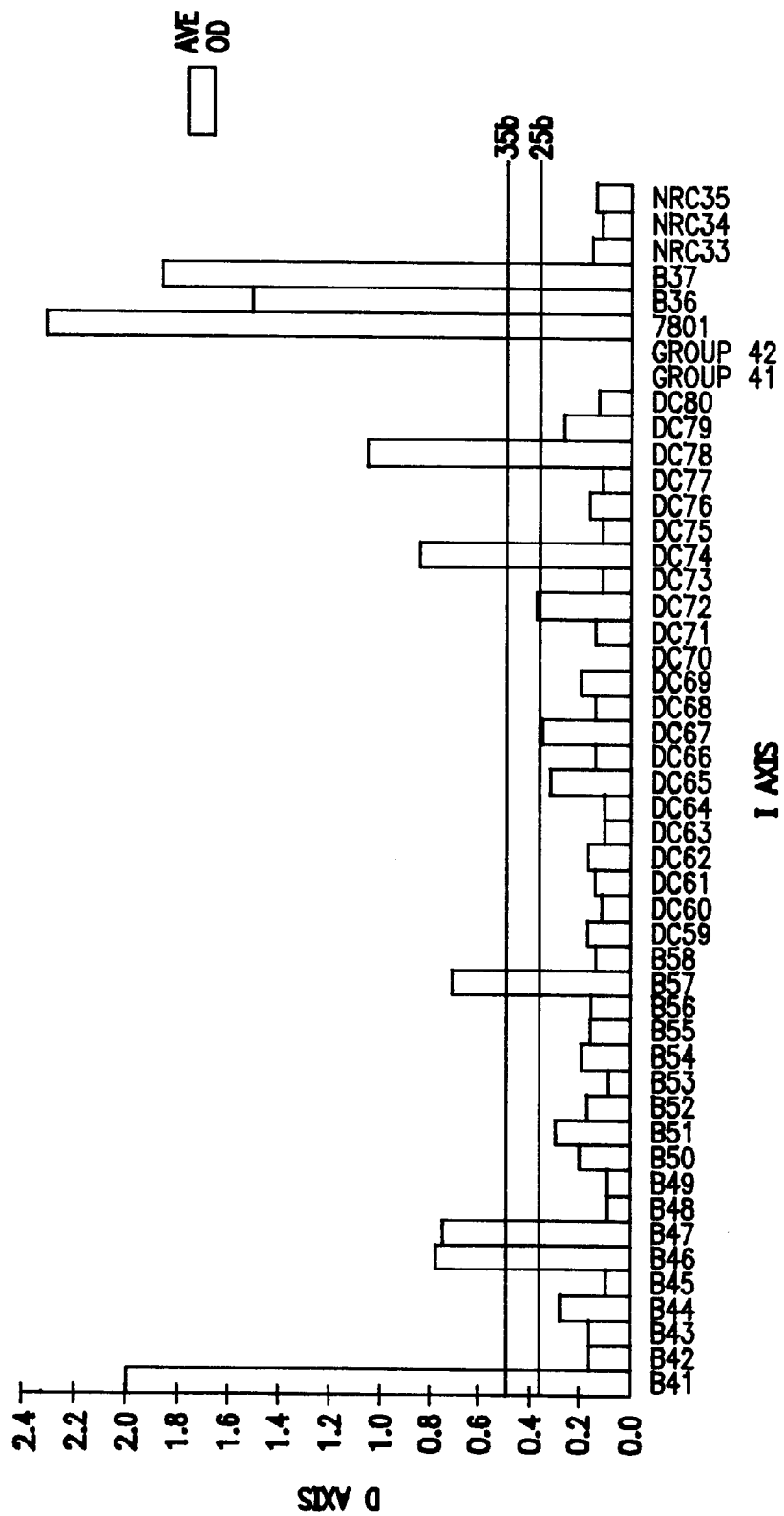
Figure 13B:
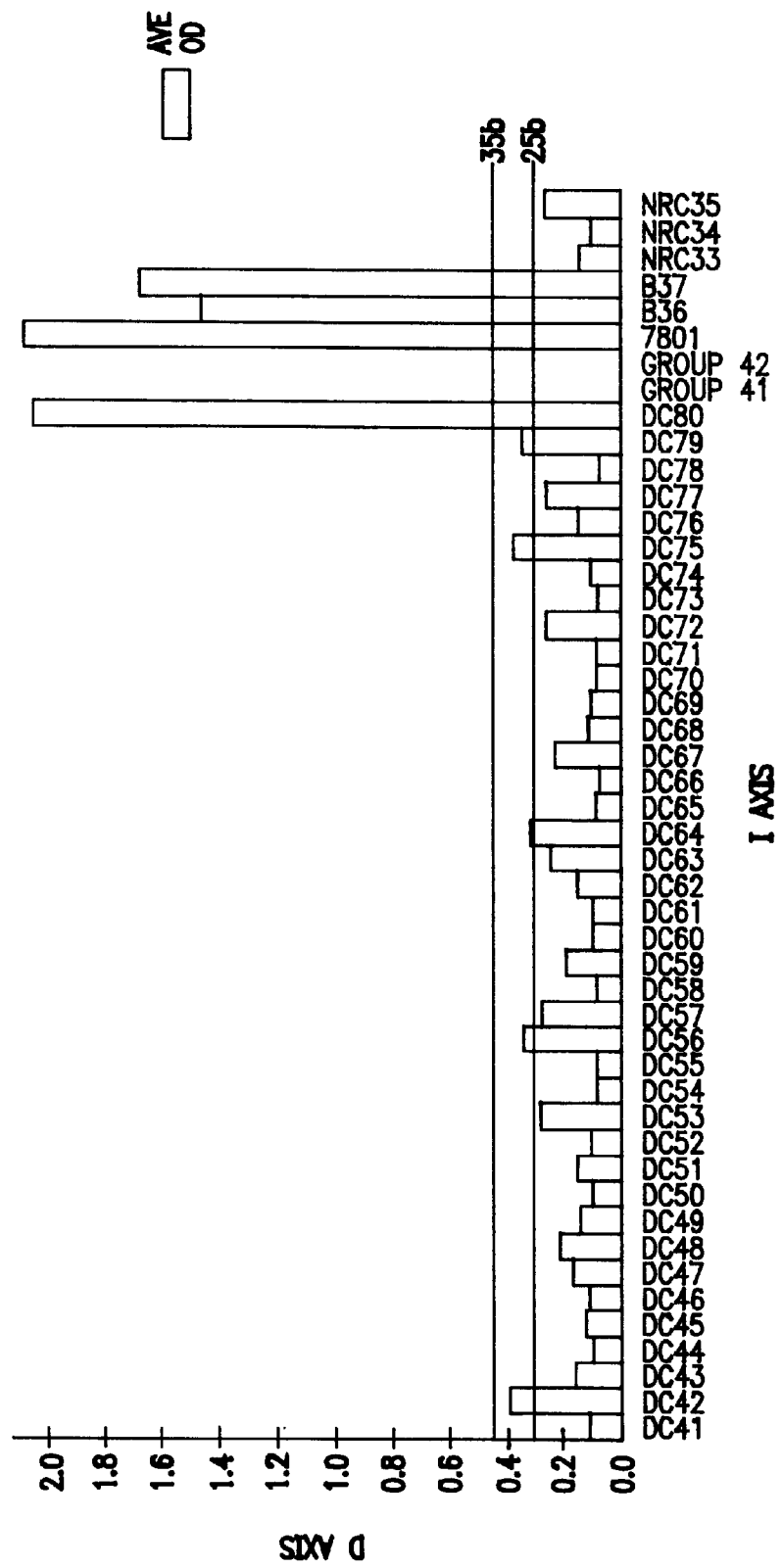

FIG. 13 shows the reactivity of a panel of diabetic (G) and normal (DC) sera with ICA-12 (ATCC 40550) in an ELISA format. The last 6 sera on the right side of the panel are controls. In this experiment, a capture format was used, in which an Immulon-1 plate (Dynatech) was coated first with a conjugate of glutathione and bovine serum albumin (GT-BSA). This conjugate was formed by reacting 2 mg of reduced glutathione (Sigma G-4251) dissolved in 500 µl PBS with 2 mg maleimide activated BSA (Pierce 77115H) dissolved in 200 µl water for 2 hours at room temperature. The mixture containing the modified BSA was diluted 1/1400 in EIA coating buffer (0.1 M sodium carbonate, pH 9.5), and each well of the 96-well plate was coated with 50 µl overnight at room temperature. The plate was blocked as described above, washed, and each well was exposed to 300 ng GST-ICA-12 (ATCC 40550) fusion protein dissolved in 50 µl blott/Tween for 1 hour at room temperature. Incubation with human sera, washing, and development were done as described above.

The present invention has been particularly described and exemplified above. It is contemplated that many other variations and modifications of the invention can be made without departing from the spirit and scope hereof.

What is claimed is:

1. An isolated and purified DNA sequence comprising a nucleotide sequence encoding a polypeptide comprising the sequence of amino acids encoded by the DNA insert of a recombinant cloning vehicle selected from the group consisting of ATCC 40550 (SEQ ID NO.: 1), 40551 (SEQ ID NO.: 4), 40552 (SEQ ID NO.: 5), 40553 (SEQ ID NO.: 2), 40554 (SEQ ID NO.: 3), 40703 (SEQ ID NO.: 6), 40704 (SEQ ID NO.: 7), 40705 (SEQ ID NO.: 8), 40706 (SEQ ID NO.: 9) and 75030 (SEQ ID NO.: 10).

2. An isolated and purified DNA sequence according to claim 1, which is a DNA sequence encoding a polypeptide comprising the sequence of amino acids encoded by the DNA insert of recombinant cloning vehicle ATCC 40550 (SEQ ID NO.: 1).

3. An isolated and purified DNA sequence according to claim 1, which is a DNA sequence encoding a polypeptide comprising the sequence of amino acids encoded by the DNA insert of recombinant cloning vehicle ATCC 40551 (SEQ ID No.: 4).

4. An isolated and purified DNA sequence according to claim 1, which is a DNA sequence encoding a polypeptide comprising the sequence of amino acids encoded by the DNA insert of recombinant cloning vehicle ATCC 40552 (SEQ ID NO.: 5).

5. An isolated and purified DNA sequence according to claim 1, which is a DNA sequence encoding a polypeptide comprising the sequence of amino acids encoded by the DNA insert of recombinant cloning vehicle ATCC 40553 (SEQ ID NO.: 2).

6. An isolated and purified DNA sequence according to claim 1, which is a DNA sequence encoding a polypeptide comprising the sequence of amino acids encoded by the DNA insert of recombinant cloning vehicle ATCC 40554 (SEQ ID NO.: 3).

7. An isolated and purified DNA sequence according to claim 1, which is a DNA sequence encoding a polypeptide comprising the sequence of amino acids encoded by the DNA insert of recombinant cloning vehicle ATCC 40703 (SEQ ID NO.: 6).

8. An isolated and purified DNA sequence according to claim 1, which is a DNA sequence encoding a polypeptide comprising the sequence of amino acids encoded by the DNA insert of recombinant cloning vehicle ATCC 40704 (SEQ ID NO.: 7).

9. An isolated and purified DNA sequence according to claim 1, which is a DNA sequence encoding a polypeptide comprising the sequence of amino acids encoded by the DNA insert of recombinant cloning vehicle ATCC 40705 (SEQ ID NO.: 9).

10. An isolated and purified DNA sequence according to claim 1, which is a DNA sequence encoding a polypeptide comprising the sequence of amino acids encoded by the DNA insert of recombinant cloning vehicle ATCC 40706 (SEQ ID NO.: 9).

11. An isolated and purified DNA sequence according to claim 1, which is a DNA sequence encoding a polypeptide comprising the sequence of amino acids encoded by the DNA insert of recombinant cloning vehicle ATCC 75030 (SEQ ID NO.: 10).

12. A RNA of the DNA sequence according to claim 1.
13. A RNA of the DNA sequence according to claim 2.
14. A RNA of the DNA sequence according to claim 3.
15. A RNA of the DNA sequence according to claim 4.
16. A RNA of the DNA sequence according to claim 5.
17. A RNA of the DNA sequence according to claim 6.
18. A RNA of the DNA sequence according to claim 7.
19. A RNA of the DNA sequence according to claim 8.
20. A RNA of the DNA sequence according to claim 9.
21. A RNA of the DNA sequence according to claim 10.
22. A RNA of the DNA sequence according to claim 11.
23. A recombinant cloning vehicle comprising a DNA sequence according to claim 1.
24. A recombinant cloning vehicle comprising a DNA sequence according to claim 2.
25. A recombinant cloning vehicle comprising a DNA sequence according to claim 3.
26. A recombinant cloning vehicle comprising a DNA sequence according to claim 4.
27. A recombinant cloning vehicle comprising a DNA sequence according to claim 5.
28. A recombinant cloning vehicle comprising a DNA sequence according to claim 6.

29. A recombinant cloning vehicle comprising a DNA sequence according to claim 7.

30. A recombinant cloning vehicle comprising a DNA sequence according to claim 8.

31. A recombinant cloning vehicle comprising a DNA sequence according to claim 9.

32. A recombinant cloning vehicle comprising a DNA sequence according to claim 10.

33. A recombinant cloning vehicle comprising a DNA sequence according to claim 11.

34. A culturable cell comprising a DNA sequence according to claim 1.

35. A culturable cell comprising a DNA sequence according to claim 2.

36. A culturable cell comprising a DNA sequence according to claim 3.

37. A culturable cell comprising a DNA sequence according to claim 4.

38. A culturable cell comprising a DNA sequence according to claim 5.

39. A culturable cell comprising a DNA sequence according to claim 6.

40. A culturable cell comprising a DNA sequence according to claim 7.

41. A culturable cell comprising a DNA sequence according to claim 8.

42. A culturable cell comprising a DNA sequence according to claim 9.

43. A culturable cell comprising a DNA sequence according to claim 10.

44. A culturable cell comprising a DNA sequence according to claim 11.

45. An isolated and purified DNA sequence consisting of nucleotides encoding a fragment of a polypeptide comprising the sequence of amino acids encoded by the DNA insert of a recombinant cloning vehicle selected from the group consisting of ATCC 40550 (SEQ ID NO.: 1), 40551 (SEQ ID NO.: 4), 40552 (SEQ ID NO.: 5), 40553 (SEQ ID NO.: 2), 40554 (SEQ ID NO.: 3), 40703 (SEQ ID NO.: 6), 40704 (SEQ ID NO.: 7), 40705 (SEQ ID NO.: 8), 40706 (SEQ ID NO.: 9) and 75030 (SEQ ID NO.: 10), said fragment being at least 3 amino acids long and being capable of binding an islet cell autoantibody.

46. An isolated and purified DNA sequence according to claim 45, which is a nucleotide sequence encoding a fragment of a polypeptide comprising the sequence of amino acids encoded by the DNA insert of recombinant cloning vehicle ATCC 40550 (SEQ ID NO.: 1).

47. An isolated and purified DNA sequence according to claim 45, which is a nucleotide sequence encoding a fragment of a polypeptide comprising the sequence of amino acids encoded by the DNA insert of recombinant cloning vehicle ATCC 40551 (SEQ ID NO.: 4).

48. An isolated and purified DNA sequence according to claim 45, which is a nudeotide sequence encoding a fragment of a polypeptide comprising the sequence of amino acids encoded by the DNA insert of recombinant cloning vehicle ATCC 40552 (SEQ ID NO.: 5).

49. An isolated and purified DNA sequence according to claim 45, which is a nudeotide sequence encoding a fragment of a polypeptide comprising the sequence of amino acids encoded by the DNA insert of recombinant cloning vehicle ATCC 40553 (SEQ ID NO.: 2).

50. An isolated and purified DNA sequence according to claim 45, which is a nudeotide sequence encoding a fragment of a polypeptide comprising the sequence of amino acids encoded by the DNA insert of recombinant cloning vehicle ATCC 40554 (SEQ ID No.: 3).

51. An isolated and purified DNA sequence according to claim 45, which is a nucleotide sequence encoding a fragment of a polypeptide comprising the sequence of amino acids encoded by the DNA insert of recombinant cloning vehicle ATCC 40703 (SEQ ID NO.: 6).

52. An isolated and purified DNA sequence according to claim 45, which is a nucleotide sequence encoding a fragment of a polypeptide comprising the sequence of amino acids encoded by the DNA insert of recombinant cloning vehicle ATCC 40704 (SEQ ID NO.: 7).

53. An isolated and purified DNA sequence according to claim 45, which is a nucleotide sequence encoding a fragment of a polypeptide comprising the sequence of amino acids encoded by the DNA insert of recombinant cloning vehicle ATCC 40705 (SEQ ID NO.: 8).

54. An isolated and purified DNA sequence according to claim 45, which is a nudeotide sequence encoding a fragment of a polypeptide comprising the sequence of amino acids encoded by the DNA insert of recombinant cloning vehicle ATCC 40706 (SEQ ID NO.: 9), said fragment being at least 3 amino acids long and being capable of binding an islet cell autoantibody.

55. An isolated and purified DNA sequence according to claim 45, which is a nucleotide sequence encoding a fragment of a polypeptide comprising the sequence of amino acids encoded by the DNA insert of recombinant cloning vehicle ATCC 75030 (SEQ ID NO.: 10), said fragment being at least 3 amino acids long and being capable of binding an islet cell autoantibody.

56. A recombinant cloning vehicle comprising a DNA sequence according to claim 12.

57. A recombinant cloning vehicle comprising a DNA sequence according to claim 13.

58. A recombinant cloning vehicle comprising a DNA sequence according to claim 14.

59. A recombinant cloning vehicle comprising a DNA sequence according to claim 15.

60. A recombinant cloning vehicle comprising a DNA sequence according to claim 49.

61. A recombinant cloning vehicle comprising a DNA sequence according to claim 50.

62. A recombinant cloning vehicle comprising a DNA sequence according to claim 51.

63. A recombinant cloning vehicle comprising a DNA sequence according to claim 52.

64. A recombinant cloning vehicle comprising a DNA sequence according to claim 53.

65. A recombinant cloning vehicle comprising a DNA sequence according to claim 54.

66. A recombinant cloning vehicle comprising a DNA sequence according to claim 55.

67. A culturable cell comprising a DNA sequence according to claim 45.

68. A culturable cell comprising a DNA sequence according to claim 46.

69. A culturable cell comprising a DNA sequence according to claim 47.

70. A culturable cell comprising a DNA sequence according to claim 48.

71. A culturable cell comprising a DNA sequence according to claim 49.

72. A culturable cell comprising a DNA sequence according to claim 50.

73. A culturable cell comprising a DNA sequence according to claim 51.

74. A culturable cell comprising a DNA sequence according to claim 52.

75. A culturable cell comprising a DNA sequence according to claim 53.

76. A culturable cell comprising a DNA sequence according to claim 54.

77. A culturable cell comprising a DNA sequence according to claim 54.

* * * * *